(12) United States Patent
Rothberg et al.

(10) Patent No.: US 10,283,928 B2
(45) Date of Patent: May 7, 2019

(54) COMPACT MODE-LOCKED LASER MODULE

(71) Applicant: Quantum-Si Incorporated, Guilford, CT (US)

(72) Inventors: Jonathan M. Rothberg, Guilford, CT (US); Jason W. Sickler, Madison, CT (US); Lawrence C. West, San Jose, CA (US); Faisal R. Ahmad, Guilford, CT (US); Paul E. Glenn, Wellesley, MA (US); Jack Jewell, Boulder, CO (US); John Glenn, Carlisle, MA (US); Jose Camara, Saratoga, CA (US); Jeremy Christopher Jordan, Cromwell, CT (US); Todd Rearick, Cheshire, CT (US); Farshid Ghasemi, Guilford, CT (US); Jonathan C. Schultz, Guilford, CT (US); Keith G. Fife, Palo Alto, CA (US); Benjamin Cipriany, Branford, CT (US)

(73) Assignee: Quantum-Si Incorporated, Guilford, CT (US)

( * ) Notice: Subject to any disclaimer, the term of this patent is extended or adjusted under 35 U.S.C. 154(b) by 0 days.

(21) Appl. No.: 15/844,469

(22) Filed: Dec. 15, 2017

(65) Prior Publication Data
US 2018/0175582 A1 Jun. 21, 2018

Related U.S. Application Data

(60) Provisional application No. 62/435,688, filed on Dec. 16, 2016.

(51) Int. Cl.
*H01S 3/11* (2006.01)
*H01S 3/10* (2006.01)
(Continued)

(52) U.S. Cl.
CPC .............. *H01S 3/1115* (2013.01); *G02F 1/37* (2013.01); *H01S 3/0092* (2013.01); *H01S 3/042* (2013.01);
(Continued)

(58) Field of Classification Search
CPC ...................................................... H01S 3/1115
See application file for complete search history.

(56) References Cited

U.S. PATENT DOCUMENTS

| 4,295,226 A | 10/1981 | Dombrowski |
| 5,108,179 A | 4/1992 | Myers |

(Continued)

FOREIGN PATENT DOCUMENTS

| EP | 0472318 A2 | 2/1992 |
| EP | 0542480 A2 | 5/1993 |

(Continued)

OTHER PUBLICATIONS

Won Sik Kwon, Hyub Lee, Jin Hwan Kim, Jindoo Choi, Kyung-Soo Kim, and Soohyun Kim, "Ultrashort stretched-pulse L-band laser using carbon-nanotube saturable absorber," Opt. Express 23, 7779-7785 (2015).*

(Continued)

*Primary Examiner* — Rhonda S Peace
(74) *Attorney, Agent, or Firm* — Wolf, Greenfield & Sacks, P.C.

(57) ABSTRACT

Apparatus and methods for producing ultrashort optical pulses are described. A high-power, solid-state, passively mode-locked laser can be manufactured in a compact module that can be incorporated into a portable instrument. The mode-locked laser can produce sub-50-ps optical pulses at a repetition rates between 200 MHz and 50 MHz, rates suitable for massively parallel data-acquisition. The optical pulses can be used to generate a reference clock signal for (Continued)

synchronizing data-acquisition and signal-processing electronics of the portable instrument.

39 Claims, 16 Drawing Sheets

(51) Int. Cl.
*G02F 1/37* (2006.01)
*H01S 3/00* (2006.01)
*H01S 3/08* (2006.01)
*H01S 3/16* (2006.01)
*H01S 3/042* (2006.01)
*H01S 3/0941* (2006.01)

(52) U.S. Cl.
CPC ........ *H01S 3/08072* (2013.01); *H01S 3/0941* (2013.01); *H01S 3/10046* (2013.01); *H01S 3/1611* (2013.01); *H01S 3/1673* (2013.01)

(56) References Cited

U.S. PATENT DOCUMENTS

| | | | |
|---|---|---|---|
| 5,471,515 A | 11/1995 | Fossum et al. | |
| 5,627,853 A | 5/1997 | Mooradian et al. | |
| 5,674,743 A | 10/1997 | Ulmer | |
| 5,822,472 A | 10/1998 | Burkhard et al. | |
| 6,355,420 B1 | 3/2002 | Chan | |
| 6,393,035 B1 | 5/2002 | Weingarten et al. | |
| 6,437,345 B1 | 8/2002 | Bruno-Raimondi et al. | |
| 6,716,394 B2 | 4/2004 | Jensen et al. | |
| 6,825,921 B1 | 11/2004 | Modlin et al. | |
| 6,834,064 B1* | 12/2004 | Paschotta | H01S 3/081 372/11 |
| 7,052,847 B2 | 5/2006 | Korlach et al. | |
| 7,170,050 B2 | 1/2007 | Turner et al. | |
| 7,179,654 B2 | 2/2007 | Verdonk et al. | |
| 7,394,841 B1 | 7/2008 | Konttinen et al. | |
| 7,595,883 B1 | 9/2009 | El Gamal et al. | |
| 7,738,086 B2 | 6/2010 | Shepard et al. | |
| 7,820,983 B2 | 10/2010 | Lundquist et al. | |
| 7,873,085 B2 | 1/2011 | Babushkin et al. | |
| 7,968,702 B2 | 6/2011 | Wegener et al. | |
| 7,981,604 B2 | 7/2011 | Quake | |
| 8,274,040 B2 | 9/2012 | Zhong et al. | |
| 8,279,901 B2* | 10/2012 | Karavitis | H01S 3/0057 359/348 |
| 8,465,699 B2 | 6/2013 | Fehr et al. | |
| 8,501,406 B1 | 8/2013 | Gray et al. | |
| 8,865,077 B2 | 10/2014 | Chiou et al. | |
| 9,318,867 B2* | 4/2016 | Pronin | H01S 3/0813 |
| 9,617,594 B2* | 4/2017 | Rothberg | H01S 3/1118 |
| 2003/0058904 A1* | 3/2003 | Krainer | H01S 3/113 372/25 |
| 2003/0169784 A1* | 9/2003 | Sutter | H01S 3/106 372/18 |
| 2003/0179786 A1 | 9/2003 | Kopf | |
| 2004/0047387 A1* | 3/2004 | Bunting | H01S 3/09415 372/70 |
| 2004/0169842 A1 | 9/2004 | Dosluoglu et al. | |
| 2008/0130099 A1 | 6/2008 | Harter | |
| 2010/0173394 A1 | 7/2010 | Colston et al. | |
| 2010/0245354 A1 | 9/2010 | Rousso et al. | |
| 2010/0255487 A1 | 10/2010 | Beechem et al. | |
| 2011/0136201 A1 | 6/2011 | Mao et al. | |
| 2011/0165652 A1 | 7/2011 | Hardin et al. | |
| 2011/0206072 A1 | 8/2011 | Karavitis | |
| 2011/0236983 A1 | 9/2011 | Beechem et al. | |
| 2012/0081040 A1 | 4/2012 | Ku | |
| 2013/0071849 A1 | 3/2013 | Kong et al. | |
| 2014/0286364 A1* | 9/2014 | Pronin | H01S 3/0813 372/18 |
| 2015/0293021 A1 | 10/2015 | Finkelstein et al. | |
| 2016/0084761 A1 | 3/2016 | Rothberg et al. | |
| 2016/0336709 A1* | 11/2016 | Manni | H01S 3/08081 |
| 2016/0341664 A1 | 11/2016 | Rothberg et al. | |
| 2016/0344156 A1 | 11/2016 | Rothberg et al. | |
| 2016/0369332 A1 | 12/2016 | Rothberg et al. | |
| 2018/0115136 A1* | 4/2018 | Delfyett | H01S 3/1118 |
| 2018/0175582 A1* | 6/2018 | Rothberg | G02F 1/37 |

FOREIGN PATENT DOCUMENTS

| | | |
|---|---|---|
| EP | 0601714 A1 | 6/1994 |
| EP | 1681356 A1 | 7/2006 |
| EP | 2182523 A1 | 5/2010 |
| WO | WO 02/11252 A2 | 2/2002 |
| WO | WO 2005/073407 A1 | 8/2005 |

OTHER PUBLICATIONS

Champak Khurmi, Nicolas Bourbeau Hébert, Wen Qi Zhang, Shahraam Afshar V., George Chen, Jérôme Genest, Tanya M. Monro, and David G Lancaster, "Ultrafast pulse generation in a mode-locked Erbium chip waveguide laser," Opt. Express 24, 27177-27183 (2016).*
Invitation to Pay Additional Fees for International Application No. PCT/US2016/033576 dated Aug. 24, 2016.
International Search Report and Written Opinion for International Application No. PCT/US2016/033576 dated Nov. 4, 2016.
Invitation to Pay Additional Fees for International Application No. PCT/US2016/033585 dated Sep. 21, 2016.
International Search Report and Written Opinion for International Application No. PCT/US2016/033585 dated Nov. 11, 2016.
International Search Report and Written Opinion for International Application No. PCT/US2017/066878 dated Mar. 15, 2018.
[No Author Listed] Semiconductor Components Industries, LLC, MC10EP05, MC100EP05. 3.3V/5V ECL 2-input differential and/ nand. Aug. 2008. 11 Pages.
Araki et al., An ultraviolet nanosecond light pulse generator using a light emiting diode for test of photodetectors. Rev. Sci. Instr. Mar. 1997;68:1364-8.
Binh et al., A simple sub-nanosecond ultraviolet light pulse generator with high repetition rate and peak power. Rev. Sci. Instr. 2013;84:083102.1-083102.5.
Huang et al., Gene expression analysis with an integrated CMOS microarray by time-resolved fluorescence detection. Biosensors and Bioelectronics. 2012;26(5):2660-5.
Huang et al., Slab-coupled Optical Waveguide Lasers Emerge from a Multimode Sea. www.photonics.com, Oct. 2006. 10 Pages.
Lu et al., Terahertz Microchip for Illicit Drug Detection. IEEE Photonics Technology Letters. 2006;18(21):2254-6.
Pfeufer et al., A ddT ddA ddG ddC Length-sorted strands fow through a capillary Detector Final output Focused laser beam Fluorescence Fluorescently teminated oligonucleotides Original DNA strand Genetics/DNA Sequencing. 2015;24-7.
Sauer et al., Time-Resolved Identification of Individual Mononucleotide Molecules in Aqueous Solution with Pulsed Semiconductor Lasers. Bioimaging, Institute of Physics. 1998;6(1):14-24.
Uhring et al., A low-cost high-repetition-rate picosecond laser diode pulse generator. Optical Sensing II. 2004;5452:583-90.

* cited by examiner

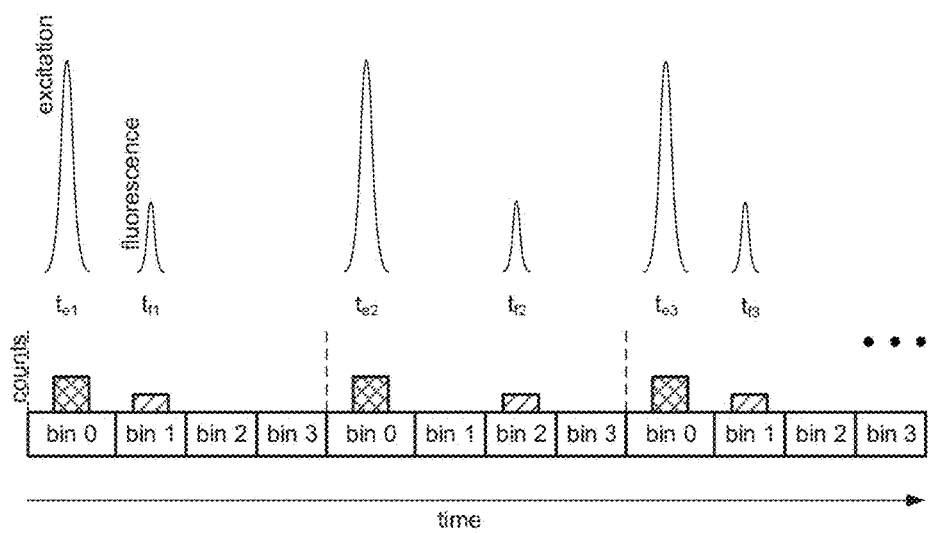
FIG. 1-10A
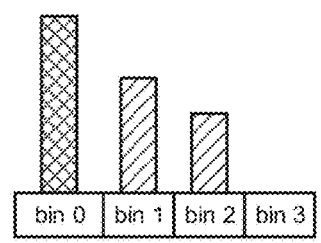
FIG. 1-10B
T
FIG. 1-11A
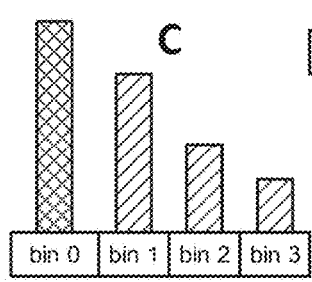
FIG. 1-11C
A
FIG. 1-11B
G
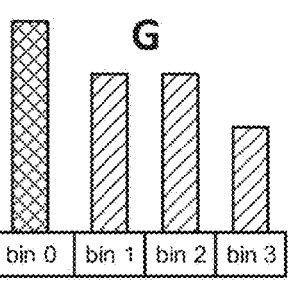
FIG. 1-11D

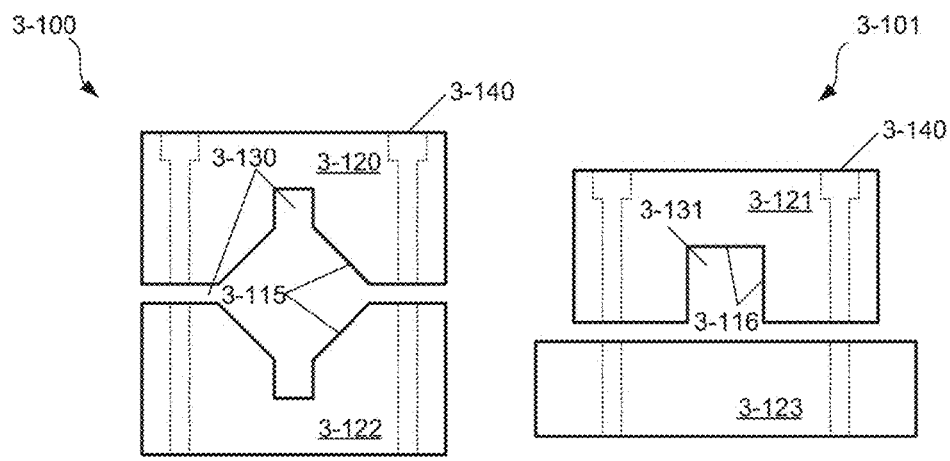
*FIG. 3-1A*
*FIG. 3-1B*
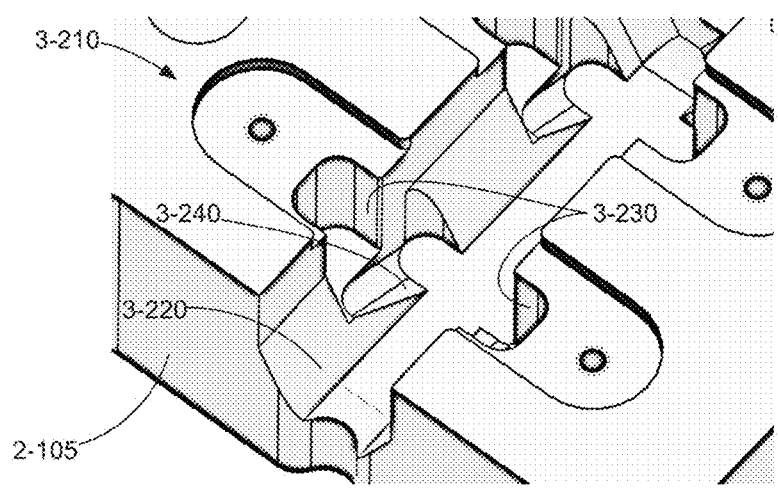
*FIG. 3-2A*

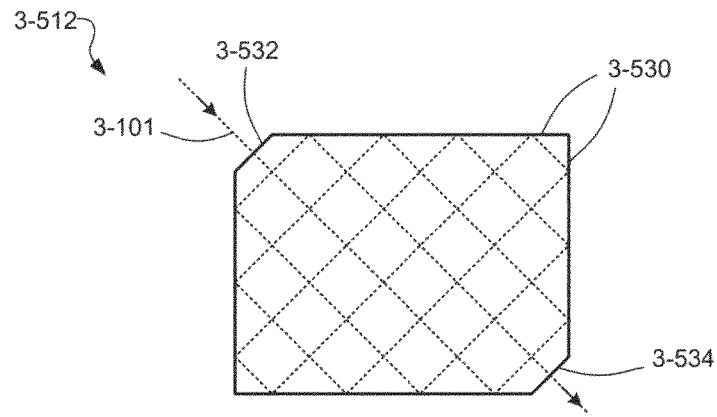
FIG. 3-5B
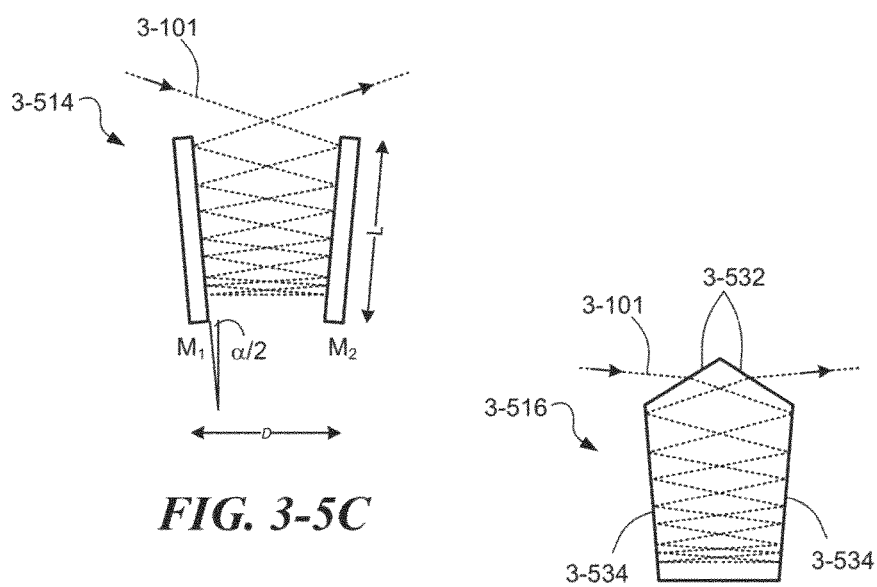
FIG. 3-5C
FIG. 3-5D

COMPACT MODE-LOCKED LASER MODULE

CROSS-REFERENCE TO RELATED APPLICATIONS

This application claims priority to U.S. provisional application No. 62/435,688, filed Dec. 16, 2016 and titled "Compact Mode-Locked Laser Module," which is incorporated by reference in its entirety.

FIELD

The present application is directed to compact apparatus and methods for producing sub-100-picosecond optical pulses. The apparatus may be incorporated into instrumentation that uses the optical pulses for analytical, medical, manufacturing, or communication purposes.

BACKGROUND

Ultrashort optical pulses (i.e., optical pulses less than about 100 picoseconds) are useful in various areas of research and development as well as commercial applications. For example, ultrashort optical pulses may be useful for time-domain spectroscopy, optical ranging, time-domain imaging (TDI), optical coherence tomography (OCT), fluorescent lifetime imaging (FLI), and lifetime-resolved fluorescent detection for genetic sequencing. Ultrashort pulses may also be useful for commercial applications including optical communication systems, medical applications, and testing of optoelectronic devices.

Conventional mode-locked lasers have been developed to produce ultrashort optical pulses, and a variety of such lasers are currently available commercially. For example, some solid-state lasers and fiber lasers have been developed to deliver pulses with durations well below 200 femtoseconds. However, for some applications, these pulse durations may be shorter than is needed and the cost of these lasing systems may be prohibitively high for certain applications. Additionally, these lasing systems may be stand-alone systems that have a sizeable footprint (e.g., on the order of 1 $ft^2$ or larger), have appreciable weight, and occupy a sizeable volume (e.g., 0.5 $ft^3$ or larger). Such lasing systems are not readily portable or incorporated into other portable systems as a module.

SUMMARY

The technology described herein relates to apparatus and methods for producing ultrashort optical pulses. A mode-locked laser system is described that can be implemented as a compact, low-cost laser module that is capable of producing sub-100-picosecond pulses at pulse-repetition rates as low as 50 MHz. The optical pulses from the laser can be detected electronically with circuitry included in the module, and the resulting signal can be processed to produce an electronic clock signal that can be used to synchronize other electronic systems with the stream of pulses (e.g., synchronize data-acquisition electronics of an instrument into which the laser module is incorporated). The inventors have recognized and appreciated that a compact, low-cost, pulsed-laser system can be incorporated into instrumentation (e.g., time-of-flight imaging instruments, bioanalytical instruments that utilize lifetime-resolved fluorescent detection, genetic sequencing instruments, optical coherence tomography instruments, etc.), and can allow such instrumentation to become readily portable and produced at appreciably lower cost than is the case for conventional instrumentation requiring an ultrashort pulsed laser. High portability can make such instruments more useful for research, development, clinical use, field deployment, and commercial applications. In an example application, the compact laser module can be incorporated into a portable genetic sequencing instrument, and the optical pulses can be delivered to reaction chambers where single-molecule sequencing events are detected.

Some embodiments relate to a mode-locked laser module comprising a base chassis; a mode-locked laser having a laser cavity assembled on the base chassis; and a gain medium located in the laser cavity that exhibits a thermal lensing value between four diopters and 15 diopters when the mode-locked laser is producing optical pulses.

Some embodiments relate to a mode-locked laser module comprising a base chassis; a mode-locked laser having a laser cavity assembled on the base chassis; an output coupler mounted on a first mount at a first end of the laser cavity, wherein the first mount provides no angular adjustment of the output coupler with respect to an optical axis of an intracavity beam that is incident on the output coupler; a saturable absorber mirror mounted on a second mount at a second end of the laser cavity, wherein the second mount provides no angular adjustment of the saturable absorber mirror with respect to the optical axis of the intracavity beam that is incident on the saturable absorber mirror; and a gain medium located between the mode-locked laser and the output coupler.

Some embodiments relate to a mode-locked laser module comprising a base chassis; an output coupler and a first focusing optic mounted on the base chassis; a saturable absorber mirror and second focusing optic mounted on the base chassis, wherein the output coupler and saturable absorber mirror comprise end mirrors of a laser cavity for the mode-locked laser; a gain medium located along an optical axis of an intracavity beam within the laser cavity; and a cavity length extending region comprising two reflectors located between the output coupler and the saturable absorber mirror, wherein the two reflectors fold the intracavity beam more than two times.

Some embodiments relate to a mode-locked laser module comprising a base chassis; a mode-locked laser having a first laser cavity configured to operate at a pulse repetition rate between 50 MHz and 200 MHz, wherein the mode-locked laser is assembled on the base chassis; a first end mirror of the first laser cavity located at a first end of the first laser cavity; a second end mirror of the first laser cavity located at a second end of the first laser cavity; and a gain medium located within the first laser cavity, wherein the gain medium is configured to exhibit thermal lensing when pumped at an operating power for the first laser cavity, wherein the thermal lensing supports lasing in a second laser cavity formed within the first laser cavity that is less than one-half the length of the first laser cavity and that includes the first end mirror and a third end mirror that is installed on the base chassis in the first laser cavity.

Some embodiments relate to a method of operating a mode-locked laser, the method comprising pumping a gain medium of a laser cavity with an optical pump beam, such that the gain medium exhibits thermal lensing having a range of diopter values between 8 diopters and 12 diopters; reflecting an intracavity beam from and output coupler at a first end of the laser cavity and a saturable absorber mirror at a second end of the laser cavity; and producing an output of stable optical pulses over the range of diopter values.

The foregoing and other aspects, implementations, acts, functionalities, features and, embodiments of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

FIG. 1-1B depicts a compact mode-locked laser incorporated into an analytical instrument, according to some embodiments.

FIG. 1-2 depicts a train of optical pulses, according to some embodiments.

FIG. 1-3 depicts an example of parallel reaction chambers that can be excited optically by a pulsed laser via one or more waveguides and corresponding detectors for each chamber, according to some embodiments.

FIG. 1-4 illustrates optical excitation of a reaction chamber from a waveguide, according to some embodiments.

FIG. 1-5 depicts further details of an integrated reaction chamber, optical waveguide, and time-binning photodetector, according to some embodiments.

FIG. 1-6 depicts an example of a biological reaction that can occur within a reaction chamber, according to some embodiments.

FIG. 1-7 depicts emission probability curves for two different fluorophores having different decay characteristics.

FIG. 1-8 depicts time-binning detection of fluorescent emission, according to some embodiments.

FIG. 1-9 depicts a time-binning photodetector, according to some embodiments.

FIG. 1-10A depicts pulsed excitation and time-binned detection of fluorescent emission from a sample, according to some embodiments.

FIG. 1-10B depicts a histogram of accumulated fluorescent photon counts in various time bins after repeated pulsed excitation of a sample, according to some embodiments.

FIG. 1-11A-1-11D depict different histograms that may correspond to the four nucleotides (T, A, C, G) or nucleotide analogs, according to some embodiments.

FIG. 2-1 depicts a compact mode-locked laser module, according to some embodiments.

FIG. 3-1A illustrates a mount for a gain medium or other high-power optical component which can be used in a compact mode-locked laser, according to some embodiments.

FIG. 3-1B illustrates a mount for a gain medium or other high-power optical component which can be used in a compact mode-locked laser, according to some embodiments.

FIG. 3-2A depicts an integrated optical mount, according to some embodiments.

FIG. 3-2B depicts an optic mounted in an integrated optical mount, according to some embodiments.

FIG. 3-3 depicts a saturable-absorber mirror and mount, according to some implementations.

FIG. 3-4 depicts an integrated optical mount, according to some embodiments.

FIG. 3-5A through FIG. 3-5D depict various embodiments of optical-path-length extenders which can be incorporated as part of a laser cavity, according to some implementations.

FIG. 3-6A depicts, in plan view, a platform for mounting a gain medium or other high-power optical system which can be used in a compact mode-locked laser, according to some embodiments.

FIG. 3-6B and FIG. 3-6C depict elevation views of the platform illustrated in FIG. 3-6A, according to some embodiments.

FIG. 4-1 depicts a diode-laser pump module, according to some embodiments.

FIG. 4-2A depicts an elevation view of an example adjustable, kinematic mounting assembly;

FIG. 4-2B depicts a plan view of an example adjustable, kinematic mounting assembly;

FIG. 5-1 depicts a system for synchronizing instrument electronics to timing of optical pulses, according to some embodiments.

FIG. 5-2 depicts clock-generation circuitry for an analytical instrument that incorporates a pulsed optical source, according to some embodiments.

FIG. 5-3 depicts system circuitry, according to some embodiments.

Figures 1, 1A:
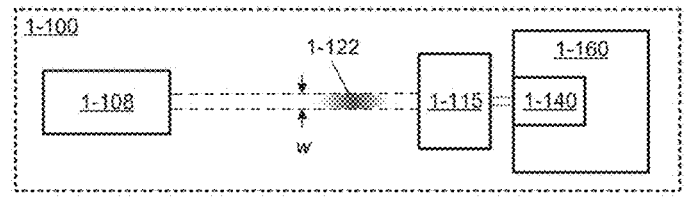
FIG. 1-1A is a block diagram depiction of an analytical instrument that includes a compact mode-locked laser module, according to some embodiments.

The features and advantages of the present invention will become more apparent from the detailed description set forth below when taken in conjunction with the drawings. When describing embodiments in reference to the drawings, directional references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of features of an embodied device. A device may be embodied using other orientations.

DETAILED DESCRIPTION

I. Introduction

The inventors have recognized and appreciated that conventional ultrashort-pulsed lasers capable of providing average output powers of at least 500 mW are typically large, expensive, and unsuitable for many mobile applications. Such lasers are typically too large and heavy to incorporate into portable instrumentation that can be adapted for imaging, ranging, or table-top bioanalytical applications. Accordingly, the inventors have conceived of compact, ultrashort-pulsed lasing systems that can provide sub-100-picosecond pulses at selected wavelengths and at average optical powers as high as 3.5 Watts (W). The lasing system can be configured to provide a repetition rate of optical pulses between about 50 MHz and about 200 MHz, which is well suited for massively parallel data acquisition. In some embodiments, an area occupied by a mode-locked laser module and its optics can be about the size of an A4 sheet of paper with a thickness of about 40 mm or less. A volume occupied by the module may be at most 0.07 ft$^3$, which is nearly a factor of 10 reduction in volume occupied by conventional ultrashort-pulsed lasers that cannot deliver as much optical power. Because the laser has a compact slab form factor, it can be readily incorporated into an instrument as a replaceable module, e.g., a module to swap in or out as one might add or exchange boards on a personal computer.

The term "optical" may refer to ultra-violet, visible, near-infrared, and short-wavelength infrared spectral bands.

In the area of bioanalytical technologies, such a compact mode-locked laser module can be used to deliver optical excitation energy to a plurality of reaction chambers integrated onto a chip, for example. The number of reaction chambers on the chip can be between about 10,000 and about 10,000,000, and the chambers can contain samples that can undergo multiple biochemical reactions over a period of time, according to some implementations. In other implementations, there can be fewer or more reaction chambers on the chip. According to some embodiments, the samples or molecules interacting with the samples can be labeled with one or more fluorophores that fluoresce(s), or the samples may fluoresce themselves, following excitation by an optical pulse from the mode-locked laser module. Detection and analysis of fluorescence from the reaction chambers provides information about the samples within the chambers.

To make a portable instrument that includes such a large number of reaction chambers and that uses multiple different fluorophores, requires addressing several technical challenges. A pulsed lasing system must be small and lightweight, and it must provide enough optical power (e.g., more than about 300 mW at a suitable excitation wavelength) to excite fluorophores in all the reaction chambers. The pulsed lasing system may also be required to produce a stream of ultrashort optical pulses that is stable over the duration of an assay or sequencing run, which can last for tens of minutes or hours. Additionally, there must be some way to excite different fluorophores with the mode-locked laser (e.g., four fluorophores with different emission characteristics for DNA sequencing), and detect different emission characteristics at appropriate times at each reaction chamber from the fluorophores so that each fluorophore can be distinguished from the other fluorophores to obtain useful information. Further, for applications involving integrated optical circuits on a chip, there must be some way to adapt an output beam from the laser module to match receiving optics at the chip, and to maintain stable and efficient coupling to the chip over long periods of time.

A compact mode-locked laser according to the present embodiments can be incorporated as an interchangeable module into portable instruments. A form factor for the module is a slab shape measuring no greater than 350 mm on a longest edge of the slab and having a thickness no greater than 40 mm, occupying a volume no greater than 0.1 cubic foot. In embodiments, a longest edge dimension can be a value between 300 mm and 350 mm, and a largest thickness can be a value between 30 mm and 40 mm. The weight of the module can be no greater than 2 kilograms, and operating power consumed by the module can be no more than 20 Watts. In embodiments, a maximum weight can be a value between 1 kilogram and 20 kilograms, and a maximum operating power can be a value between 10 Watts and 20 Watts. The laser can produce a stable train of sub-40-picosecond pulses at an excitation wavelength of approximately 532 nm at average output powers that can be controlled between 100 mW and 1.5 W. Mode-locked operation at a selected output power can be stable for hours. The module also includes circuitry for sensing optical pulses and optical power levels produced by the laser. A signal derived from sensing the optical pulses can be used to generate an electronic clock signal that can be used to synchronize instrument electronics (e.g., data acquisition cycles) with the timing of optical pulses produced by the laser.

II. Example Bioanalytical Application

By way of explanation, a bioanalytical application is described in which a compact mode-locked laser module is used to excite fluorophores in a plurality of reaction chambers on a chip. The example application is intended to highlight some of the more demanding requirements for the laser module, and is not intended to limit the laser module to only bioanalytic applications. The module can be used for other technologies such as communications, imaging, photonic chip or electronic chip probing and diagnosis, manufacturing (cutting, ablating), and medical treatment and diagnosis.

In overview, a portable analytic instrument 1-100 may comprise one or more mode-locked laser modules 1-108 mounted as a replaceable module within, or otherwise coupled to, the instrument, as depicted in FIG. 1-1A. The portable analytic instrument 1-100 can include an optical system 1-115 and an analytic system 1-160. The optical system 1-115 can include some combination of optical components (which may include, for example, none, one, or more of each of: lens, mirror, optical filter, attenuator, beam-steering component, beam shaping component) and be configured to operate on and/or deliver output optical pulses 1-122 from a mode-locked laser module 1-108 to the analytic system 1-160. The analytic system can include a plurality of components that are arranged to direct the optical pulses to at least one sample that is to be analyzed, receive one or more optical signals (e.g., fluorescence, backscattered radiation) from the at least one sample, and produce one or more electrical signals representative of the received optical signals. In some embodiments, the analytic system 1-160 can include one or more photodetectors and signal-processing electronics (e.g., one or more microcontrollers, one or more field-programmable gate arrays, one or more microprocessors, one or more digital signal processors, logic gates, etc.) configured to process the electrical signals from the photodetectors. The analytic system 1-160 can also include data transmission hardware configured to transmit and receive data to and from external devices via one or more data communications links. In some embodiments, the analytic system 1-160 can be configured to receive a bio-optoelectronic chip 1-140, which holds one or more samples to be analyzed.

Although the optical pulses 1-122 are depicted in the drawing as having a single transverse optical mode, in some embodiments, the optical output from a mode-locked laser module 1-108 may be multimodal (e.g., have a higher-order transverse mode). In such embodiments, a transverse output beam profile may have multiple intensity peaks and minima due to multimodal operation of the laser. In some embodiments, a multimodal output can be homogenized (e.g., by diffusing optics) by the optical system 1-115 or when coupled to the analytic system 1-160. In some implementations, a multimodal output can be coupled to a plurality of fibers or waveguides in the analytic system 1-160. For example, each intensity peak of a multimodal output can be coupled to a separate waveguide or waveguides in an array of waveguides that connect to the bio-optoelectronic chip 1-140. Allowing a mode-locked laser to operate in a multimode state can enable higher output powers from the mode-locked laser.

Figures 1, 1B:
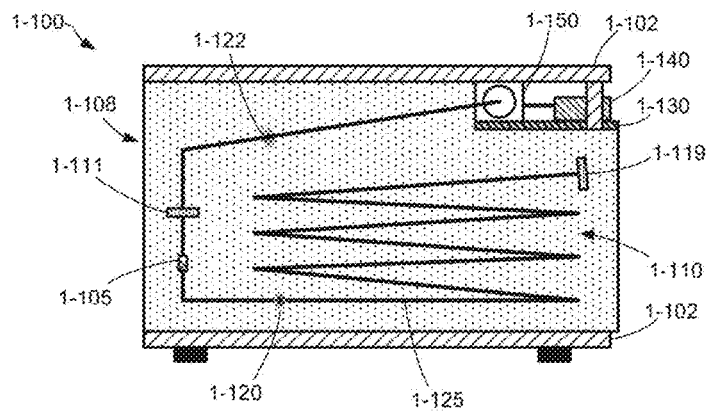

FIG. 1-1B depicts a further detailed example of a portable analytical instrument 1-100 that includes a compact mode-locked laser module 1-108. In some implementations, the module can be mounted to an instrument chassis or frame 1-102 of the instrument, and may be located inside an outer casing of the instrument. According to some embodiments, a mode-locked laser module 1-108 can include a mode-locked laser 1-110 and additional components that can be used to operate the mode-locked laser and operate on an output beam from the mode-locked laser. The mode-locked laser 1-110 may comprise an element (e.g., saturable absorber, acoustooptic modulator, Kerr lens) in a laser cavity, or coupled to the laser cavity, that induces phase locking of the laser's longitudinal frequency modes. The laser cavity can be defined in part by cavity end mirrors 1-111, 1-119. In some implementations, a mode-locked laser 1-110 can be passively mode locked, e.g., by a saturable absorber. Such locking of the frequency modes results in pulsed operation of the laser (e.g., an intracavity pulse 1-120 bounces back-and-forth between the cavity end mirrors) and produces a stream of output optical pulses 1-122 from one end mirror 1-111 which is partially transmitting.

In some cases, the analytic instrument 1-100 can be configured to receive a removable, packaged, bio-optoelectronic chip 1-140. The chip can include a plurality of reaction chambers, integrated optical components arranged to deliver optical excitation energy to the reaction chambers, and integrated photodetectors arranged to detect fluorescent emission from the reaction chambers. In some implementations, the chip 1-140 can be disposable, whereas in other implementations the chip can be reusable. When the chip is received by the instrument, it can be in electrical and optical communication with the mode-locked laser and electrical and optical communication with the analytic system 1-160.

In some embodiments, the bio-optoelectronic chip can be mounted (e.g., via a socket connection) on an electronic circuit board 1-130, such as a printed circuit board (PCB) that can include additional instrument electronics. For example, the PCB 1-130 can include circuitry configured to provide electrical power, one or more clock signals, and control signals to the bio-optoelectronic chip 1-140, and signal-processing circuitry arranged to receive signals representative of fluorescent emission detected from the reaction chambers. Data returned from the bio-optoelectronic chip can be processed in part or entirely by the instrument, although data may be transmitted via a network connection to one or more remote data processors, in some implementations. The PCB 1-130 can also include circuitry configured to receive feedback signals from the chip relating to optical coupling and power levels of the optical pulses 1-122 coupled into waveguides of the bio-optoelectronic chip 1-140. The feedback signals may be provided to one or both of the laser module 1-108 and optical system 1-115 to control one or more parameters of the output beam of optical pulses 1-122. In some cases, the PCB 1-130 can provide or route power to the laser module 1-108 for operating the mode-locked laser and circuitry in the laser module.

According to some embodiments, a mode-locked laser 1-110 can comprise a gain medium 1-105 (which can be solid-state material in some embodiments), an output coupler 1-111, and a laser-cavity end mirror 1-119. The mode-locked laser's optical cavity can be bound by the output coupler 1-111 and end mirror 1-119. An optical axis 1-125 of the laser cavity can have one or more folds (turns) to increase the length of the laser cavity. In some embodiments, there can be additional optical elements (not shown in FIG. 1-1B) in the laser cavity for beam shaping, wavelength selection, and/or pulse forming. In some cases, the end mirror 1-119 comprises a saturable-absorber mirror (SAM) that induces passive mode locking of longitudinal cavity modes and results in pulsed operation of the laser 1-110. The laser module 1-108 can further include a pump source (e.g., a laser diode, not shown in FIG. 1-1B) for exciting the gain medium.

When the laser 1-110 is mode locked, an intracavity pulse 1-120 can circulate between the end mirror 1-119 and the output coupler 1-111, and a portion of the intracavity pulse can be transmitted through the output coupler 1-111 as an output pulse 1-122. Accordingly, a train of output pulses 1-122, as depicted in the graph of FIG. 1-2, can be detected at the output coupler as the intracavity pulse 1-120 bounces back-and-forth between the output coupler 1-111 and end mirror 1-119 in the laser cavity.

Figures 1, 2:
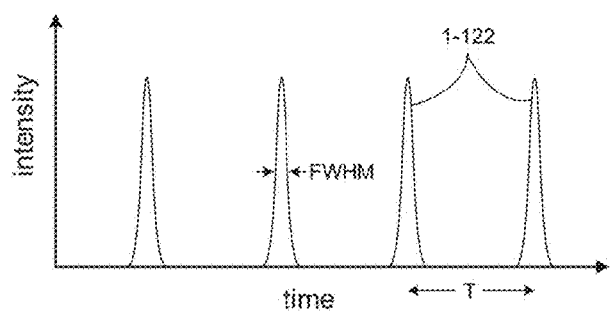

FIG. 1-2 depicts temporal intensity profiles of the output pulses 1-122. In some embodiments, the peak intensity values of the emitted pulses may be approximately equal, and the profiles may have a Gaussian temporal profile, though other profiles such as a $\text{sech}^2$ profile may be possible. In some cases, the pulses may not have symmetric temporal profiles and may have other temporal shapes. The duration of each pulse may be characterized by a full-width-half-maximum (FWHM) value, as indicated in FIG. 1-2. According to some embodiments of a mode-locked laser, ultrashort optical pulses can have FWHM values less than 100 picoseconds (ps). In some cases, the FWHM values can be between approximately 5 ps and approximately 30 ps.

The output pulses 1-122 can be separated by regular intervals T. For example, T can be determined by a round-trip travel time between the output coupler 1-111 and cavity end mirror 1-119. According to some embodiments, the pulse-separation interval T can be between about 1 ns and about 30 ns. In some cases, the pulse-separation interval T can be between about 5 ns and about 20 ns, corresponding to a laser-cavity length (an approximate length of the optical axis 1-125 within the laser cavity) between about 0.7 meter and about 3 meters. In embodiments, the pulse-separation interval corresponds to a round trip travel time in the laser cavity, so that a cavity length of 3 meters (round-trip distance of 6 meters) provides a pulse-separation interval T of approximately 20 ns.

According to some embodiments, a desired pulse-separation interval T and laser-cavity length can be determined by a combination of the number of reaction chambers on the chip 1-140, fluorescent emission characteristics, and the speed of data-handling circuitry for reading data from the bio-optoelectronic chip 1-140. The inventors have recognized and appreciated that different fluorophores can be distinguished by their different fluorescent decay rates or characteristic lifetimes. Accordingly, there needs to be a sufficient pulse-separation interval T to collect adequate statistics for the selected fluorophores to distinguish between their different decay rates. Additionally, if the pulse-separation interval T is too short, the data handling circuitry cannot keep up with the large amount of data being collected by the large number of reaction chambers. The inventors have recognized and appreciated that a pulse-separation interval T between about 5 ns and about 20 ns is suitable for fluorophores that have decay rates up to about 2 ns and for handling data from between about 60,000 and 8,000,000 reaction chambers.

According to some implementations, a beam-steering module 1-150 can receive output pulses from the mode-locked laser module 1-108 and be configured to adjust at least the position and incident angles of the optical pulses onto an optical coupler of the bio-optoelectronic chip 1-140. In some cases, the output pulses from the mode-locked laser module can be operated on by a beam-steering module to additionally or alternatively change a beam shape and/or beam rotation at an optical coupler on the bio-optoelectronic chip 1-140. In some implementations, the beam-steering module 1-150 can further provide focusing and/or polarization adjustments of the beam of output pulses onto the optical coupler. One example of a beam-steering module is described in U.S. patent application Ser. No. 15/161,088 titled "Pulsed Laser and Bioanalytic System," filed May 20, 2016, which is incorporated herein by reference. Another example of a beam-steering module is described in a separate U.S. patent application No. 62/435,679, filed Dec. 16, 2016 and titled "Compact Beam Shaping and Steering Assembly," which is incorporated herein by reference.

Figures 1, 2, 3:
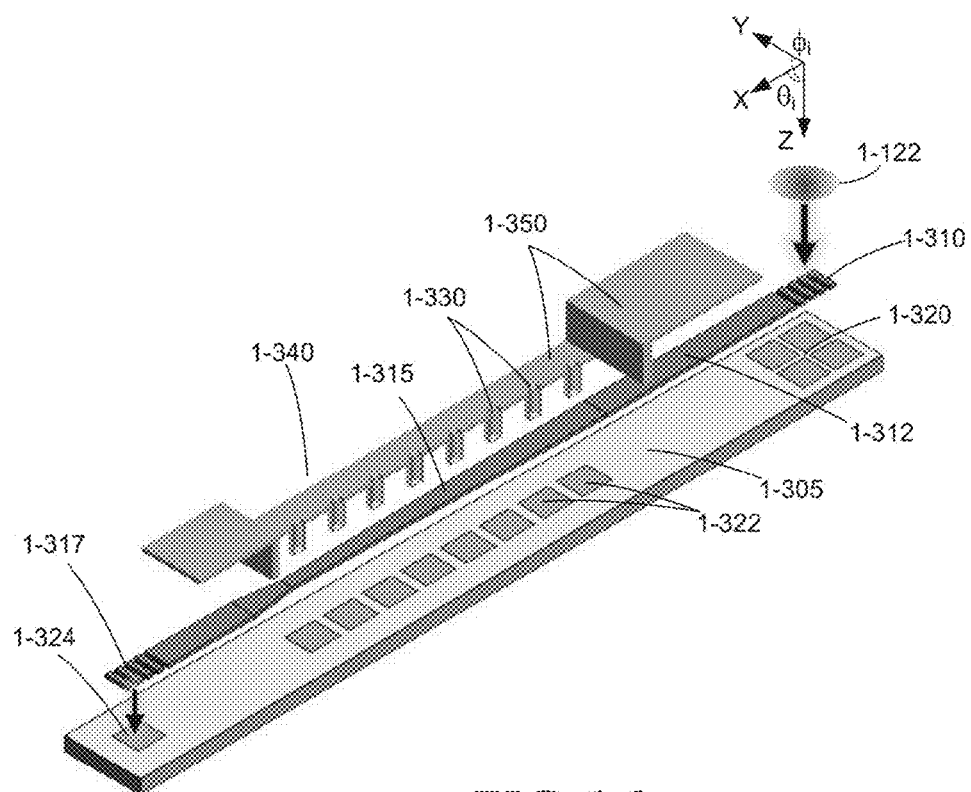

Referring to FIG. 1-3, the output pulses 1-122 from a mode-locked laser module can be coupled into one or more optical waveguides 1-312 on the bio-optoelectronic chip. In some embodiments, the optical pulses can be coupled to one or more waveguides via a grating coupler 1-310, though coupling to an end of one or more optical waveguides on the bio-optoelectronic chip can be used in some embodiments. According to some embodiments, a quad detector 1-320 can be located on a semiconductor substrate 1-305 (e.g., a silicon substrate) for aiding in alignment of the beam of optical pulses 1-122 to a grating coupler 1-310. The one or more waveguides 1-312 and reaction chambers 1-330 can be integrated on the same semiconductor substrate with intervening dielectric layers (e.g., silicon dioxide layers) between the substrate, waveguide, reaction chambers, and photodetectors 1-322.

Each waveguide 1-312 can include a tapered portion 1-315 below the reaction chambers 1-330 to equalize optical power coupled to the reaction chambers along the waveguide. The reducing taper can force more optical energy outside the waveguide's core, increasing coupling to the reaction chambers and compensating for optical losses along the waveguide, including losses for light coupling into the reaction chambers. A second grating coupler 1-317 can be located at an end of each waveguide to direct optical energy to an integrated photodiode 1-324. The integrated photodiode can detect an amount of power coupled down a waveguide and provide a detected signal to feedback circuitry that controls the beam-steering module 1-150, for example.

The reaction chambers 1-330 can be aligned with the tapered portion 1-315 of the waveguide and recessed in a tub 1-340. There can be time-binning photodetectors 1-322 located on the semiconductor substrate 1-305 for each reaction chamber 1-330. A metal coating and/or multilayer coating 1-350 can be formed around the reaction chambers and above the waveguide to prevent optical excitation of fluorophores that are not in the reaction chambers (e.g., dispersed in a solution above the reaction chambers). The metal coating and/or multilayer coating 1-350 may be raised beyond edges of the tub 1-340 to reduce absorptive losses of the optical energy in the waveguide 1-312 at the input and output ends of each waveguide.

There can be a plurality of rows of waveguides, reaction chambers, and time-binning photodetectors on the bio-optoelectronic chip 1-140. For example, there can be 128 rows, each having 512 reaction chambers, for a total of 65,536 reaction chambers in some implementations. Other implementations may include fewer or more reaction chambers, and may include other layout configurations. Optical power from the mode-locked laser 1-110 can be distributed to the multiple waveguides via one or more star couplers or multi-mode interference couplers, or by any other means, located between an optical coupler to the chip 1-140 and the plurality of waveguides.

FIG. 1-4 illustrates optical energy coupling from an optical pulse 1-122 within a waveguide 1-315 to a reaction chamber 1-330. The drawing has been produced from an electromagnetic field simulation of the optical wave that accounts for waveguide dimensions, reaction chamber dimensions, the different materials' optical properties, and the distance of the waveguide 1-315 from the reaction chamber 1-330. The waveguide can be formed from silicon nitride in a surrounding medium 1-410 of silicon dioxide, for example. The waveguide, surrounding medium, and reaction chamber can be formed by microfabrication processes described in U.S. application Ser. No. 14/821,688, filed Aug. 7, 2015, titled "Integrated Device for Probing, Detecting and Analyzing Molecules". According to some embodiments, an evanescent optical field 1-420 couples optical energy transported by the waveguide to the reaction chamber 1-330.

A non-limiting example of a biological reaction taking place in a reaction chamber 1-330 is depicted in FIG. 1-5. In this example, sequential incorporation of nucleotides or nucleotide analogs into a growing strand that is complementary to a target nucleic acid is taking place in the reaction chamber. The sequential incorporation can be detected to sequence DNA. The reaction chamber can have a depth between about 150 nm and about 250 nm and a diameter between about 80 nm and about 160 nm. A metallization layer 1-540 (e.g., a metallization for an electrical reference potential) can be patterned above the photodetector to provide an aperture that blocks stray light from adjacent reaction chambers and other unwanted light sources. According to some embodiments, polymerase 1-520 can be located within the reaction chamber 1-330 (e.g., attached to a base of the chamber). The polymerase can take up a target nucleic acid 1-510 (e.g., a portion of nucleic acid derived from DNA), and sequence a growing strand of complementary nucleic acid to produce a growing strand of DNA 1-512. Nucleotides or nucleotide analogs labeled with different fluorophores can be dispersed in a solution above and within the reaction chamber.

When a labeled nucleotide or nucleotide analog 1-610 is incorporated into a growing strand of complementary nucleic acid, as depicted in FIG. 1-6, one or more attached fluorophores 1-630 can be repeatedly excited by pulses of optical energy coupled into the reaction chamber 1-330 from the waveguide 1-315. In some embodiments, the fluorophore or fluorophores 1-630 can be attached to one or more nucleotides or nucleotide analogs 1-610 with any suitable linker 1-620. An incorporation event may last for a period of time up to about 100 ms. During this time, pulses of fluorescent emission resulting from excitation of the fluorophore(s) by pulses from the mode-locked laser can be detected with a time-binning photodetector 1-322. In some embodiments, there can be one or more additional integrated devices 1-323 at each pixel for signal handling (e.g., amplification, read-out, routing, etc.). According to some embodiments, each pixel can include a single or multilayer optical filter 1-530 that passes fluorescent emission and reduces transmission of radiation from the excitation pulse. Some implementations may not use the optical filter 1-530. By attaching fluorophores with different emission characteristics (e.g., fluorescent decay rates, intensity, fluorescent wavelength) to the different nucleotides (A, C, G, T), detecting and distinguishing the different emission characteristics while the strand of DNA 1-512 incorporates a nucleic acid and enables determination of the genetic sequence of the growing strand of DNA.

According to some embodiments, an analytical instrument 1-100 that is configured to analyze samples based on fluorescent emission characteristics can detect differences in fluorescent lifetimes and/or intensities between different fluorescent molecules, and/or differences between lifetimes and/or intensities of the same fluorescent molecules in different environments. By way of explanation, FIG. 1-7 plots two different fluorescent emission probability curves (A and B), which can be representative of fluorescent emission from two different fluorescent molecules, for example. With reference to curve A (dashed line), after being excited by a short or ultrashort optical pulse, a probability $p_A(t)$ of a fluorescent emission from a first molecule may decay with time, as depicted. In some cases, the decrease in the probability of a photon being emitted over time can be represented by an exponential decay function $p_A(t)=P_{Ao}e^{-t/\tau_A}$, where $P_{Ao}$ is an initial emission probability and $\tau_A$ is a temporal parameter associated with the first fluorescent molecule that characterizes the emission decay probability. $\tau_A$ may be referred to as the "fluorescence lifetime," "emission lifetime," or "lifetime" of the first fluorescent molecule. In some cases, the value of $\tau_A$ can be altered by a local environment of the fluorescent molecule. Other fluorescent molecules can have different emission characteristics than that shown in curve A. For example, another fluorescent molecule can have a decay profile that differs from a single exponential decay, and its lifetime can be characterized by a half-life value or some other metric.

A second fluorescent molecule may have a decay profile that is exponential, but has a measurably different lifetime $\tau_B$, as depicted for curve B in FIG. 1-7. In the example shown, the lifetime for the second fluorescent molecule of curve B is shorter than the lifetime for curve A, and the probability of emission is higher sooner after excitation of the second molecule than for curve A. Different fluorescent molecules can have lifetimes or half-life values ranging from about 0.1 ns to about 20 ns, in some embodiments.

The inventors have recognized and appreciated that differences in fluorescent emission lifetimes can be used to discern between the presence or absence of different fluorescent molecules and/or to discern between different environments or conditions to which a fluorescent molecule is subjected. In some cases, discerning fluorescent molecules based on lifetime (rather than emission wavelength, for example) can simplify aspects of an analytical instrument 1-100. As an example, wavelength-discriminating optics (such as wavelength filters, dedicated detectors for each wavelength, dedicated pulsed optical sources at different wavelengths, and/or diffractive optics) can be reduced in number or eliminated when discerning fluorescent molecules based on lifetime. In some cases, a single pulsed optical source operating at a single characteristic wavelength can be used to excite different fluorescent molecules that emit within a same wavelength region of the optical spectrum but have measurably different lifetimes. An analytic system that uses a single pulsed optical source, rather than multiple sources operating at different wavelengths, to excite and discern different fluorescent molecules emitting in a same wavelength region can be less complex to operate and maintain, more compact, and can be manufactured at lower cost.

Although analytic systems based on fluorescent lifetime analysis can have certain benefits, the amount of information obtained by an analytic system and/or detection accuracy can be increased by allowing for additional detection techniques. For example, some analytic systems 1-160 can additionally be configured to discern one or more properties of a sample based on fluorescent wavelength and/or fluorescent intensity.

Referring again to FIG. 1-7, according to some embodiments, different fluorescent lifetimes can be distinguished with a photodetector that is configured to time-bin fluorescent emission events following excitation of a fluorescent molecule. The time binning can occur during a single charge-accumulation cycle for the photodetector. A charge-accumulation cycle is an interval between read-out events during which photo-generated carriers are accumulated in bins of the time-binning photodetector. The concept of determining fluorescent lifetime by time-binning of emission events is introduced graphically in FIG. 1-8. At time $t_e$ just prior to $t_1$, a fluorescent molecule or ensemble of fluorescent molecules of a same type (e.g., the type corresponding to curve B of FIG. 1-7) is (are) excited by a short or ultrashort optical pulse. For a large ensemble of molecules, the intensity of emission can have a time profile similar to curve B, as depicted in FIG. 1-8.

For a single molecule or a small number of molecules, however, the emission of fluorescent photons occurs according to the statistics of curve B in FIG. 1-7, for this example. A time-binning photodetector 1-322 can accumulate carriers generated from emission events into discrete time bins (three indicated in FIG. 1-8) that are temporally resolved with respect to the excitation time of the fluorescent molecule(s). When a large number of emission events are summed, carriers accumulated in the time bins can approximate the decaying intensity curve shown in FIG. 1-8, and the binned signals can be used to distinguish between different fluorescent molecules or different environments in which a fluorescent molecule is located.

Examples of a time-binning photodetector 1-322 are described in U.S. patent application Ser. No. 14/821,656, filed Aug. 7, 2015, titled "Integrated Device for Temporal Binning of Received Photons," which is incorporated herein by reference. For explanation purposes, a non-limiting embodiment of a time-binning photodetector is depicted in FIG. 1-9. A single time-binning photodetector 1-900 can comprise a photon-absorption/carrier-generation region 1-902, a carrier-travel region 1-906, and a plurality of carrier-storage bins 1-908a, 1-908b, 1-908c all formed on a semiconductor substrate. The carrier-travel region can be connected to the plurality of carrier-storage bins by carrier-transport channels 1-907. Only three carrier-storage bins are shown, but there may be more. There can be a read-out channel 1-910 connected to the carrier-storage bins. The photon-absorption/carrier-generation region 1-902, carrier-travel region 1-906, carrier-storage bins 1-908a, 1-908b, 1-908c, and read-out channel 1-910 can be formed by doping the semiconductor locally and/or forming adjacent insulating regions to provide photodetection capability and confine carriers. A time-binning photodetector 1-900 can also include a plurality of electrodes 1-920, 1-922, 1-932, 1-934, 1-936, 1-940 formed on the substrate that are configured to generate electric fields in the device for transporting carriers through the device.

In operation, fluorescent photons may be received at the photon-absorption/carrier-generation region 1-902 at different times and generate carriers. For example, at approximately time $t_1$ three fluorescent photons may generate three carrier electrons in a depletion region of the photon-absorption/carrier-generation region 1-902. An electric field in the device (due to doping and/or an externally applied bias to electrodes 1-920 and 1-922, and optionally or alternatively to 1-932, 1-934, 1-936) can move the carriers to the carrier-travel region 1-906. In the carrier-travel region, distance of travel translates to a time after excitation of the fluorescent molecules. At a later time $t_5$, another fluorescent photon may be received in the photon-absorption/carrier-generation region 1-902 and generate an additional carrier. At this time, the first three carriers have traveled to a position in the carrier-travel region 1-906 adjacent to the second storage bin 1-908*b*. At a later time $t_7$, an electrical bias can be applied between electrodes 1-932, 1-934, 1-936 and electrode 1-940 to laterally transport carriers from the carrier-travel region 1-906 to the storage bins. The first three carriers can then be transported to and retained in the first bin 1-908*a* and the later-generated carrier can be transported to and retained in the third bin 1-908*c*. In some implementations, the time intervals corresponding to each storage bin are at the sub-nanosecond time scale, though longer time scales can be used in some embodiments (e.g., in embodiments where fluorophores have longer decay times).

The process of generating and time-binning carriers after an excitation event (e.g., excitation pulse from a pulsed optical source) can occur once after a single excitation pulse or be repeated multiple times after multiple excitation pulses during a single charge-accumulation cycle for the photodetector 1-900. After charge accumulation is complete, carriers can be read out of the storage bins via the read-out channel 1-910. For example, an appropriate biasing sequence can be applied to at least electrode 1-940 and a downstream electrode (not shown) to remove carriers from the storage bins 1-908*a*, 1-908*b*, 1-908*c*.

After a number of excitation events, the accumulated signal in each electron-storage bin can be read out to provide a histogram having corresponding bins that represent the fluorescent emission decay rate, for example. Such a process is illustrated in FIG. 1-10A and FIG. 1-10B. The histogram's bins can indicate a number of photons detected during each time interval after excitation of the fluorophore(s) in a reaction chamber. In some embodiments, signals for the bins will be accumulated following a large number of excitation pulses, as depicted in FIG. 1-10A. The excitation pulses can occur at times $t_{e1}, t_{e2}, t_{e3}, \ldots t_{eN}$ which are separated by the pulse interval time T. There can be between $10^5$ and $10^7$ excitation pulses applied to the reaction chamber during an accumulation of signals in the electron-storage bins. In some embodiments, one bin (bin 0) can be configured to detect an amplitude of excitation energy delivered with each optical pulse, and be used as a reference signal (e.g., to normalize data).

In some implementations, only a single photon on average may be emitted from a fluorophore following an excitation event, as depicted in FIG. 1-10A. After a first excitation event at time $t_{e1}$, the emitted photon at time $t_{f1}$ may occur within a first time interval, so that the resulting electron signal is accumulated in the first electron-storage bin (contributes to bin 1). In a subsequent excitation event at time $t_{e2}$, the emitted photon at time $t_{f2}$ may occur within a second time interval, so that the resulting electron signal contributes to bin 2.

After a large number of excitation events and signal accumulations, the electron-storage bins of the time-binning photodetector 1-322 can be read out to provide a multi-valued signal (e.g., a histogram of two or more values, an N-dimensional vector, etc.) for a reaction chamber. The signal values for each bin can depend upon the decay rate of the fluorophore. For example and referring again to FIG. 1-8, a fluorophore having a decay curve B will have a higher ratio of signal in bin 1 to bin 2 than a fluorophore having a decay curve A. The values from the bins can be analyzed and compared against calibration values, and/or each other, to determine the particular fluorophore, which in turn identifies the nucleotide or nucleotide analog (or any other molecule or specimen of interest) linked to the fluorophore when in the reaction chamber.

To further aid in understanding the signal analysis, the accumulated, multi-bin values can be plotted as a histogram, as depicted in FIG. 1-10B for example, or can be recorded as a vector or location in N-dimensional space. Calibration runs can be performed separately to acquire calibration values for the multi-valued signals (e.g., calibration histograms) for four different fluorophores linked to the four nucleotides or nucleotide analogs. As an example, the calibration histograms may appear as depicted in FIG. 1-11A (fluorescent label associated with the T nucleotide), FIG. 1-11B (fluorescent label associated with the A nucleotide), FIG. 1-11C (fluorescent label associated with the C nucleotide), and FIG. 1-11D (fluorescent label associated with the G nucleotide). A comparison of the measured multi-valued signal (corresponding to the histogram of FIG. 1-10B) to the calibration multi-valued signals can determine the identity "T" (FIG. 1-11A) of the nucleotide or nucleotide analog being incorporated into the growing strand of DNA.

In some implementations, fluorescent intensity can be used additionally or alternatively to distinguish between different fluorophores. For example, some fluorophores may emit at significantly different intensities or have a significant difference in their probabilities of excitation (e.g., at least a difference of about 35%) even though their decay rates may be similar. By referencing binned signals (bins 1-3) to measured excitation energy bin 0, it can be possible to distinguish different fluorophores based on intensity levels.

In some embodiments, different numbers of fluorophores of the same type can be linked to different nucleotides or nucleotide analogs, so that the nucleotides can be identified based on fluorophore intensity. For example, two fluorophores can be linked to a first nucleotide (e.g., "C") or nucleotide analog and four or more fluorophores can be linked to a second nucleotide (e.g., "T") or nucleotide analog. Because of the different numbers of fluorophores, there may be different excitation and fluorophore emission probabilities associated with the different nucleotides. For example, there may be more emission events for the "T" nucleotide or nucleotide analog during a signal accumulation interval, so that the apparent intensity of the bins is significantly higher than for the "C" nucleotide or nucleotide analog.

The inventors have recognized and appreciated that distinguishing nucleotides or any other biological or chemical specimens based on fluorophore decay rates and/or fluorophore intensities enables a simplification of the optical excitation and detection systems in an analytical instrument 1-100. For example, optical excitation can be performed with a single-wavelength source (e.g., a source producing one characteristic wavelength rather than multiple sources or a source operating at multiple different characteristic wavelengths). Additionally, wavelength discriminating optics and filters may not be needed in the detection system. Also, a single photodetector can be used for each reaction chamber to detect emission from different fluorophores.

The phrase "characteristic wavelength" or "wavelength" is used to refer to a central or predominant wavelength within a limited bandwidth of radiation (e.g., a central or peak wavelength within a 20 nm bandwidth output by a pulsed optical source). In some cases, "characteristic wavelength" or "wavelength" may be used to refer to a peak wavelength within a total bandwidth of radiation output by a source.

The inventors have recognized and appreciated that fluorophores having emission wavelengths in a range between about 560 nm and about 900 nm can provide adequate amounts of fluorescence to be detected by a time-binning photodetector (which can be fabricated on a silicon wafer using CMOS processes). These fluorophores can be linked to biological molecules of interest such as nucleotides or nucleotide analogs. Fluorescent emission in this wavelength range can be detected with higher responsivity in a silicon-based photodetector than fluorescence at longer wavelengths. Additionally, fluorophores and associated linkers in this wavelength range may not interfere with incorporation of the nucleotides or nucleotide analogs into growing strands of DNA. The inventors have also recognized and appreciated that fluorophores having emission wavelengths in a range between about 560 nm and about 660 nm can be optically excited with a single-wavelength source. An example fluorophore in this range is Alexa Fluor 647, available from Thermo Fisher Scientific Inc. of Waltham, Mass. The inventors have also recognized and appreciated that excitation energy at shorter wavelengths (e.g., between about 500 nm and about 650 nm) may be required to excite fluorophores that emit at wavelengths between about 560 nm and about 900 nm. In some embodiments, the time-binning photodetectors can efficiently detect longer-wavelength emission from the samples, e.g., by incorporating other materials, such as Ge, into the photodetectors active region.

Although the prospect of sequencing DNA using an excitation source that emits a single characteristic wavelength can simplify some of the optical system, it can place technically challenging demands on the excitation source, as noted above. For example, the inventors have recognized and appreciated that optical pulses from the excitation source should extinguish quickly for the detection schemes described above, so that the excitation energy does not overwhelm or interfere with the subsequently detected fluorescent signal. In some embodiments and referring again to FIG. 1-5, there may be no wavelength filters between the waveguide 1-315 and the time-binning photodetector 1-322. To avoid interference of the excitation energy with subsequent signal collection, the excitation pulse may need to reduce in intensity by at least 50 dB within about 100 ps from the peak of the excitation pulse. In some implementations, the excitation pulse may need to reduce in intensity by at least 80 dB within about 100 ps from the peak of the excitation pulse. The inventors have recognized and appreciated that mode-locked lasers can provide such rapid turn-off characteristics. However, mode-locked lasers can be difficult to operate in a stable mode-locking state for extended periods of time. Also, because the pulse repetition rate may need to be lower than 100 MHz for data acquisition purposes, the length of a mode-locked laser cavity can become very long. Such long lengths are contrary to a compact optical source that can be incorporated into a portable, desk-top instrument. Additionally, a mode-locked laser must provide adequate energy per pulse (or high average powers) for excitation of fluorophores at wavelengths below 660 nm, so that fluorescence is detectable with integrated photodiodes for thousands or even millions of reaction chambers in parallel. The inventors have further recognized and appreciated that a beam quality of the mode-locked laser should be high (e.g., an $M^2$ value less than 1.5), so that efficient coupling can be achieved to an optical coupler and waveguides of a bio-optoelectronic chip 1-140, for example. Currently, there is no commercial mode-locked lasing system available that provides pulses at repetition rates between 50 MHz and 200 MHz, at wavelengths between 500 nm and 650 nm, at average powers between 250 mW and 1 W, in a compact module (e.g., occupying a volume of less than 0.1 ft$^3$) that could be incorporated into a portable, desk-top instrument and remain stable for extended periods of time.

III. Compact Mode-Locked Laser Module

The inventors have conceived and built a compact mode-locked laser module 1-108 (e.g., as schematically depicted in FIG. 1-1A and FIG. 1-1B) that achieves the above-described performance specifications in terms of average power, compactness, beam quality, pulse repetition rate, excitation wavelength, and turn-off speed of optical pulses. In overview and referring to FIG. 2-1, principle components of a compact mode-locked laser module 1-108, according to some embodiments, can include a laser cavity (which includes optical elements between an output coupler 1-111 that can function as a first end mirror of the laser cavity and saturable absorber mirror (SAM) 1-119 that can function as a second end mirror of the laser cavity), a formed base chassis 2-105 on which some or all of the components of the mode-locked laser 1-110 are mounted, at least one intracavity optical element 2-128 that can stabilize operation of the mode-locked laser, frequency-doubling elements 2-170, 2-164, 2-160 that can participate in converting an output from the laser to a shorter wavelength, and electrical components 2-190, 2-154, 2-182, 2-116 that monitor operational parameters of the laser and generate an electronic clock signal that is synchronized to the optical pulses produced by the laser. A pump module 2-140 can be mounted to the base chassis 2-105 and used to excite the gain medium 1-105 of the mode-locked laser.

Base Chassis and Laser Cavity

The base chassis 2-105 of a compact mode-locked laser module 1-108 may measure between about 20 cm and about 30 cm in length L, between about 10 cm and about 20 cm in height H, and has a thickness between about 10 mm and about 30 mm, according to some embodiments. In some cases, one or more of the dimensions can be up to 20% larger. According to some embodiments, a volume occupied by the compact, mode-locked laser module 1-108 can be about 30 cm×18 cm×3 cm or approximately 0.07 ft$^3$. According to some implementations, the overall shape or form factor of the mode-locked laser module 1-108 is a slab having a length L longer than a height H and a thickness much less than either the length or height, occupying a volume less than 0.1 cubic foot and weighing less than, or has a weight of, approximately, 2 kilograms. In some cases, the weight of the module 1-108 is between 1 kilogram and 2 kilograms.

In some embodiments, the base chassis 2-105 can be formed from aluminum, titanium, an alloy of aluminum, or an alloy of titanium. Other materials can be used in other embodiments. In some implementations, the base chassis 2-105 can include a plurality of cavities 2-102 that are machined or otherwise formed (e.g., by casting or assembly) into the base chassis. In some embodiments, 12.5 mm-diameter optical components (or smaller) can be used to construct the mode-locked laser 1-110 and be partially or fully recessed into the cavities 2-102 of the base chassis 2-105, so that a cover (not shown) can be placed over the cavities 2-102 to protect the components within the cavities from outside environmental factors and contaminants. In some embodiments, a cover can be placed over the cavities 2-102 to hermetically seal one or more of the cavities.

Between the cavities 2-102, there can be ribs 2-107 formed in the base chassis 2-105. In some of the ribs, there can be holes or openings (not visible) that allow the intracavity laser beam to pass through the ribs to adjacent cavities. According to some embodiments, there can be one or more diagonal ribs 2-107 that runs at an angle with respect to an edge of the base chassis 2-105. For example, a diagonal rib 2-107 can run in a corner-to-corner direction across the base chassis 2-105. The inventors have found that such a diagonal rib 2-107 can increase the torsional stiffness of the base chassis 2-105 by a factor of three compared to having no diagonal ribs. An increased torsional stiffness can help prevent instability of laser operation and improve the module's resistance to perturbing forces acting on the base chassis 2-105. In some cases, at least portions of the ribs can extend from a bottom of a cavity to a top surface of the base chassis 2-105, so that one or more covers (not shown) for the laser module 1-108 can attach to the ribs. In this regard, any suitable cover may be used including, but not limited to, a stiff metal cover (e.g., a metal having a thickness greater than approximately 1 mm), a stiff polymer cover (e.g., a polymer having a thickness greater than approximately 2 mm), or a flexible material (metal or polymer) that can be sealed to the base chassis 2-105, or held against the base chassis 2-105 with a supporting piece (e.g., a metal frame). In some cases, a covering material comprises Tyvek® (approximately 0.25 mm thick) that is held against the base chassis with a metal frame (approximately 1.5 mm thick).

In some implementations, one or more mounting features 2-103 can be located at one or more ribs 2-107. The mounting features 2-103 can be used to mount the compact laser module 1-108 to an instrument or other platform. In some cases, the mounting features provide kinematic mounting, so that each laser module 1-108, or the same laser module, reproducibly mounts in nearly the same location and alignment (e.g., to within ±100 microns). The mounting features 2-103 may comprise holes that are tapped or are clear. The holes can be countersunk or counterbored. For kinematic mounting, there can be three mounting features 2-103 for which the bottom surfaces (not shown in FIG. 2-1) comprise a conical contacting surface or ring contact for a first mounting feature, a wedged contacting surface or two-point contacting surface for a second mounting feature, and a flat surface or single-point contact for a third mounting feature. Alternatively, two countersunk holes at the mounting features 2-103 may be used to align the base chassis 2-105 to a receiving support structure.

A mode-locked laser 1-110 of the laser module 1-108 can comprise an output coupler 1-111 at an output end of the laser's cavity, a gain medium 1-105, and a saturable absorber mirror (SAM) 1-119 at an opposite end of the laser cavity. There can be multiple mirrors 2-116, 2-117, 2-120, 2-121, 2-122, 2-123, 2-124, 2-125 within the laser cavity to fold the optical axis 1-125 of the laser and extend the length of the laser cavity to achieve a desired pulse repetition rate or pulse separation interval T. There can also be beam-shaping optics (e.g. lenses and/or curved mirrors) within the laser cavity to alter a size and/or shape of the intracavity laser beam.

Example optical components for a mode-locked laser that operates at a lasing wavelength of 1064 nm will now be described. It will be appreciated that embodiments of invention are not limited to only the described optical components. Fewer or more optical components may be used in some implementations (e.g., adding or removing mirrors to change the pulse repetition rate), and the optical coatings on components can be different for lasers that lase at different wavelengths.

The gain medium 1-105 can comprise a neodymium-doped material that is mounted in a thermally-conductive mount (e.g., an aluminum or copper block or other thermally-conductive material) which dissipates heat into the base chassis 2-105. The inventors have recognized that when the mode-locked laser operates at high average powers (e.g., over 300 mW) thermal lensing effects in the gain medium 1-105 occur. In some cases, such thermal lensing could destabilize operation of the laser. To improve heat transfer from the gain medium to the thermally-conductive mount, the gain medium 1-105 can be wrapped in indium foil or any other suitable material that improves heat transfer to the thermally-conductive mount. In some cases, silver epoxy or any other suitable thermally-conductive adhesive can be used to secure the gain crystal to the thermal mount. In some cases, the gain medium 1-105 and thermally-conductive mount can be mounted on a thermo-electric cooler (TEC), which can sink heat into the base chassis 2-105. The TEC or other active cooling techniques such as liquid cooling can provide active temperature control of the gain medium 1-105 and reduce thermal lensing effects.

Surprisingly, the inventors found that a laser cavity configuration, for which analytic modeling showed an unstable resonator, could lase stably in the laboratory. To explain the lasing, the model had to be changed to include an amount of thermal lensing in the gain medium greater than about one diopter. According to some embodiments, a laser cavity configuration could be obtained in which large amounts of thermal lensing could be tolerated. As a result, active cooling of the gain medium can be removed from the mode-locked laser module 1-110. In embodiments, the gain medium 1-105 can be disposed in a thermally-conductive mount that contacts the base chassis so as to conduct heat passively from the gain medium 1-105 to the base chassis 2-105.

Elimination of active cooling of the gain medium 1-105 can reduce cost and complexity of the laser. The inventors have observed that active temperature control of the gain medium need not be used for the mode-locked laser 1-110 of the present embodiments, even when optical pumping powers of up to 10 Watts are used to pump the gain medium. Surprisingly, the mode-locked laser 1-110 remains stably mode locked over this range of pump power, even though the associated thermal lensing effects (positive lensing) can change a thermally-induced focal length of the gain medium from 0 to approximately 15 diopters over the pump power range. For thermal lensing in excess of 15 diopters, the laser cavity can become an unstable resonator that may not support mode-locked operation nor continuous-wave operation. The stability of mode locking over such a large range of thermal lensing in the gain medium is due in part to the selection and arrangement of optical components for the mode-locked laser 1-110. According to one embodiment, stability and improved performance of mode-locked operation depends critically on having an amount of thermal lensing occur in the gain medium. In embodiments, stable mode-locked operation of the mode-locked laser 1-110 can be obtained for an amount of thermal lensing between one diopter and 15 diopters of positive lensing effect. Even though the thermal lensing may vary over this range, no mechanical adjustments need be made to the laser cavity to maintain stable mode locking. Improved performance of the mode-locked laser can be obtained when the amount of thermal lensing in the gain medium 1-105 is between 8 diopters and 12 diopters of positive thermal lensing. For continuous-wave operation, there can be between 0 diopter and at least 15 diopters of positive thermal lensing. An amount of thermal lensing (greater than approximately 4 diopters) can be measured by passing a continuous wave laser probe beam (e.g., from a helium neon laser or laser diode) through the gain medium 1-105 (e.g., at an angle) and measuring a relative displacement of the probe beam at a distance from the gain medium between "pump-beam-on" and "pump-beam-off" states. A pump-beam-on state is when the laser diode pump beam is on and exciting the gain medium 1-105 for mode-locked lasing of the laser 1-110. Values below 4 diopters can be difficult to measure accurately, since the relative displacement becomes small.

Absorption of an optical pump beam in the gain medium 1-105 can cause thermal lensing in the gain medium. In embodiments, an amount of thermal lensing in the gain medium can be changed by changing an amount of power in an optical pump beam applied to the gain medium 1-105 (e.g., changing an amount of power from pump module 2-140). Additionally or alternatively, an amount of thermal lensing in the gain medium can be changed by tuning an optical wavelength of an optical pump beam used to excite the gain medium 1-105. Tuning of the optical pump beam's wavelength can be performed, for example, by tuning a temperature of a laser diode in the pump module 2-140. Tuning a pump beam's wavelength can change an amount of absorption of the optical pump beam in the gain medium 1-105.

In some implementations, the gain medium 1-105 can comprise neodymium vanadate (e.g., $Nd^{3+}$:$YVO_4$), which can provide lasing at 1064 nm. Other solid state crystals such as, but not limited to, Nd:YAG, Nd:YLF, and Cr:Forsterite can be used in other embodiments. In some implementations, a neodymium vanadate gain medium 1-105 can be used to provide lasing at 1342 nm alternatively or additionally, provided optical components in the cavity are designed and coated for lasing at this wavelength. The gain medium can have a length between 3 mm and 11 mm, in some cases. In some embodiments, the length of the gain medium can be between 5 mm and 9 mm. The neodymium dopant level (atomic %) can be between 0.10% and 1%, in some cases. In some implementations, the dopant level can be between 0.10% and 0.50%. In some implementations, the dopant level can be between 0.24% and 0.30%. According to some embodiments, the crystal length can be approximately 7 mm and the dopant level can be approximately 0.27%. The inventors have found that doping levels (atomic %) appreciably higher than 0.3% for lengths of approximately 7 mm can destabilize operation of the laser at higher operating powers (e.g., induce lasing in higher-order spatial modes, or destabilize or terminate mode locking), which may undesirably require readjusting intracavity components. For example, with 1% doping, mode locking terminated above a certain pump power level, and intracavity optical elements had to be readjusted to regain mode locking. The transverse dimension or dimensions of the gain medium 1-105 can be any suitable value (e.g., between 1 mm and 4 mm). The gain medium can be in the form of a cylindrical rod, rectangular bar, or any other shape.

End facets of the gain medium 1-105 can be anti-reflection coated for the lasing wavelength $\lambda_1$ (which can be about 1064 nm for neodymium vanadate) and for the pump wavelength $\lambda_p$ (which can be about 808 nm for neodymium vanadate), according to some embodiments. In some embodiments, one end facet of the gain medium can be coated with an output coupler coating, so that the end facet acts as an end mirror of the laser cavity and a separate output coupler 1-111 need not be used.

The gain medium 1-105 can be mounted in a non-adjustable mount (a mount that provides no fine angular or positional adjustment) in an orientation where end facets of the gain medium have normal vectors oriented at an angle between about 1 degree and about 3 degrees to the optical axis 1-125 of the laser cavity. For example, a thermally-conductive mount for the gain medium can include a recess in which the gain medium 1-105 is placed. The recess can align the gain medium to the thermally-conductive mount. The thermally-conductive mount can then register to features on the base chassis 2-105 (e.g., any one or combination of machined surfaces, pins, screw holes) to align the gain medium at an angle to the optical axis 1-125 of the laser cavity. According to some implementations, the gain medium 1-105 can be cut and oriented in its mount so that it aligns with a favored polarization intended for lasing. For example, the gain medium 1-105 can be oriented to lase with a linear polarization parallel to the Y axis in FIG. 2-1.

An example of a thermally-conductive mount 3-100 for the gain medium is depicted in FIG. 3-1A, according to some embodiments. The depicted mount 3-100 is designed for a gain medium having a square cross section, but the mount 3-100 can be designed for other cross-sections such as rectangular, round, oval, or polygonal. According to some embodiments, a thermally-conductive mount 3-100 for a gain medium can comprise a first portion 3-120 and a second portion 3-122 that are configured to be joined together in a clamping arrangement. For example the first portion 3-120 and second portion 3-122 can contain through-holes 3-140 for screws (not shown) that allow the two portions to be fastened to and placed in thermal contact with the base chassis 2-105. Screws placed in the through-holes 3-140 can align the mount 3-100 to the base chassis 2-105 and clamp the gain medium 1-105. The first portion 3-120 and the second portion 3-122 can be formed from a high-thermal-conducting material such as copper or aluminum, although other materials can be used in other embodiments. The first and second portions can have interior faces 3-115 that are arranged to be placed in thermal contact with the gain medium 1-105. According to some embodiments, there can be trenches or openings 3-130 located at regions of the mount where corners of the gain medium 1-105 may be located (e.g., when the gain medium 1-105 is mounted in the mounting structure 3-100). The trenches or openings can extend between about 0.5 mm and about 3 mm on either side of a corner location of the gain medium 1-105. The inventors have found that the openings at the corners in the mount 3-100 for the gain medium 1-105 can alleviate thermal and mechanical stress that may otherwise crack the gain medium 1-105 and/or adversely affect the optical mode profile of the laser.

Another example of a thermally-conductive mount 3-101 for the gain medium 1-105 is depicted in FIG. 3-1B. The mount 3-101 can include a first portion 3-121 and a second portion 2-123. The first portion 3-121 can include a recess 3-131 machined into the first portion that is slightly oversized compared to the gain medium 1-105 (not shown). In some implementations, a gain medium (e.g., neodymium-vanadate crystal) can be adhered into the recess 3-131 to interior surfaces 3-116 of the recess with a thermally-conductive adhesive or gel. The oversized recess 3-131 can accommodate a thin layer (e.g., less than 400 microns thick) of adhesive or gel that can avoid mechanical stresses from the mount 3-101 that would act on the gain medium 1-105. The gain medium can also be adhered to a surface of the second portion 3-123 when secured in the laser cavity 1-110. In some embodiments, the second portion 3-123 can be formed in the base chassis 2-105 (e.g., a platform or other supporting structure machined into the base chassis 2-105). The first portion 3-121 can be connected to the second portion 3-123 with screws, for example.

According to some embodiments, an output coupler 1-111 for a compact mode-locked laser can be a high-quality laser optic having a surface quality of 10-5 (scratch and dig) and a wavefront error of at most $\lambda/10$. One surface of the output coupler 1-111 can be coated with a multi-layer dielectric to provide a reflectivity having a value between about 75% and about 95% for the lasing wavelength $\lambda_1$ and allow (with minimal reflectance) transmission of a pump wavelength $\lambda_p$ that is used to excite the gain medium 1-105. In some embodiments, the lasing wavelength may be about 1064 nm and the pump wavelength may be about 808 nm, though other wavelengths can be used in other embodiments. In some implementations, the reflectivity of the output coupler at the lasing wavelength is between 82% and 88%. The inventors have discovered that an output coupler within this range of reflectivity provides a desired amount of output power with stable operation of the laser and provides appropriate amounts of fluence on the saturable absorber mirror 1-119 over an operating range of the laser.

A second surface of the output coupler 1-111 (toward the laser output) can be coated with an antireflection coating for both the pump wavelength and lasing wavelength, and can be oriented at an angle (e.g., between about 1 degree and about 4 degrees) with respect to the reflective surface of the output coupler. The inventors have found that a small amount of reflection of the lasing wavelength from the output (transmitting) surface of the output coupler 1-111 can appreciably and adversely broaden pulses from the mode-locked laser. According to some embodiments, the coatings on the output coupler are dichroic, so as to transmit with negligible reflection the pump wavelength $\lambda_p$.

According to some embodiments, the output coupler 1-111 can be mounted in a two-axis adjustable mount that provides angular adjustment with respect to the optical axis 1-125 about two orthogonal axes (e.g., about the Y and X axes in FIG. 2-1). In some embodiments, the output coupler 1-111 can be mounted in a non-adjustable mount which can be integrated into the base chassis 2-105. A non-adjustable mount reduces cost and complexity of the compact laser. In yet other embodiments, the output coupler 1-111 can be formed as a multilayer optical coating on an end-face of the gain medium 1-105 instead of a separate optical component comprising a transparent substrate and one or more optical coatings.

Figures 2B, 3:
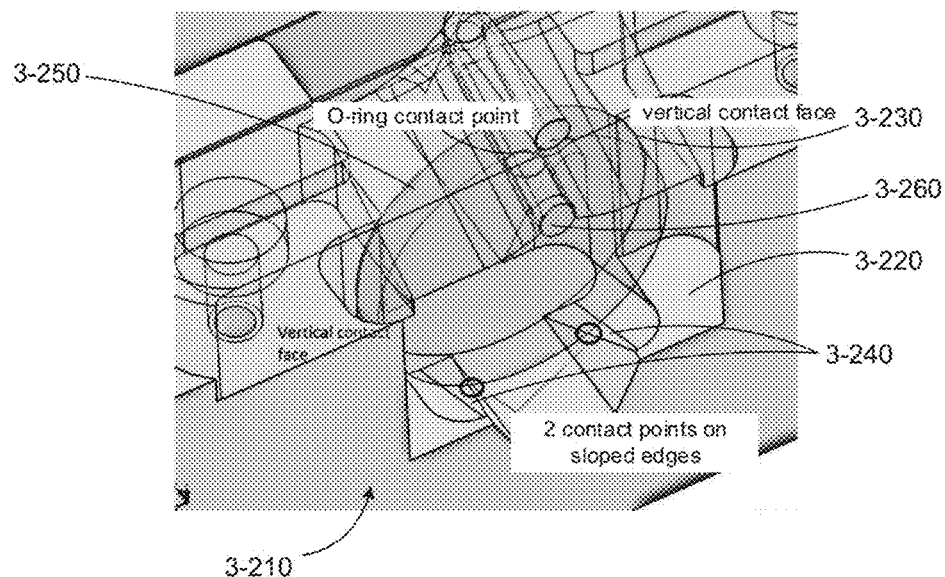
Figure 3:
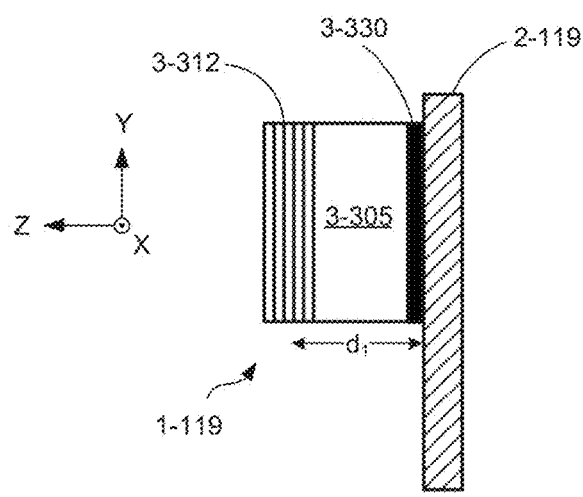
Figures 3, 4:
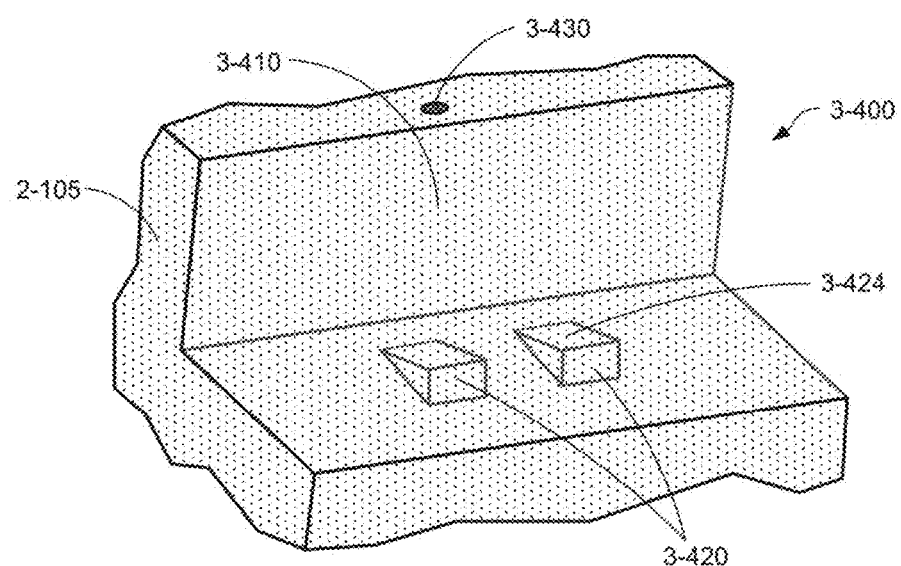
Figures 3, 4, 5, 5A:
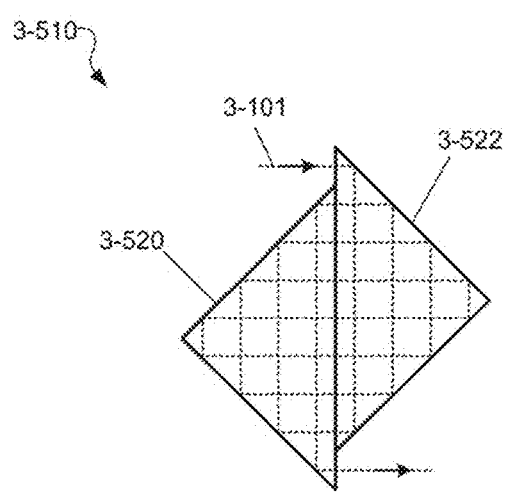
Figures 3, 4, 5, 6, 6A:
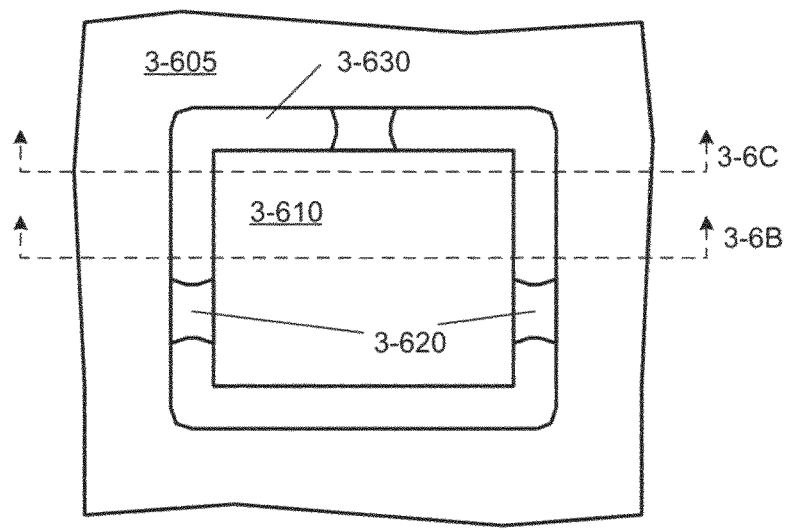
Figures 3, 4, 5, 6, 6B:
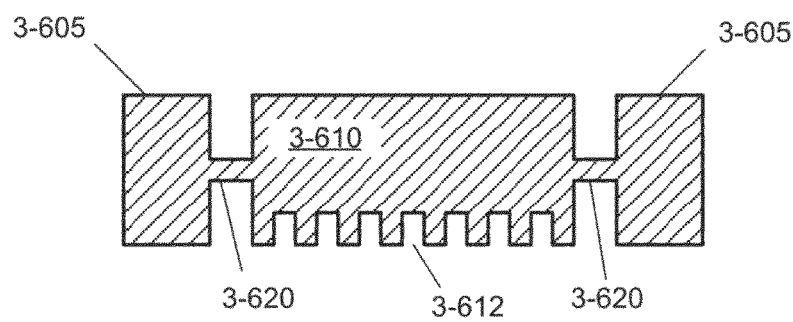
Figures 3, 4, 5, 6, 6C:
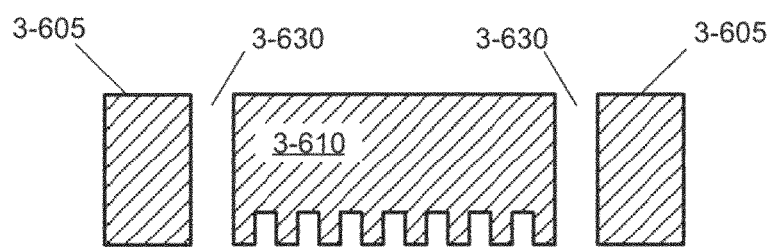
Figures 1, 4:
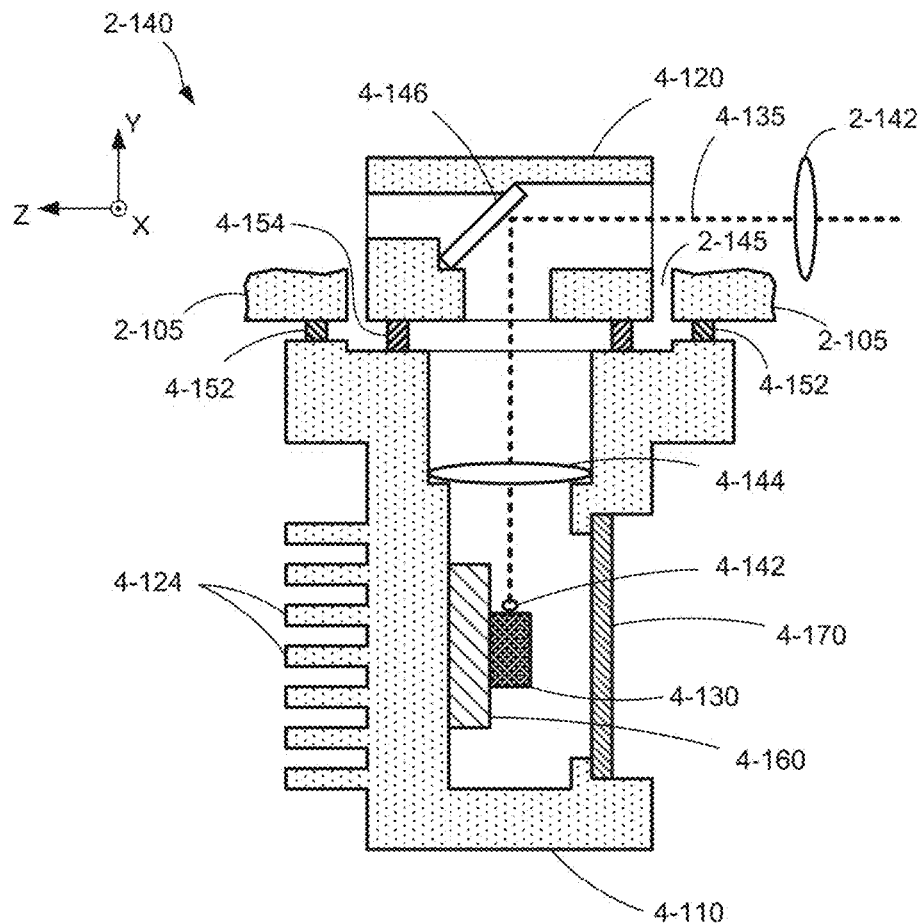
Figures 1, 5:
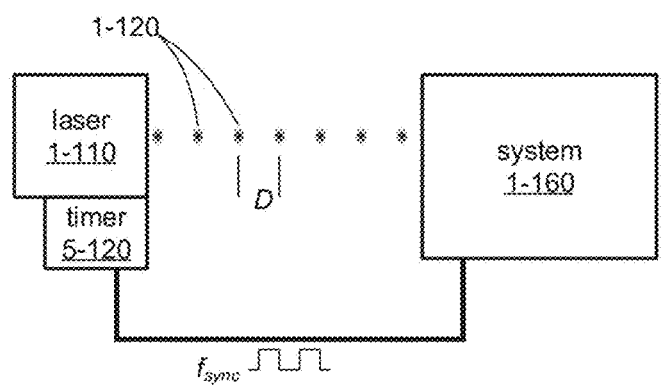
Figures 2A, 4:
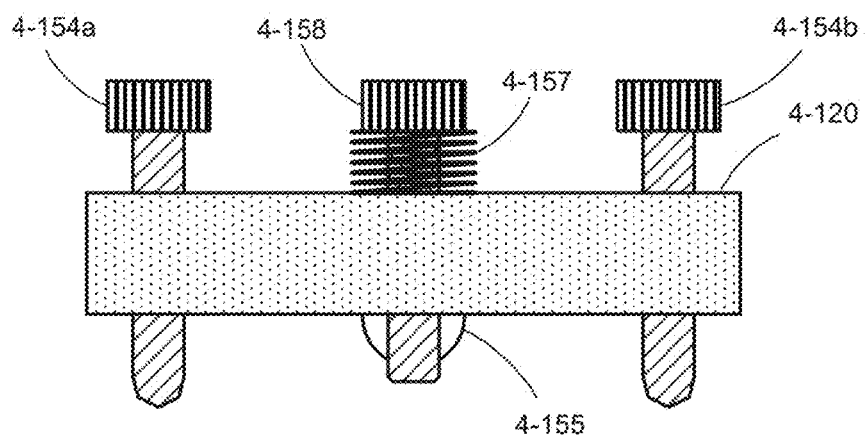
Figures 2B, 4:
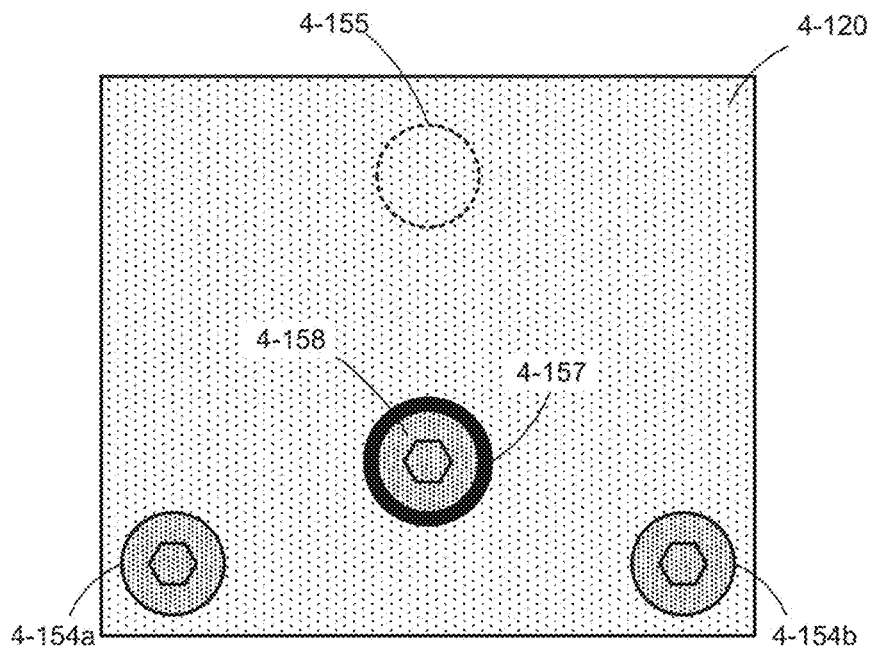
Figures 2, 5:
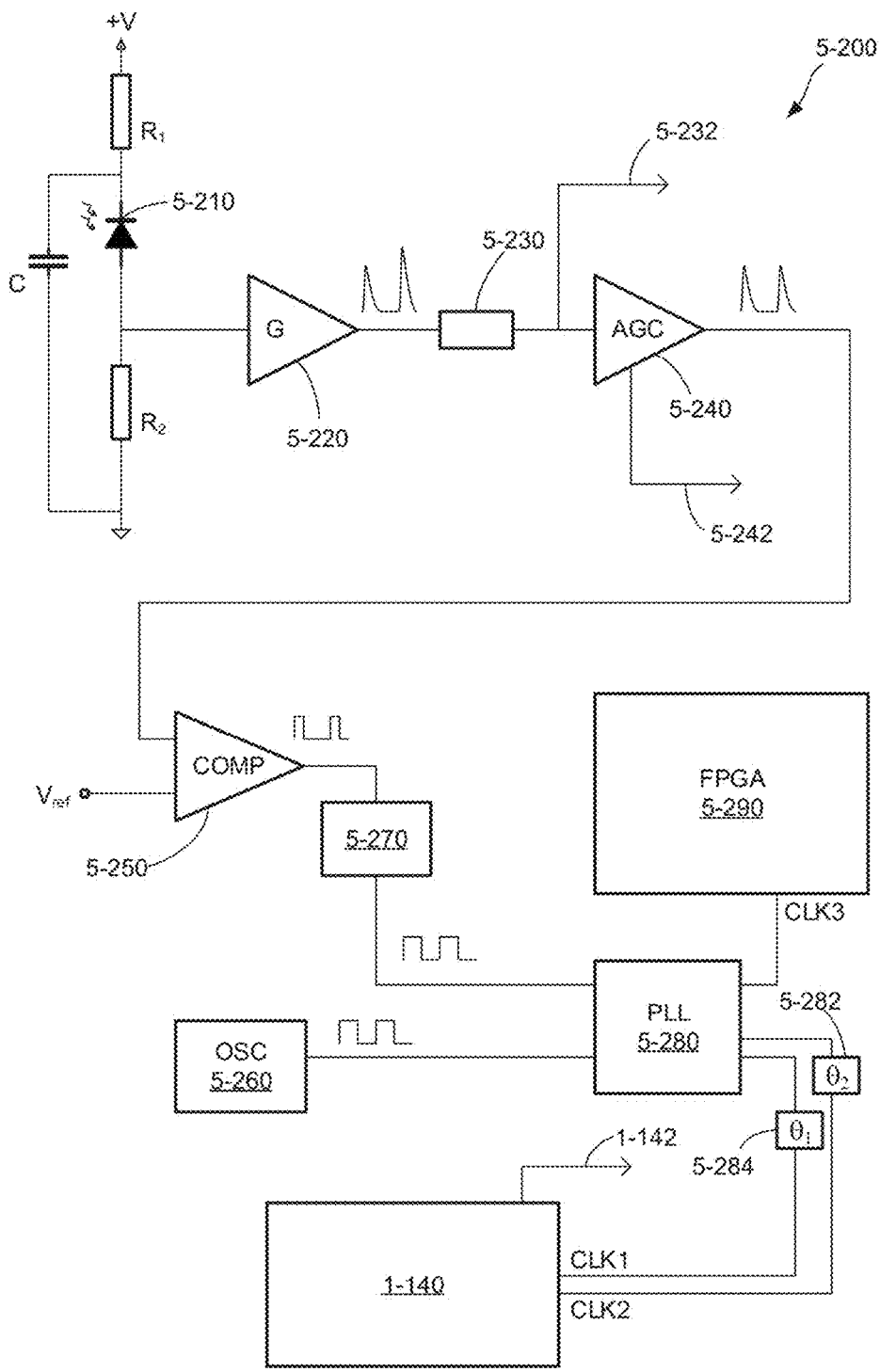
Figures 3, 5:
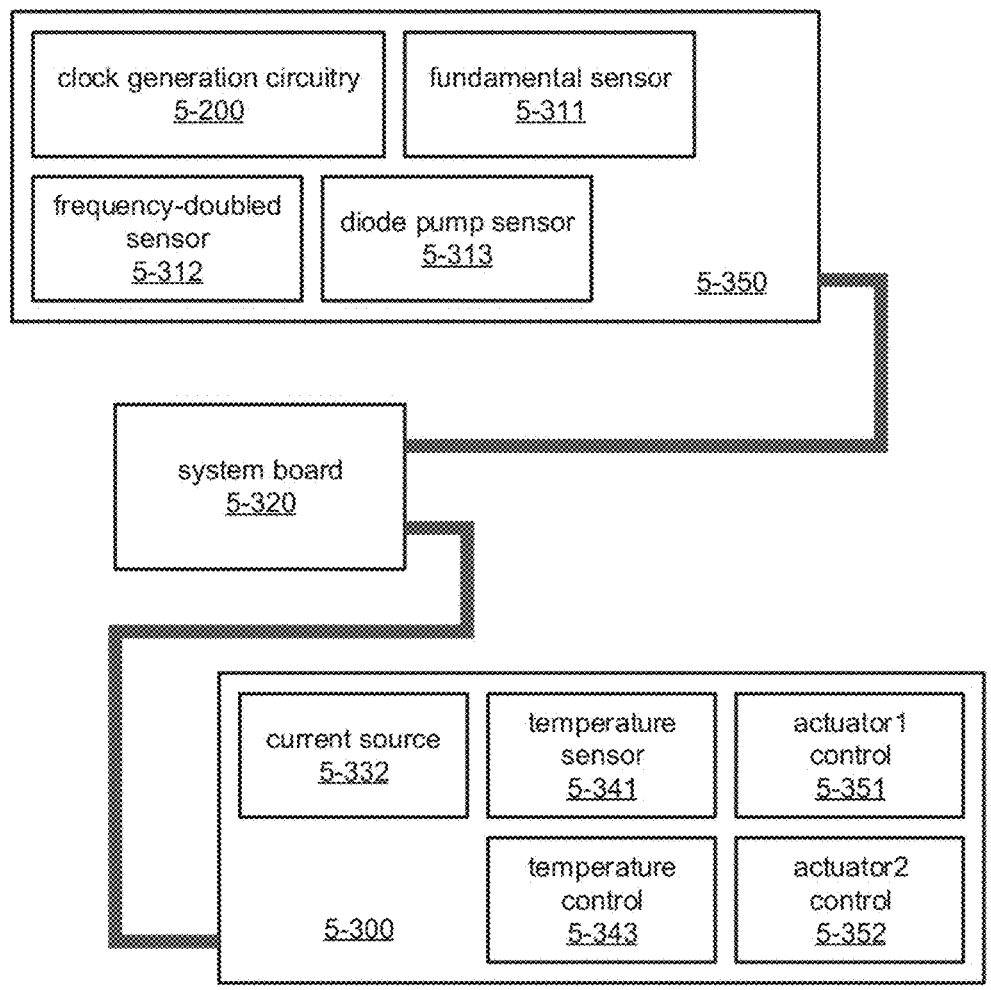

One example of an integrated non-adjustable mount for an output coupler or other optical component is depicted in FIG. 3-2A and FIG. 3-2B. The integrated mount can self-align the optical component to the optical axis 1-125 of the laser. An integrated optical mount 3-210 as shown in FIG. 3-2A can comprise an axial trench 3-220 machined or otherwise formed into the base chassis 2-105 of a mode-locked laser 1-110. The axial trench 3-220 can extend in a direction parallel to an optical axis of the mode-locked laser cavity. An integrated optical mount 3-210 can further comprise coplanar surfaces 3-230 formed approximately transverse to the axial trench 3-220. The coplanar surfaces can be formed by machining or milling a short trench in a direction that is approximately orthogonal to the axial trench 3-220. In some cases, the coplanar surfaces 3-230 can be oriented at a small angle, so that back reflections from a mounted optic will be displaced from the optical axis of the laser cavity. At the base of the axial trench 3-220 there can be sloped surfaces 3-240 (only one is visible in FIG. 3-2A). The sloped surfaces 3-240 can be machined, milled, or otherwise formed near the base of the axial trench and located on opposite sides of the axial trench 3-220. The sloped surfaces 3-240 can be inclined in a direction toward the coplanar surfaces 3-230, and provide support for an optic mounted thereon.

An optical component (optic) 3-250 for a mode-locked laser, for example, can be supported by the integrated optical mount 3-210, as depicted in FIG. 3-2B. The optic 3-250 can comprise a cavity mirror, a lens within the laser cavity, or the gain medium 1-105, for example. In some cases, the optic 3-250 can be mounted by itself in the integrated optical mount 3-210, as depicted in the drawing. In other embodiments, an optic can be mounted within a supporting fixture (e.g., an annular plate, an adjustable mount) that can be placed in the integrated optical mount 3-210.

According to some embodiments, an optical component 3-250, or supporting fixture, can include a flat surface that registers to and rests against the coplanar surfaces 3-230 of the integrated optical mount 3-210. The optic or fixture can be retained in the integrated mount by a compliant retaining device (e.g., an O-ring mounted on a bar that can be fastened to the base chassis, a flexible plastic bar or arm, etc.). The compliant retaining device can contact a top edge of the optic 3-250 or supporting fixture, and can exert forces on the optic or fixture in directions towards inclined surfaces 3-240 and the coplanar surfaces 3-230. A lower edge of the optic 3-250 or supporting fixture can contact points on the inclined surfaces 3-240. The inclined surfaces 3-240 can also provide a force against the optic or fixture having a component that is directed in part toward the coplanar surfaces 3-230. The contact points at the inclined surfaces 3-240 and forces directed toward the coplanar surfaces 3-230 can self-align the optic or fixture to a desired orientation and location within the laser cavity. In some implementations, an optic or supporting fixture can be bonded in the integrated optical mount (e.g., with an adhesive) in an aligned orientation.

One or more integrated optical mounts 3-210 can be formed in a base chassis of a mode-locked laser 1-110, according to some embodiments. In some cases, an axial trench 3-220 can extend through several integrated optical mounts, as depicted in FIG. 3-2A. Among the advantageous features of an integrated optical mount are a lowering of the mode-locked laser's optical axis. This can reduce effects of mechanical vibrations that might otherwise couple into and be amplified by optical mounts extending from a surface of the base chassis, and can reduce effects of thermal expansion (e.g., slight warping of the base chassis 2-105) that might otherwise be amplified by motion of optical mounts extending from a surface of the base chassis.

Referring again to FIG. 2-1, the inventors have discovered that changing a distance between the output coupler 1-111 and the gain medium 1-105 can change the FWHM value of the mode-locked pulse temporal profile (also referred to as pulse duration). Mode-locking of the laser can be achieved with the distance between the output coupler 1-111 and the gain medium 1-105 varied between 0 mm and 10 mm, and the pulse duration can be varied between approximately 9 picoseconds and approximately 38 picoseconds over this range of distances by selecting different distances to obtain different pulse durations. According to some embodiments, the distance between the output coupler 1-111 and the gain medium 1-105 is set between 4 mm and 8 mm.

The inventors have also discovered that stable and efficient operation over a range of average lasing powers is achieved when the intracavity beam waist of the laser at the output coupler 1-111 is between 100 microns and 180 microns. The value of the beam waist at the output coupler 1-111 is determined in part by intracavity optics, such as curved mirror 2-117, by distance of the output coupler to the curved mirror, and by the pump beam waist in the gain medium 1-105. According to some embodiments, the beam waist of the lasing wavelength in the gain medium can be significantly smaller that the pump beam waist in the gain medium 1-105. For example, the beam waist for the lasing wavelength in the gain medium can be between 100 microns and 150 microns in the gain medium, and a smallest waist for the pump beam can be between 180 microns and 250 microns, wherein the pump beam may not be fully symmetric about its optical axis. The value of the beam waist at the output coupler 1-111 and in the gain medium 1-105 may also be affected by the focal length of the second curved mirror 2-127 and its distance to the saturable absorber mirror 1-119. Having a smaller beam waist for the lasing beam of the mode-locked laser 1-110 than the laser diode pump beam can improve stability of the mode-locked laser operation (e.g., make the laser less susceptible to power and mode-locking fluctuations due to relative motion of the laser beam and laser diode pump beam in the gain medium 1-105. The term "beam waist" is used to refer to the spatial extent at which the laser beam intensity falls from a peak value to a $1/e^2$ value on opposite sides of the beam. A round beam may be characterized by a single beam waist. An elliptical beam may be characterized by two beam waists: one for the beam's minor axis and one for the beam's major axis.

At an opposite end of the laser cavity, a saturable absorber mirror (SAM) 1-119 be mounted. Referring to FIG. 3-3, the SAM can comprise a multilayer semiconductor structure 3-312 that exhibits nonlinear optical absorption (e.g., a multiple quantum well) and a high reflector 3-330 formed on a substrate 3-305. The nonlinear optical absorption can induce passive mode locking in the laser. For example, the SAM can exhibit higher absorption and loss at low optical intensities, and can bleach or exhibit little absorption and less loss at high optical intensities. The semiconductor structure 3-312 can be spaced from the high reflector 3-330 in the SAM so that the semiconductor structure is located at approximately a peak intensity of an optical standing wave created by the optical field incident on and reflected from the high reflector 3-330. An example of a SAM is part number SAM-1064-5-10ps-x available from BATOP Optoelectronics GmbH of Jena, Germany. Because of the SAM's nonlinear optical absorption, the laser preferentially operates in a pulsed mode of operation (passively mode locked) since the high intensities of the optical pulses experience less loss in the cavity than lower intensity, continuous-wave operation of the laser.

In some implementations, a SAM 1-119 can be mounted on a rotating and/or transverse-positioning mount, so that the SAM's surface can be moved in a direction transverse to the optical axis 1-125 (the Z axis in the drawing). Should the SAM become damaged, the SAM can be moved and/or rotated so that the intracavity beam is focused onto an undamaged region of the SAM. In some cases, the SAM 1-119 can be mounted on a mount that provides angular adjustment, e.g., to aid in alignment of the laser cavity.

In other embodiments, the SAM can be mounted on a non-adjustable mount 2-119. The non-adjustable mount can include a thermal conductor such as aluminum or copper that dissipates heat from the SAM to the base chassis 2-105 (not shown in the drawing). In some embodiments, the SAM mount 2-119 can comprise a plate of aluminum or copper or any suitable thermally-conductive material to which the SAM is adhered with a thermally-conductive adhesive. In some implementations, the SAM can be adhered to a copper foil on a piece of a printed circuit board, which is used as the SAM mount 2-119. The SAM mount can be attached to a machined surface in the base chassis or a surface of a fixture attached to the base chassis with one or more screws that allow the same to be roughly aligned to the optical axis 1-125 of the laser. For example, the SAM mount can be crudely positioned by hand in X and Y directions when secured to the base chassis, but otherwise not provide for fine angular adjustment (e.g., in two degrees of freedom) of the SAM's surface with respect to an optical axis of an intracavity beam of the mode-locked laser that is incident on the SAM. Other optical components in the laser cavity can be used to adjust the incident angle and position of the optical axis on the SAM. By mounting the SAM 1-119 on a fixed mount, cost and complexity associated with a multi-axis/multi-angle adjustment mount can be eliminated.

According to some embodiments, the SAM can be formed from a gallium-arsenide semiconductor composition. The SAM can be cut from a larger substrate or wafer, and can be square in shape with a maximum dimension across the face of the SAM between 1 mm and 3 mm. A relaxation time of the SAM's absorption can be between 10 ps and 30 ps. A non-saturated absorption of the SAM can be between 2% and 6%. The modulation depth of the SAM can be between 60% and 74% of the SAM's non-saturated absorption. In some implementations, the relaxation time is approximately 25 ps and the non-saturated absorption is approximately 4%. Such a SAM 1-119 can support mode-locked lasing with pulse durations between 12 ps and 20 ps. A saturation fluence of the SAM can be about 70 microJoules/cm$^2$ ($\mu$J/cm$^2$), in some embodiments.

The inventors have recognized and appreciated that the optical fluence on the SAM from the intracavity laser beam should be kept below 2.5 milliJoules/cm$^2$ (mJ/cm$^2$) for prolonged operation of a gallium-arsenide SAM. At values equal to 5 mJ/cm$^2$ or higher, the SAM may damage. In some implementations, the fluence on the SAM can be kept below about 10 times the saturation fluence of the SAM. The fluence on the SAM can be controlled by controlling the beam waist at the SAM (e.g., with a curved mirror 2-127 located in the laser cavity) and by controlling the intracavity power with the choice of reflectivity of the output coupler 1-111. According to some embodiments, a beam waist at the SAM is between 80 microns and 120 microns when the output coupler reflectivity is between 82% and 88%.

Between the output coupler 1-111 and the SAM 1-119, there can be a plurality of mirrors that fold the optical axis of the laser cavity multiple times. Some of these mirrors (e.g., mirrors 2-115, 2-120, 2-121, 2-122, 2-123, 2-124, 2-125 referring to FIG. 2-1) can have flat surfaces and be mounted in non-adjustable mounts. According to some embodiments, two of the mirrors 2-117, 2-127 can have curved surfaces and comprise a focusing reflector. In some cases, another type of focusing optic (e.g., a lens or compound lens) can be used instead of focusing reflectors for mirrors 2-117, 2-127 (e.g., if the intracavity beam is not folded at the location of the mirrors 2-117 or mirror 2-127). For flat and curved mirrors that are used to fold the optical axis of the laser, the reflectivity of the mirror can be very high for the lasing wavelength at the angle of incidence for which the mirror will be used. For example, the reflectivity for such a mirror can be greater than 99% in some cases, and yet greater than 99.5% in some cases. The surface quality of one or more of the folding mirrors can be at least 10-5 (scratch and dig) and a wavefront error can be at most $\lambda$/10. In some cases, the surface quality of one or more of the folding mirrors can be at least 40-20 (scratch and dig) and a wavefront error can be at most λ/10. A higher value for scratch-dig surface quality can significantly reduce the cost of the folding mirrors.

In some implementations, at least one of the mirrors (e.g., mirror 2-124) can fold the intracavity beam multiple times for a single transit from the gain medium 1-105 to the SAM 1-119. For the example configuration shown in FIG. 2-1, a bounce sequence for an optical pulse 1-120 travelling from the gain medium 1-105 to the SAM 1-119 is a sequence of reflections from mirrors 2-115, 2-117, 2-120, 2-121, 2-122, 2-123, 2-124, 2-125, 2-124, 2-127, 2-124, and then to the SAM 1-119. In this sequence, one of the intracavity mirrors 2-124 is used for multiple reflections and the angle of incidence is reversed in sign on this mirror for at least two reflections as the beam travels from one end of the laser cavity to the other end. For example and referring to FIG. 2-1, the first angle of incidence is in the +Z direction and the second angle of incidence on mirror 2-124 is in the −Z direction as the beam travels from the output coupler 1-111 to the SAM 1-119. After reflecting from the SAM 1-119, the pulse will then return in the reverse bounce sequence to the gain medium. By having multiple folds of the optical axis within the compact laser module, the cavity length can be extended to obtain a pulse repetition rate below 200 MHz and as low as 50 MHz. The pulse repetition rate will depend upon the length of the laser cavity, which is determined in part by the number of bounces between mirrors in the cavity and the distances between the mirrors. According to some embodiments, the pulse repetition rate can be changed by relocating mirrors and adding or removing mirrors within the cavity between the first curved mirror 2-117 and the second curved mirror 2-127 to increase or decrease the optical path length between the output coupler 1-110 and saturable absorber mirror 1-119. Because the intracavity beam is approximately collimated between the first curved mirror 2-117 and the second curved mirror 2-127, changes to pulse repetition rate can be made more easily than if the beam were not collimated in this region. In some implementations, extra integrated optical mounts can be formed in the base chassis for relocating mirrors to obtain different pulse repetition rates.

As noted above, the inventors have recognized and appreciated that pulse repetition rates below 200 MHz and as low as 50 MHz are desirable for massively-parallel analysis of samples on a bio-optoelectronic chip. However, using multiple mirrors, with some mirrors used multiple times, requires a very high degree of stability of the mirrors with respect to each other to maintain stable mode-locked lasing over periods of hours. Integrated mounting of the mirrors against supporting surfaces in a base chassis 2-105 that includes strengthening ribs can achieve the requisite stability of the mirrors and stable mode-locking operation.

Figures 1, 2, 3, 4:
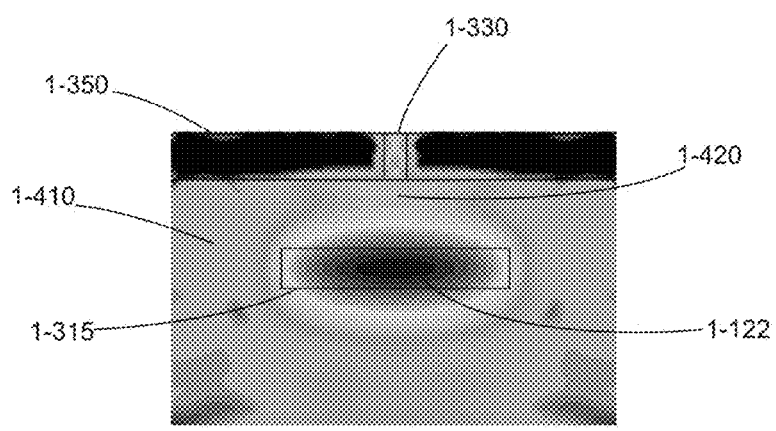

An example of a non-adjustable mount for a folding mirror is shown in FIG. 3-4. According to some embodiments, the mount can be machined or otherwise formed into the base chassis 2-105. The mount can comprise a supporting and aligning wall 3-410 located adjacent to two sloped surfaces 3-424 that are spaced apart. The sloped surfaces can be formed on two protrusions 3-420, according to some embodiments. In some implementations, there can be a single sloped surface. The sloped surface or surfaces can be inclined toward the aligning wall 3-410, as illustrated in the drawing. There can be one or more threaded holes 3-430 adjacent to the wall. An optical component (e.g., a flat mirror or curved mirror) can be placed on the sloped surface or surfaces 3-424 with a back side resting against the aligning wall 3-410. A clamping component (not shown) having a pliable or flexible component can be secured via the threaded hole 3-430 or holes to retain the optical component against the aligning wall.

The aligning wall 3-410 can be machined in the base chassis 2-105 with a selected orientation, so that an optical component held against the aligning wall 3-410 will be approximately aligned at desired angles with respect to a planned optical axis of the laser beam through the laser cavity. The inventors have recognized and appreciated that aligning walls 3-410 can be formed to a high degree of angular accuracy by machining for angles lying within a plane parallel to the base chassis (e.g., for angles that define incident and reflection angles of the laser beam in an XZ plane in FIG. 2-1). However, the machining accuracy of forming the aligning walls 3-410 is appreciably less for angles that would deflect the laser beam out of a plane parallel to the base chassis. Accordingly, one of the mirror mounts between the gain medium 1-105 and SAM 1-119 can include an angular adjustment (one degree of freedom) to accommodate for manufacturing errors that would cause deflection of the laser beam out of a plane parallel to the base chassis. According to some embodiments, the mirror mount having a single degree of freedom is located between one-quarter and three-quarter of the distance between the gain medium and SAM.

In some implementations, one folding mirror 2-115 can be configured to control polarization of radiation within the cavity and allow monitoring of pump-beam radiation (indicated as the heavy dashed line in FIG. 2-1). For example, the folding mirror 2-115 can be coated to reflect s polarization (polarization that is out of the plane of the base chassis, in the Y direction) with a high reflectivity greater than 99%, or even greater than 99.5% in some cases, and to have a lower reflectivity for the orthogonal p polarization, so that lasing in the p polarization is prevented. In some cases, the folding mirror 2-115 can be a polarizing beam splitter that transmits more than 20% of the p polarization and reflects the s polarization with high reflectivity. The folding mirror 2-115 can additionally transmit most or nearly all of the pump-beam radiation to a photodetector 2-116 located behind the mirror. The folding mirror can include a dichroic coating to allow transmission of the pump-beam radiation, in some embodiments. In other embodiments, a dichroic coating may not be used, and the coating for the lasing wavelength may allow adequate transmission of the pump-beam radiation through the folding mirror 2-115 for detection. An output from the photodetector 2-116 can be provided to the PCB 2-190 for signal processing and/or transmission to an external signal processor.

In some embodiments, two curved mirrors 2-117, 2-127 can be designed and located within the laser cavity to obtain desired beam waist sizes within the gain medium 1-105 and the SAM 1-119. A first curved mirror 2-117 can be located in a first portion of the laser cavity near the gain medium 1-105. A second curved mirror 2-127 can be located in a second portion of the laser cavity near the SAM 1-119. At least between the curved mirrors, there can be a plurality of folding mirrors that fold the optical axis of the laser and extend the laser cavity length in a cavity length extending region. There can additionally be a mirror 2-124 between curved mirror 2-127 and the SAM 1-119 that folds the intracavity laser beam multiple times to extend the length of the cavity in the cavity length extending region. For example, curved mirror 2-127 and mirror 2-124 can fold the intracavity beam three times on immediately successive bounces from these two reflectors, as indicated in FIG. 2-1.

According to some embodiments, the first curved mirror 2-117 can be a spherical reflector and have a focal length $f_1$ between 240 mm and 260 mm. A tolerance on the focal length for this reflector can be ±1% of the focal length. The inventors have found that the first curved mirror 2-117, with a focal length of approximately 250 mm, can be placed between 230 mm and 310 mm from the output coupler 1-111 and stable mode-locked operation having different characteristics can be obtained. According to some embodiments, the first curved mirror can be located between 280 mm and 300 mm from the output coupler to obtain stable mode-locked operation over a large range of operating powers of the compact laser module. In this configuration, the gain medium 1-105 can be located between 4 mm and 8 mm from the output coupler. The focal length of the first curved mirror 2-117 and its location with respect to the gain medium 1-105 and output coupler 1-111, and the focal length of the second curved mirror 2-127 and its location with respect to the SAM 1-119 can determine the beam waist of the intracavity beam in the gain medium.

A focal length of the first curved mirror 2-117 may have other values in other embodiments. For example, a shorter focal length $f_1 < 230$ mm can be used for a more compact mode-locked laser that operates at lower powers. In embodiments, the output coupler 1-111 can be placed a distance $d_1$ from the first curved mirror 2-117 that is in a range of values within 30% of the focal length $f_1$ (e.g., $0.7f_1 < d_1 < 1.3f_1$). In some cases, $0.9f_1 < d_1 < 1.3f_1$.

In some implementations, the first curved mirror 2-117 can be mounted in an adjustable mount that provides only two degrees of freedom for adjusting orientation angles (in-plane, and out-of-plane angles) of the mirror with respect to the optical axis of the laser. An adjustable mount can allow an operator to finely adjust the position (one or more of X, Y, Z) and/or orientation (pitch and/or yaw with respect to the optical axis of the incident intracavity beam) of the optical component while the laser is lasing, so that operation of the laser can be tuned for stability, beam quality, output power, and/or pulse characteristics. Fine tuning can be achieved by micrometers and/or finely-threaded screw adjustments on mirror mounts, for example.

Providing only two degrees of freedom for the first curved mirror 2-117 and only one degree of freedom for a folding mirror (e.g., mirror 2-123) as the only adjustments for aligning the laser cavity in real time while the laser is lasing can reduce cost and complexity of the compact mode-locked laser module. In other cases, the mirror mount for the first curved mirror 2-117 can include additional degrees of freedom for adjusting the position of the mirror, for example. According to some embodiments, adjustments can be made to the pump module 2-140 after adjusting curved mirror 2-117 to align or re-align the pump beam and increase output power from the mode-locked laser.

A second curved mirror 2-127 can be a spherical reflector and have a focal length $f_2$ between 240 mm and 260 mm. A tolerance on the focal length for this reflector can be ±1% of the focal length. The inventors have found that the second curved mirror 2-127, with a focal length of approximately 250 mm, can be placed between 260 mm and 290 mm from the SAM 1-119 and stable mode-locked operation having different characteristics can be obtained. According to some embodiments, the second curved mirror can be located between 270 mm and 285 mm from the SAM 1-119 to obtain stable mode-locked operation over a large range of operating powers of the compact laser module. The focal length of the second curved mirror 2-127 and its location with respect to the SAM 1-119 can determine the beam waist of the intracavity beam at the SAM 1-119 and also affect the beam-waist at the gain crystal.

A focal length of the second curved mirror 2-127 may have other values in other embodiments. For example, a shorter focal length $f_2 < 240$ mm can be used for a more compact mode-locked laser that operates at lower powers. In embodiments, the SAM 1-119 can be placed a distance $d_2$ from the second curved mirror 2-127 that is in a range of values within 20% of the focal length $f_2$ (e.g., $0.8f_2 < d_2 < 1.2f_2$). In some cases, $f_2 < d_2 < 1.2f_2$.

The second curved mirror 2-127 can be mounted in a non-adjustable mount, as described above in connection with FIG. 3-4, for example, to reduce cost and complexity of the laser module. As described above, all of the reflective components in the laser cavity (except the first curved mirror 2-117 and the folding mirror 2-123) can be mounted in self-aligning, non-adjustable mounts. Further, the first curved mirror 2-117 can have only two degrees of freedom for angular adjustments and the folding mirror 2-123 can have only one degree of freedom for angular adjustment. The inventors have discovered that the mode-locked laser cavity can be aligned for stable operation for long periods of time using only these three adjustments, according to some embodiments. For example, the first curved mirror 2-117 can be used to steer a beam from the gain medium 1-105 to the SAM 1-119, which is mounted in a fixed location to receive the beam. Any out-of-plane deviations (in the ±Y directions in FIG. 2-1) can be accommodated by adjusting the single degree of angular adjustment on folding mirror 2-123. If the SAM 1-119 does not receive the intracavity beam at normal incidence so as to reflect the beam back along the same path, the angle of incidence on the SAM can be adjusted by translating the intracavity beam on the second curved mirror 2-127. Since the SAM 1-119 is nearly at the focus of the second curved mirror, a translation of the beam on this mirror alters the incidence angle at the SAM. The intracavity beam can be translated across the surface of the second curved mirror by making angular adjustments to the first curved mirror 2-117. Adjustments can be made to the first curved mirror until the intracavity beam is reflected back on itself from the SAM 1-119.

The inventors have discovered that the spot size of the intracavity laser beam on the SAM can be more sensitive to changes in distance between the first curved mirror 2-117 and the laser's output coupler 1-111 than to changes in distance between the second curved mirror 2-127 and SAM 1-119. This result relates to the extended cavity length between the first curved mirror 2-117 and the second curved mirror 2-127. This extended cavity length can be more than half the length of the laser cavity, throughout which the intracavity laser beam can be approximately collimated. Changes in the distance between the curved mirror 2-117 and output coupler 1-111 can affect collimation in the extended cavity, which can amplify changes in beam size at the second curved mirror 2-127. The amplification in turn affects the spot size in the SAM 1-119 more strongly than changes in distance between the second curved mirror 2-127 and SAM 1-119. Accordingly, the position of the first curved mirror 2-117 can be used to adjust the fluence on the SAM 1-119. In some embodiments, the amplification effect can be reduced by increasing the focal length of the second curved mirror 2-127.

When the laser cavity is aligned and configured as described above, such that a beam waist in the gain medium 1-105 is between 100 microns and 150 microns, and the beam waist at the SAM 1-119 is between 80 microns and 120 microns, the inventors have discovered that the laser cavity satisfies a "stability criterion" for optical resonators (a condition known to those skilled in the art of lasers) that spans a change from 0 diopter to 15 diopters of thermal lensing effects in the gain medium 1-105 and for focal length errors of the two curved mirrors 2-117, 2-127 of ±1%. At high optical powers, the gain medium 1-105 can acquire appreciable heat from the pump radiation, and the heated gain medium can create an optical lens (also referred to as thermal lensing) that has a focusing power (diopter) that is dependent upon the temperature of the medium. For optically-pumped, high-power lasers, the changes due to this thermal lensing can destabilize the laser and extinguish lasing for increases in pump power by 50% from an initial stable operating point. The inventors have observed that the compact mode-locked laser module 1-108 maintains stable mode-locking operation for variations in pump power from 2 Watts to 8 Watts, an increase of 300% in pump power from an initial stable operating point. The range of stability for the laser cavity is surprisingly large, and allows the compact mode-locked laser to be operated over a large range of intracavity and output powers. For example, the average output power from the laser can vary between 350 milliwatts and 3.5 Watts over this range of pump power, while the FWHM pulse duration remains between 12 picoseconds and 18 picoseconds. This output can be frequency doubled to produce pulses of a same duration at a wavelength of 532 nm, for example, with average power levels between 100 milliwatts and 1.5 Watts.

According to some embodiments, there can be optical components mounted within the laser cavity to help stabilize operation of the mode-locked laser and/or improve beam quality of the mode-locked laser. For example, a spatial mode filter 2-118 can be located in the laser cavity and configured to prevent lasing in higher-order spatial modes. The mode filter 2-118 can comprise an aperture of any suitable shape (e.g., round, oval, crescent shaped, square, rectangular, polygonal, etc.). The aperture can be mounted in a non-adjustable mount, or can be mounted such that it can be moved in directions transverse to the intracavity beam's optical axis. The size of the aperture can be adjustable in some cases (e.g., an iris). In various embodiments, the aperture constrains lasing operation to the lowest-order transverse spatial mode of the laser cavity, which can improve stability of mode locking.

Beam steering components can be included in the laser module 1-108 in some embodiments for dynamic stabilization and alignment. For example, one or more anti-reflection coated laser windows or optical flats 2-128 that can be rotated at an angle with respect to the intracavity beam can be operated automatically by an actuator 2-162 to translate and/or change an incident angle of the intracavity beam on the SAM 1-119. There can be mechanical linkage 2-164 between an actuator and laser window and a pitch or yaw mount for the laser window that enable automated pitch or yaw adjustments to the laser window 2-128. The actuator 2-162 can comprise a stepper motor, piezoelectric transducer, capacitive transducer, or any other suitable actuator.

Rotation of an intracavity laser window will shift laterally the outgoing beam from the laser window in the direction of rotation. The amount of lateral shift can be determined by applying Snell's law to the two interfaces of the laser window. If the laser window is located between the second curved mirror 2-127 and the SAM 1-119, then rotation of the laser window will mainly translate the intracavity beam on the SAM. Rotation of such laser window can be used to extend the lifetime of the SAM by moving the intracavity beam across the SAM. A scanning motion my reduce fatigue of the SAM, or if the SAM has been damaged the beam can be moved away from the damaged spot. If the laser window 2-128 is located before the second curved mirror 2-127 as depicted in FIG. 2-1, then rotation of the laser window will mainly change the incident angle of the intracavity beam on the SAM. Rotation of such laser window can be used to dynamically align or realign the laser cavity to obtain and/or maintain stable mode-locked operation.

Signals that indicate laser performance and that can be used for automatically adjusting intracavity beam-steering components can include any one or combination of pump power (detected with photodetector 2-116 or a pump photodetector (not shown) that is mounted in the pump module), laser power and/or pulse characteristics (detected with a laser output photodetector 2-154, which can be sensitive to the lasing wavelength), and second-harmonic power (detected with a doubled-output photodetector 2-182). The signal or signals can be provided to circuitry on PCB 2-190 for processing and generation of feedback control signals to operate one or more actuators 2-162. In some embodiments, one or both of the laser output photodetector 2-154 and doubled-output photodetector 2-182 can be mounted on the PCB 2-190 and received radiation through a hole and/or window (not shown) located in a side of the mode-locked laser module 1-108. In some implementations, rotation of an intracavity beam-steering component can be automated to fine tune cavity alignment and/or change a position of the intracavity beam on the SAM 1-119 based on one or more feedback signals.

According to some embodiments, cavity alignment can be obtained additionally or alternatively by inducing asymmetric thermal gradients in the gain medium 1-105. Asymmetric thermal gradients can affect thermal lensing and alter the refractive index within the gain medium 1-105 in such a way to cause small angular deflections in the intracavity laser beam as it passes through the gain medium 1-105. In some implementations, one or more temperature-controlling devices (e.g., resistive heating elements, TEC coolers, or a combination thereof) can be coupled to one or more sides of the gain medium. According to some embodiments, the gain medium 1-105 can have two to four independently-operable, temperature-controlling devices (not shown in FIG. 2-1) thermally coupled to two to four faces (four longitudinal edges) of the gain medium. Thermal coupling can comprise thermal epoxy or indium foil located between a temperature-controlling device and face of the gain medium 1-105. A temperature-controlling device can also include thermal coupling to a heat sink (such as the laser block) on an opposite side of the temperature-controlling device. In some cases, operation of one or more of the temperature-controlling devices can provide beam deflection transverse to the optical axis 2-111. By selectively altering temperatures at the temperature-controlling devices, the intracavity laser beam can be steered and re-aligned. In some cases, one or more intracavity laser windows 2-128 can be adjusted in tandem with thermal beam steering in the gain medium to reposition the intracavity beam on the SAM, for example, and/or maintain stable mode-locked operation of the laser.

The inventors have recognized and appreciated that average power and/or spectral characteristics of the mode-locked laser can be determinative of stable, mode-locked operation. For example, if the laser's average power during mode-locked operation falls below a certain value, there may not be enough nonlinear optical absorption in the SAM 1-119 to support mode locking. The laser may then Q-switch and damage the SAM 1-119. In some cases, rapid fluctuations of the laser's average output power may indicate that the laser is Q-switching in addition to mode locking, which can damage the SAM 1-119. In some embodiments, at least one sensor 2-154 (e.g., a photodiode) can be included and arranged to sense optical power produced by the laser 1-110 and/or output pulse or mode-locking characteristics of the laser. For example, a signal from a first sensor 2-154 can be spectrally analyzed to detect sidebands near the mode-locking frequency, which can indicate the onset of Q-switching and/or instabilities in the mode-locked pulse train of the laser 1-110. A second sensor (not shown) can detect average optical power produced by the laser 1-110. If the sensed average laser power drifts below a preset level and/or if sidebands or power fluctuations are detected by the first sensor 2-154, an automated cavity alignment routine can be executed to recover power and/or the laser can be shut off for servicing. In some cases, sidebands that indicate instabilities in the mode-locked pulse train are due to lasing of higher-order spatial cavity modes. Such instabilities can be corrected by adjusting an intracavity spatial mode filter 2-118 automatically or manually, for example. According to some embodiments, one or more sensors 2-154 that are sensitive to the lasing wavelength can be mounted on PCB 2-190.

In some cases, additional signals can be processed to analyze laser behavior. For example, the pump power can be evaluated with a pump power sensor 2-116 (which can be a photodiode or other suitable photodetector) in conjunction with the average power level from the laser. In some embodiments, the amount of frequency-doubled power can be monitored with sensor 2-182 (which can be a photodiode or other suitable photodetector) additionally or alternatively. For example, a reduction in average frequency-doubled power while the average laser power remains nearly constant could indicate changes in mode-locked pulse length, or a problem with the frequency-doubling optical components.

In operation, a mode-locked laser 1-110 that employs $Nd^{3+}:YVO_4$ as the gain medium and arranged as described above can produce pulses at 1064 nm having a FWHM value of approximately 15 ps. The pulse extinguishes by approximately 80 dB within 100 ps from the peak of the pulse. The pulse repetition rate is approximately 67 MHz, and the average power of the mode-locked laser at the fundamental wavelength can be varied from 350 mW to 3.5 W. The conversion efficiency to a frequency-doubled wavelength (described further below) can be as high as 30% in some cases, so that pulses at 532 nm can be produced with average output powers between 100 mW and 1.5 W. In some cases, the conversion efficiency can be as high as 35%. The AC power required to operate the laser is less than about 20 Watts. The laser is compact, occupies a volume of less than 0.1 $ft^3$, weighs slightly less than 2 kilograms, and can be readily incorporated as a module into a portable analytic instrument, such as a table-top instrument for sequencing DNA.

Alternative Configurations for the Laser Cavity

Although the compact mode-locked laser module 1-108 described above uses multiple mirrors that extend the cavity length and reduce the pulse repetition rate, other embodiments can use other optical components additionally, or alternatively, to extend the cavity length. Some examples of optical delay elements are depicted in FIG. 3-5A through FIG. 3-5D. According to one embodiment, an optical delay element 3-510 can comprise an argyle block, as depicted in the plan view of FIG. 3-5A. The argyle block can comprise a first right-angle prism 3-520 and a second right-angle prism 3-522. According to some embodiments, the perpendicular side faces of the prisms can be uncoated, though in other embodiments the perpendicular faces can include high-reflective coatings. In some implementations, a length of a perpendicular face on one of the prisms can measure between about 20 mm and about 60 mm. Each prism can be formed of any suitable optical quality glass, for example BK-7 or fused silica. For high thermal stability, the delay element can be formed from an ultra-low expansion glass such as ULE, available from Corning. The side faces of the prisms can be polished to be of high optical quality, for example, having a wavefront error of $\lambda/10$ or better and a surface quality of 10-5, for example.

The first prism 3-520 and second prism 3-522 can be offset and adhered together, as depicted in the drawing. The prisms can be adhered via optical bonding or using an optical adhesive. In some implementations, the optical delay element 3-510 can be formed from a single piece of glass by cutting and polishing. An intracavity laser beam 3-101 can enter through a first port of the delay element and be reflected internally along a circuitous optical path, depicted as the dotted line, before exiting a second port of the argyle block.

According to some implementations, a delay element can be double-passed to double the optical path length provided by the delay element. For example, an output beam from a single-pass output port of the delay element can be retro-flected with a spatial offset back through the delay element, so that the return beam exits the input port but is displaced from the input beam 3-101, which can be received from a first portion of the laser cavity. The displaced output beam can be directed to a second portion of the laser cavity.

Another embodiment of an optical delay element 3-512 is depicted in FIG. 3-5B. According to some embodiments, the optical delay element can comprise a single optical block that is formed in a rectangular shape. The delay element 3-512 can comprise perpendicular edge faces 3-530 that reflect an intracavity beam back-and-forth within the delay element, as depicted in the drawing by the dotted line. The delay element can further include two polished faces that provide an entry port 3-532 and exit port 3-534 for the delay element. The perpendicular side faces can be uncoated in some embodiments, or coated with a high-reflective coatings (e.g., multilayer coatings) in other embodiments. In some implementations, a maximum length of an edge of the delay element can measure between about 20 mm and about 60 mm. The thickness of the block, measured in a direction into the page, can be between about 5 mm and about 20 mm. The delay element 3-512 can be formed of any suitable optical quality glass, as described above. The reflective edge faces can be polished to be of high optical quality, for example, having a wavefront error of $\lambda/10$ or better and a surface quality of 10-5, for example. The delay element 3-512 can be doubled-passed to increase the optical path length within the laser cavity.

FIG. 3-5C depicts yet another embodiment of an optical delay element 3-514. According to some embodiments, the delay element can comprise a pair of planar mirrors $M_1$, $M_2$ that are spaced a distance D apart at their centers and inclined at a slight angle $\alpha$ with respect to each other. Each mirror $M_1$, $M_2$ can have a length L. The spacing D between the mirrors $M_1$, $M_2$ can be between about 10 mm and about 50 mm, according to some embodiments. The length L of the mirrors $M_1$, $M_2$ can be between about 20 mm and about 60 mm, according to some embodiments. The angle $\alpha$ can be between about 0° and about 10°, according to some embodiments. The height of the mirrors $M_1$, $M_2$, measured along a direction into the page, can be between about 5 mm and about 20 mm. The mirrors $M_1$, $M_2$ can be formed of any suitable optical quality glass, as described above. The reflective surfaces of the mirrors $M_1$, $M_2$ can be polished to be of high optical quality, for example, having a flatness of $\lambda/10$ or better and a surface quality of 10-5, for example. The reflective surfaces can be coated with high-quality, high-reflective, multilayer coatings and have a reflectivity greater than about 99.5% in some implementations. In some embodiments, the reflectivities can be greater than about 99.9%. An intracavity beam 3-101 entering the mirror pair in a first direction will undergo multiple reflections, dependent upon the incident angle and angle $\alpha$ between the mirrors $M_1$, $M_2$.

Another embodiment of an optical delay element 3-516 is depicted in FIG. 3-5D. This embodiment may comprise a solid block analog to the embodiment depicted in FIG. 3-5C. According to some implementations, an optical delay element 3-516 can comprise a solid block of optical material having five surfaces as depicted in the drawing. Two surfaces 3-534 can be inclined at a slight angle $\alpha$ with respect to each other. These surfaces can include high reflective coatings to reflect an intracavity beam 3-101 back-and-forth between the surfaces along a dotted path as indicated in the drawing. The delay element 3-516 can further include two uncoated or anti-reflection coated surfaces 3-532 that provide an entry port and exit port to and from the delay element. According to some embodiments, the delay element can be arranged so that the intra-cavity laser beam 3-101 enters and exits the delay element at Brewster's angle. The delay element 3-516 can be formed of any suitable optical quality glass, as described above. The reflective surfaces 3-534 can be polished to be of high optical quality, for example, having a flatness of $\lambda/10$ or better and a surface quality of 10-5. The reflective surfaces can be coated with high-quality, high-reflective, multilayer coatings and have a reflectivity greater than about 99.5% in some implementations. In some embodiments, the reflectivities can be greater than about 99.9%.

An advantage of solid-block delay elements 3-510, 3-512, 3-516 respectively depicted in FIG. 3-5A, FIG. 3-5B and FIG. 3-5D is that these elements do not require as careful alignment when inserted into the laser cavity as would be required for multi-component delay elements such as the two mirrors of FIG. 3-5C or the multiple flat mirrors shown in FIG. 2-1. However, solid block components can require a larger number of reflections from mirror surfaces for pulse repetition rates below 200 MHz, and will require more precision during a manufacture. As a result, the cost of the solid-block delay elements can be high. By using integrated non-adjustable mounts in a single-piece base chassis 2-105 and using one or two adjustable mounts to accommodate for machining errors in the non-adjustable mounts, as described above, lower cost mirrors can be used to provide a desired optical delay. An advantage of the multi-mirror delay element is that the cavity length can be changed more readily and flexibly by changing the position of one or more cavity-folding mirrors to redefine the laser cavity.

Although thermal effects within the gain medium 1-105 can be used to steer and align the intracavity beam, as described above, the inventors have recognized and appreciated that thermal heating effects and/or mechanical stresses on optical elements within the laser cavity can be a significant factor that can undesirably influence the performance of a compact, mode-locked laser. Thermal heating can arise at the pump module 2-140 and the gain medium 1-105 when mode-locked laser 1-110 is operated at average power levels for the fundamental lasing wavelength over 250 mW, for example. In regard to the gain medium 1-105, the inventors have recognized and appreciated that additional care must be taken when mounting a gain crystal such as neodymium vanadate. A mount should allow for heat dissipation, and yet avoid mechanically stressing the crystal. The mount with relief cuts at vertices, shown in FIG. 3-1A, can allow for heat dissipation and avoid undesirable stresses on the crystal. Additionally or alternatively, the use of a thermally-conductive adhesive to secure the gain medium 1-105 in a mount can provide stress relief for the gain medium 1-105.

The inventors have further recognized and appreciated that mounting structures that dissipate heat, can adversely affect optical alignment of a laser cavity. For example, a mount 3-100 for the gain medium 1-105 and/or the pump diode module 2-140 can be fastened to the base chassis 2-105 and dissipate heat into the base chassis. Since the base chassis is comparatively small for high-power lasers, this heating can cause expansion and/or warping or other distortions of the base chassis. As a result, distortion of the base chassis 2-105 can misalign optical elements of the laser cavity and adversely affect the laser's operation over time. In severe cases, the thermal heating can cause an appreciably degradation in power and can terminate mode-locking of the laser.

In some embodiments, a mounting structure or component of a mode-locked laser that requires significant heat dissipation can be mounted on a partially-thermally-isolated platform 3-610, as depicted in plan view in FIG. 3-6A. The platform can partially thermally isolate the baseplate body 3-605 from heat dissipated by the high-temperature structure or component mounted on the platform 3-610. Elevation views of the platform, taken at the cut lines in FIG. 3-6A, are depicted in FIG. 3-6B and FIG. 3-6C. A partially-isolated platform 3-610 can be formed in a baseplate 2-105 by a machining process, according to some implementations. For example, the baseplate body 3-605 can be part of a solid block of material that is machined to form a housing for a compact, mode-locked laser as described above. One or more through-trenches 3-630 can be machined through the baseplate body 3-605 to form the partially-isolated platform 3-610. These trenches can partially separate and thermally isolate the platform 3-610 from the baseplate 3-605. For example, heat cannot be dissipated as readily from the platform into the baseplate. A lower surface of the platform 3-610 can be thermally contacted to a thermal-electric cooler (not shown), according to some implementations. In some cases, a lower surface of the platform can be machined or otherwise formed to have heat-dissipating fins 3-612.

A plurality of support bridges 3-620 can remain after the machining process that forms the trenches 3-630. The support bridges provide mechanical support for the platform 3-610, and reduce thermal conduction from the platform 3-610 to the baseplate 3-605. In some embodiments, the bridges can be formed from a different material than the platform. In various embodiments, the bridges 3-620 are located centrally, with respect to the thickness of the platform, between upper and lower surfaces of the platform 3-610, as depicted in FIG. 3-6B. For example, the bridges 3-620 can be located in a neutral mechanical plane of the baseplate 3-605 as illustrated in FIG. 3-6B. Locating the bridges 3-620 centrally with respect to the thickness of the platform and baseplate can reduce the amount of out-of-plane thermal-mechanical stress imparted between the baseplate body 3-605 and platform 3-610. Reducing the amount of heat dissipated into the baseplate and reducing out-of-plane stress can reduce warping of the baseplate and undesired relative motion of other optical components in the laser cavity. In some embodiments, the bridges comprise flexural members that allow the platform to move in-plane relative to the baseplate 2-105, e.g., to accommodate thermo-mechanical stresses induced by the platform. Motion of some laser components (e.g., the gain medium 1-105) may not affect operation of the laser as much as other components (e.g., cavity mirrors), and therefore can be tolerated. The partial thermo-mechanical isolation of the platform 3-610 can improve the stability of the laser, and reduce the need for adjustments by a skilled operator.

According to some embodiments, one or more platforms 3-610 can be used to support high temperature components in a mode-locked laser. For example, a first platform 3-610 can be used to support a diode pump source, and a second platform can be used to support a laser's gain medium. In some implementations, a third platform can be used to support frequency-doubling component (e.g., a non-linear crystal).

Although the laser cavity described above indicates that the gain medium is a neodymium vanadate crystal, other types of materials can be used to obtain lasing and mode locking at other wavelengths. Correspondingly, different pump sources can be used to provide pump wavelengths suitable for exciting the gain medium. According to some embodiments, a pump wavelength $\lambda_p$ for a compact laser module can be between 390 nm and approximately 1100 nm. A mode-locked lasing wavelength $\lambda_1$ for a compact laser module can be between 750 nm and 1500 nm. In some cases, an output wavelength $\lambda_2$ for a compact laser module can be frequency doubled and can be between 325 nm and 750 nm. The frequency-doubling element 3-109 can be KTP, LBO or BBO in some implementations. In some cases, an output wavelength $\lambda_2$ can be between 500 nm and 700 nm. An output pulse duration at the fundamental wavelength $\lambda_1$ or the frequency-doubled wavelength $\lambda_2$ can be between 1 picosecond and 100 picoseconds, according to some embodiments. In some cases, the output pulse duration can be between 10 picoseconds and 30 picoseconds.

As alternative examples, if a green output wavelength is desired, the gain medium may be Nd:YAG, or Nd:YLF, which lase at 1064 nm and 1053 nm, respectively. In some embodiments, Cr:Forsterite may be used as a gain medium, which can lase at 1280 nm and be frequency doubled to 640 nm (in the red region of the optical spectrum). In some embodiments, Pr:LiYF$_4$ may be used as the gain medium and lase at 640 nm (in the red) directly, without frequency doubling. The inventors have recognized and appreciated that Nd:YVO$_4$ may be used as a gain medium to lase at one or two wavelengths 1064 nm and/or 1342 nm, which can be doubled to 532 nm (green) and/or 671 nm (red). The inventors have also recognized and appreciated that sum-frequency generation can be performed in a nonlinear crystal to obtain additional wavelengths. For example, pulses at the two lasing wavelengths from Nd:YVO$_4$ can be mixed in a nonlinear crystal to produce radiation at approximately 594 nm. Other gain media include, but are not limited to ytterbium-doped YAG (Yb:YAG), ytterbium-doped glass (Yb:glass), erbium-doped YAG (Er:YAG), and titanium-doped sapphire (Ti:sapphire).

Pump Source and Module

To excite the gain medium 1-105 and initiate mode-locked operation of the laser, continuous-wave radiation (indicated by the black dotted line in FIG. 2-1 and FIG. 4-1) from a high-power laser diode can be focused into the gain medium using a coupling lens 2-142. The optical power from the laser diode can be between 1 Watt and 20 Watts, which are power levels associated with significant electrical and optical heat generation. Such heat generation, if allowed to dissipate in the base chassis 2-105 could adversely affect stability of the mode-locked laser module 1-108. The laser diode can be mounted in a pump module 2-140 that is mounted in a through-hole 2-145 in the base chassis 2-105 in a way that reduces heat conduction from the pump module to the base chassis and helps thermally isolate the pump module 2-140 from the base chassis 2-105.

An example of a pump module 2-140 is depicted in FIG. 4-1, according to some embodiments. The pump module can seal the laser diode 4-130 in a closed housing 4-110, provide heat dissipation for the laser diode, and include an adjustable head 4-120 that can align the pump beam to an optical axis of the mode-locked laser cavity. An example of a laser diode pump source that can be used in a pump module is laser diode model FL-FM01-10-808 available from FocusLight Corporation of Xi'an, Shaanxi, China. In some embodiments, the laser diode 4-130 can be mounted in an F mount or C mount within the pump module 2-140.

According to some embodiments, the pump-module housing 4-110 can attach securely to the base chassis 2-105 with screws and/or stand-off posts 4-152 that have low thermal conductivity (e.g., stainless steel, nylon, hard plastic). Part of the housing 4-110 can protrude from a back side of the base chassis 2-105, and part of the housing can extend through a through hole 2-145 in the base chassis 2-105. The gaps between the pump-module housing 4-110 and base chassis 2-105 and the low-thermal-conductivity screws or fasteners help to thermally isolate the pump module 2-140 from the base chassis 2-105 and maintain stability of the mode-locked laser 1-110. The adjustable head 4-120 can similarly attach to the housing 4-110 with screws 4-154 having a low thermal conductivity. The housing can have heat-dissipating fins 4-124 machined into the body to aid in heat extraction from the laser diode 4-130. A fan (not shown) can be mounted nearby or mounted to the housing 4-110 to further aid in heat removal. According to some embodiments, the laser diode 4-130 can be mounted on a thermo-electric cooler (TEC) 4-160 that allows thermal control and temperature stabilization of the laser diode 4-130. In some implementations, a PCB 4-170 that includes circuitry for connecting to and operating the laser diode 4-130 and/or TEC can attach to the housing 4-110 and form a cover that helps seal the laser diode 4-130 from exposure to external dust and humidity.

According to some embodiments, the pump module 2-140 can be located within about 30 mm of an edge of the base chassis 2-105, and the dissipated heat directed toward the edge and away from the base chassis by a fan, for example. The base chassis 2-105 can serve additionally as a wind screen, protecting the laser optics and laser cavity on one side of the base chassis from air flow or turbulence on the reverse side of the plate where heat is removed. In embodiments, the mounting of the pump-module housing 4-110 as described allows it to be located near the gain medium 1-105 of the mode-locked laser, which helps improve stability of the location of the pump beam 4-135 within the gain medium (improving mode-locking stability) and also helps provide a compact mode-locked laser module 1-108.

The pump-module housing 4-110 can also include beam collimating optics, according to some embodiments. A fast-axis collimator (FAC) 4-142 can be located near or integrated within the laser diode. In some cases, this collimater can comprise a cylindrical lens or pair of crossed cylindrical lenses. In some embodiments, the FAC 4-142 can comprise a single cylindrical lens and can have a short focal length (e.g., less than about 5 mm). In some implementations, the FAC 4-142 can comprise a length of optical fiber having a diameter less than about 150 microns, and its focal length can be less than 500 microns. The FAC 4-142 can be configured to provide a beam for the laser diode that has approximately equal divergence in orthogonal transverse directions between 5 degrees and 15 degrees. In some embodiments, a beam from the laser diode 4-130 and FAC 4-142 can have a rectangular or square cross section (e.g., corresponding to an array of emitters).

The pump-module housing 4-110 can further include a collimating lens 4-144 that collimates the laser diode pump beam. According to some embodiments, this lens can be a plano-convex lens with both surfaces anti-reflection coated for the pump wavelength $\lambda_p$. The planar surface of the lens can face the diode 4-130. The focal length of the collimating lens 4-144 can be between 15 mm and 35 mm. The collimating lens 4-144 can be spaced from the FAC lens 4-142 by a distance approximately equal to the back focal length of the collimating lens 4-144, according to some implementations.

A collimated, or nearly collimated, beam from the pump-module housing 4-110 can be reflected by a dichroic mirror 4-146 that is mounted in the adjustable pump head 4-120. The dichroic mirror 4-146 can include a multilayer coating that reflects the pump wavelength toward the coupling lens 2-142 and gain medium 1-105 (not shown in FIG. 4-1) and transmits mode-locked pulses at the lasing wavelength from the mode-locked laser cavity. Since the pump head 4-120 is adjustable with adjustment screws 4-154, the dichroic mirror can be pitched (rotated about an axis parallel to the X axis shown in the drawing) and rolled (rotated about an axis parallel to the Z axis) to adjust the position of the pump beam within the gain medium.

According to some implementations, the location of the dichroic mirror 4-146 at which the pump beam 4-135 from the laser diode 4-130 is incident on the mirror 4-146 is positioned approximately at the focal length of the coupling lens 2-142. Because of this positioning, angular adjustments to the dichroic mirror 4-146, which deviate the outgoing pump beam 4-135, result in primarily parallel beam-path displacements of the pump beam through the gain medium 1-105. This can be understood since rays going from a focal point at the dichroic mirror 4-146 through the coupling lens 2-142 will emerge from the coupling lens as parallel rays. Accordingly, the dichroic mirror 4-146 can be adjusted to primarily translate the pump beam in X and Y directions (referring to FIG. 4-1 and FIG. 2-1) in the gain medium with minimal change to the angle of the pump beam through the gain medium 1-105. In view of this effect, pitch adjustments to the dichroic mirror 4-146 result in pump-beam displacements in the Y direction at the gain medium and roll adjustments to the dichroic mirror provide X-directed (and some Y-directed) pump-beam displacements in the gain medium 1-105. A change in angle of the pump beam 4-135 through the gain medium 1-105 can be undesirable because it can reduce the overlap volume of the pump beam 4-135 with the mode-locked laser beam in the gain medium 1-105.

To simplify assembly and reduce the number of adjustable screws on the pump head 4-120, the adjustable head can be attached to the housing 4-110 with a three-point contact, adjustable, kinematic mounting scheme. The head 4-120 can be drawn or forced toward the housing 4-110 using at least one resilient spring 4-157 (as depicted in FIG. 4-2A and FIG. 4-2B). One of the three-point contacts can be a ball-and-cone that allows all rotational degrees of freedom of the head. For example, a ball-shaped contact feature 4-155 (e.g., a ball bearing) may be located on a side of the head 4-120 near the pump-housing module 4-110. The ball-shaped contact feature 4-155 may be received by a cone-shaped recess. The remaining two points of contact can be adjustment screws 4-154a, 4-154b. One of these screws 4-154a can have a ball-shaped end that is received in a groove to restrict yaw motion of the head. The other screw 4-154b can have a ball-shaped end that is received on a flat surface. In some implementations, after the adjustment screws 4-154a, 4-154b have been set to align the pump beam 4-135 through the gain medium 1-105, at least one counter-force screw 4-158 can be tightened to lock the adjustable head in place.

In some implementations, a focal length of the coupling lens 2-142 can be between about 20 mm and about 30 mm. The lens can be plano-convex in some embodiments, though a double convex lens can be used in some cases. The coupling lens can have anti-reflection coatings on both sides for the pump wavelength and mode-locked laser wavelength. Additionally, the coupling lens 2-142 can be oriented at an angle between 1 degree and 4 degrees with respect to the optical axis 2-111 of the mode-locked laser (referring to FIG. 2-1) to avoid reflections from the faces that would return into the laser cavity and the laser diode. In some implementations, the gain medium 1-105 is located approximately a back-focal length away from the coupling lens 2-142. Unabsorbed pump radiation can pass through a laser-cavity folding mirror 2-115 and be absorbed in a beam dump and/or detected by a photodetector 2-116, according to some embodiments.

In some implementations, the FAC 4-142, collimating lens 4-144, and coupling lens 2-142 are arranged to provide approximately 1-to-1 imaging of an output from the laser diode 4-130 into the gain medium 1-105. The image of the laser diode's output (e.g., emitter array) in the gain medium should approximately match the mode-locked laser's intracavity beam waist size in the gain medium. The mode-locked laser's beam waist size in the gain medium can be determined predominantly by a focal length of curved mirror 2-117, its distance from the output coupler 1-111, and a distance of the gain medium 1-105 from the output coupler. For the configurations described above and with 1-to-1 imaging, the imaged emitter size of the laser diode in the gain medium should be between 100 microns and 150 microns. The inventors have observed that emitter sizes between 90 microns and 220 microns provide mode-locked lasing, though the small emitter size is more susceptible to rapid degradation and the larger emitter size can cause the mode-locked laser to lase in higher order spatial modes. Additionally, the polarization of radiation should be well matched to the intended lasing polarization of the mode-locked laser 1-110. In this regard, the pump module 2-140 and/or the mode-locked laser module 1-108 can include one or more optical components (e.g., quarter-wave plate, half-wave plate) that can be rotated or adjusted to control the state of polarization of the pump radiation on the gain medium 1-105. The polarization can be controlled to increase lasing efficiency and output power from the mode-locked laser 1-110.

Other excitation sources can be used to pump the gain medium 1-105 in other embodiments, and the invention is not limited to laser diodes. In some embodiments, a fiber or fiber-coupled laser (not shown) can be used to pump the gain medium 1-105 of the mode-locked laser 1-110. A fiber laser can comprise an active optical fiber as part of the fiber-laser cavity that is pumped by one or more laser diodes. A fiber-coupled laser can comprise one or more laser diodes having their outputs coupled into an optical fiber. An output beam from a fiber carrying optical energy from the fiber laser or fiber-coupled laser can be directed to and focused into the gain medium using the same or similar optics that are used for a laser diode pump source. An optical beam from a fiber can have a more circular, homogenous, and/or Gaussian (or top-hat-shaped) spatial profile than a beam directly from a high-power laser diode pump source. A fiber laser pump source may or may not be mounted on a fixture other than base chassis 2-105 in some embodiments, and an end of the fiber carrying pump energy can be attached to a mount on the mode-locked laser module 1-108 that is located on the same side or opposite side of the base chassis as the gain medium 1-105.

Cavity Alignment

As may be appreciated, alignment of the mode-locked laser-cavity optics can be difficult because of the high number of mirrors and optical components in the laser cavity. In some embodiments and referring again to FIG. 2-1, a mode-locked laser can include mounting features 2-110 (e.g., screw holes and/or registration features) located along the optical axis of the laser cavity between the gain medium 1-105 and second curved mirror 2-127. The mounting features 2-110 can be configured to receive an optical mount in which a second output coupler (not shown in FIG. 2-1) can be mounted. When the optical mount and second output coupler are in place, the laser can be aligned to lase in continuous-wave mode with a shortened laser cavity. The second output coupler can transmit a small amount of power (e.g., between 2% and 20%), and provide a laser beam that can be used to align optical components of the laser between the inserted optical mount and the SAM 1-119. Once these remaining components are aligned, the inserted optical mount can be removed, so that the laser 1-110 can be tuned to operate in pulsed mode with the full cavity length.

The inventors have discovered that a second output coupler (not shown in FIG. 2-1) for short cavity alignment can be mounted near the gain medium 1-105 and before the turning mirror 2-115. According to some embodiments, thermal lensing in the gain medium, when pumped at optical powers that enable mode-locked operation of the mode-locked laser 1-108, supports lasing in the shortened cavity and provides a stable lasing cavity without the need for an additional lensing element in the shortened cavity, even though the length of the shortened cavity is less than half the length of the mode-locked laser cavity. In some cases, the length of the shortened cavity can be less than one-quarter or even one-eighth the length of the mode-locked laser cavity. Accordingly, a second output coupler placed near the gain medium 1-105 can enable easy and rapid alignment of all optical elements from the turning mirror 2-115 to the SAM 1-119. In a configuration with an output coupler mounted before the turning mirror 2-115 and no other lensing element in the shortened laser cavity, it can be helpful to have thermal lensing in the gain medium of at least 2 diopters to obtain lasing and make alignment of the shortened cavity easier, though in some cases continuous wave lasing can occur without thermal lensing (0 diopters).

Frequency Doubling

Referring again to FIG. 2-1, an output of a mode-locked laser 1-110 can be focused through a lens 2-164 into a frequency-doubling crystal 2-170 to halve the optical wavelength (or double the optical frequency) of the output pulses. For example, the mode-locked laser 1-110 can produce pulses with a characteristic wavelength of about 1064 nm, and the frequency-doubling crystal 2-170 can convert the wavelength to about 532 nm. The frequency-doubled output can be provided to a bio-optoelectronic chip 1-140 and used there to excite fluorophores having different emission characteristics. Components for frequency doubling and control of the frequency-doubled power can be mounted within the compact mode-locked laser module 1-108, according to some embodiments.

The lens 2-164 can have a focal length between 15 mm and 30 mm, and include antireflection coatings on both surfaces to minimize reflections of the lasing wavelength. The lens can produce a beam waist for the mode-locked pulses between 15 microns and 35 microns in the frequency-doubling crystal.

The frequency-doubling crystal 2-170 can be a potassium titanyl phosphate (KTP), type II crystal. The crystal length can be between 3 mm and 7 mm. According to some embodiments, the frequency-doubling crystal 2-170 is a high grey track resistant (HGTR) crystal. The inventors observed that flux grown crystals can degrade for high average powers at green wavelengths. For the HGTR crystals, the cut angles can be between 24 degrees and 25 degrees for phi and between 89 degrees and 91 degrees for theta. Both facets of the crystal can be coated with anti-reflection coatings for the lasing wavelength and the doubled wavelength. According to some implementations, the frequency-doubling crystal 2-170 is mounted against a self-aligning surface formed in the base chassis 2-105. A collimating lens (not shown in FIG. 2-1) can be placed after the frequency-doubling crystal to collimate the frequency-doubled radiation from the crystal.

In some embodiments, a half-wave plate 2-160 can be mounted in a rotatable mount with its rotation angle controlled by an actuator 2-162. The half-wave plate can be located in the output optical path of the mode-locked laser before the frequency-doubling crystal 2-170. According to some embodiments, an actuator 2-162 can comprise a stepper motor, a piezoelectric motor, a galvanometer having precision bearings and configured to rotate an optical component, a DC motor, or any other suitable actuation mechanism. Rotating the half-wave plate 2-160 can alter the polarization of the laser's output pulses and change the second-harmonic conversion efficiency in the frequency-doubling crystal 2-170. Control of the half-wave plate can then be used to control an amount of power at the frequency-doubled wavelength that is delivered to the bio-optoelectronic chip 1-140. By rotating the half-wave plate 2-160 (or the frequency-doubling crystal 2-170), the optical power at the frequency-doubled wavelength $\lambda_2$ can be varied precisely by small amounts over a large range (e.g., over an order of magnitude or more), without affecting the operation of the mode-locked laser at the fundamental wavelength $\lambda_1$. That is, the power at the frequency-doubled wavelength can be altered without affecting the mode-locking stability, thermal dissipation, and other characteristics of the mode-locked laser 1-110. In some embodiments, other adjustments can be used additionally or alternatively to control frequency-doubled power without affecting the fundamental laser operation. For example, an incident angle of the pulsed-laser beam on the frequency-doubling crystal 2-170 and/or distance between the lens 2-164 and frequency-doubling crystal can be controlled in an automated manner to alter and/or maximize the frequency-doubling efficiency.

In some embodiments, the frequency-doubled output pulses can be directed by a turning mirror 2-180 and/or to a beam shaping and steering module. The turning mirror 2-180 can be dichroic, such that it transmits optical radiation which has not been down-converted by the frequency-doubling crystal 2-170 to a beam dump (not shown). In some implementations, the turning mirror 2-180 can transmit a small amount of the frequency-doubled output to a photodiode 2-182. A wavelength selective filter can be placed in front of the photodiode 2-182 to block or reflect the fundamental wavelength. An output from the photodiode 2-182 can be provided to the PCB 2-190 where the signal can be processed to evaluate mode-locking stability and/or produce a control signal for rotating the half-wave plate 2-160 to maintain a stable output power. In some implementations, the photodiode 2-182 can be mounted on the PCB 2-190 and the frequency-doubled output can be reflected, scattered, coupled via an optical fiber, or otherwise directed to the photodiode through a hole and/or window in the base chassis 2-105.

In some implementations, a beam shaping and steering module as described in a separate U.S. patent application No. 62/435,679, filed Dec. 16, 2016 and titled "Compact Beam Shaping and Steering Assembly" can be assembled on the baseplate or mounted adjacent to the base chassis 2-105. An output beam from the laser module can be provided to the beam shaping and steering assembly to adapt the output beam at the fundamental wavelength or frequency-doubled wavelength for use in an analytic system 1-160.

Clock Generation and System Control

Referring again to FIG. 1-1, regardless of the method and apparatus that is used to produce short or ultrashort-pulses, a portable analytic instrument 1-100 can include circuitry configured to synchronize at least some electronic operations (e.g., data acquisition and signal processing) of an analytic system 1-160 with the repetition rate of optical pulses 1-122 from the mode-locked laser 1-110. For example, when evaluating fluorescent lifetime in a bio-optoelectronic chip 1-140, it is beneficial to know the time of excitation of a sample accurately, so that timing of emission events can be correctly recorded. According to some embodiments, a timing signal can be derived from the optical pulses produced by the mode-locked laser, and the derived timing signal can be used to trigger instrument electronics.

The inventors have recognized and appreciated that coordination of operation of the mode-locked laser 1-110 (e.g., to deliver excitation optical pulses to reaction chambers 1-330), signal-acquisition electronics (e.g., operation of time-binning photodetectors 1-322), and data read-out from the bio-optoelectronic chip 1-140 poses technical challenges. For example, in order for the time-binned signals collected at the reaction chambers to be accurate representations of fluorescent decay characteristics, each of the time-binning photodetector 1-322 must be triggered with precise timing after the arrival of each excitation optical pulse at the reaction chambers. Additionally, data must be read from the bio-optoelectronic chip 1-140 in approximate synchronicity with data acquisition at the reaction chambers to avoid data overruns and missed data. Missed data could be detrimental in some cases, e.g., causing a misrecognition of a gene sequence. The inventors have recognized and appreciated that system timing is further complicated by the natural operating characteristics of passively mode-locked lasers, e.g., prone to fluctuations in pulse amplitude, fluctuations in pulse-to-pulse interval T, and occasional pulse drop-outs.

Figures 1, 2, 3, 4, 5:
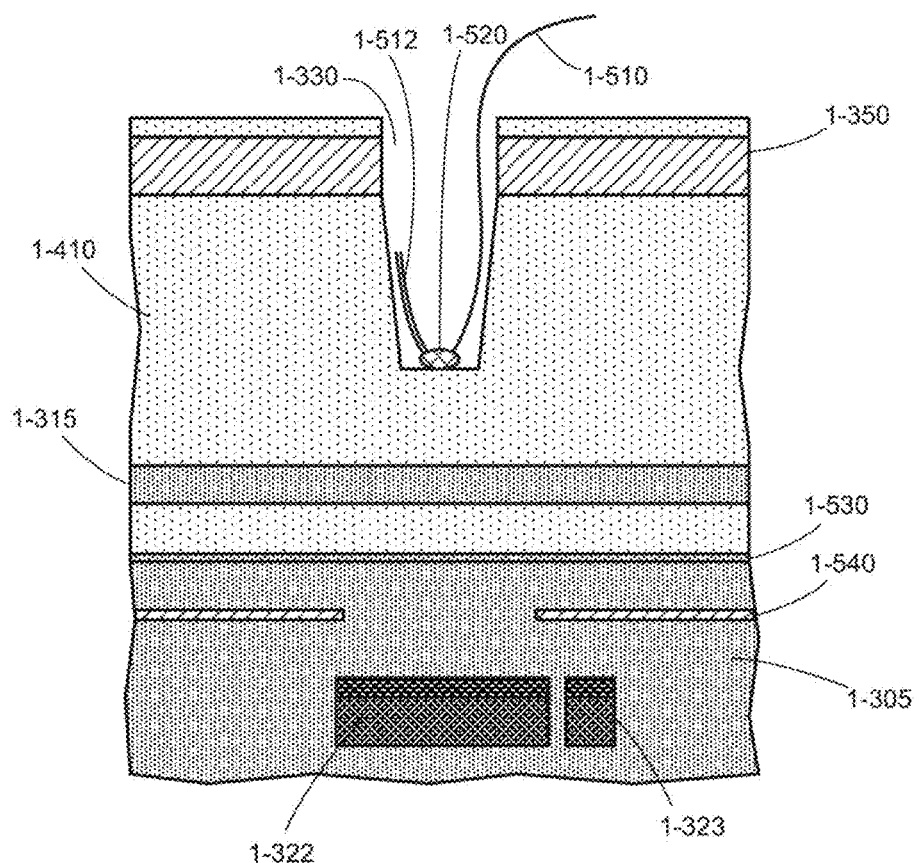
Figures 1, 2, 3, 4, 5, 6:
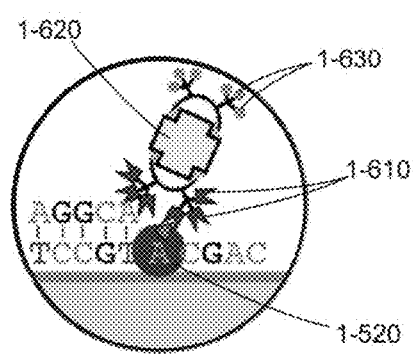
Figures 1, 2, 3, 4, 5, 6, 7:
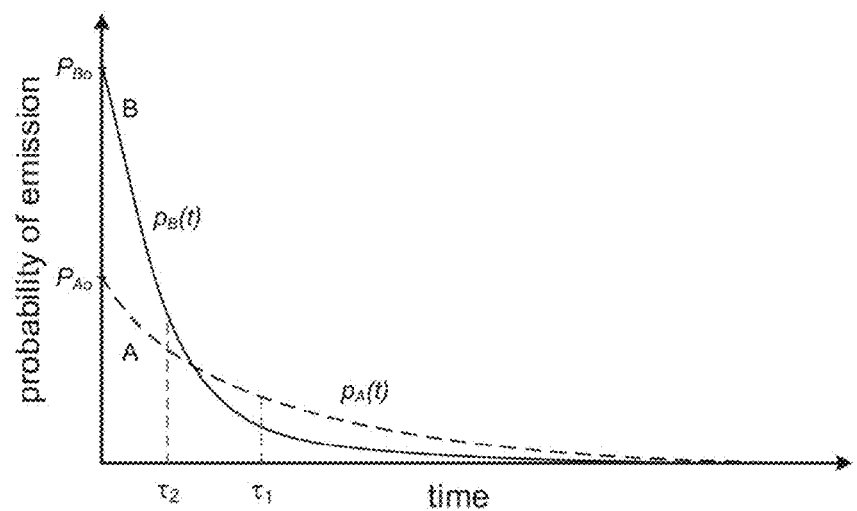
Figures 1, 2, 3, 4, 5, 6, 7, 8:
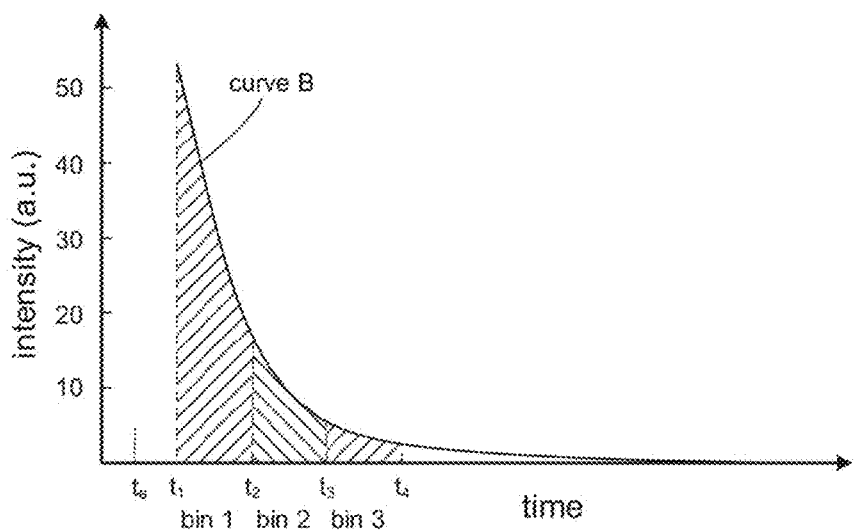
Figures 1, 2, 3, 4, 5, 6, 7, 8, 9:
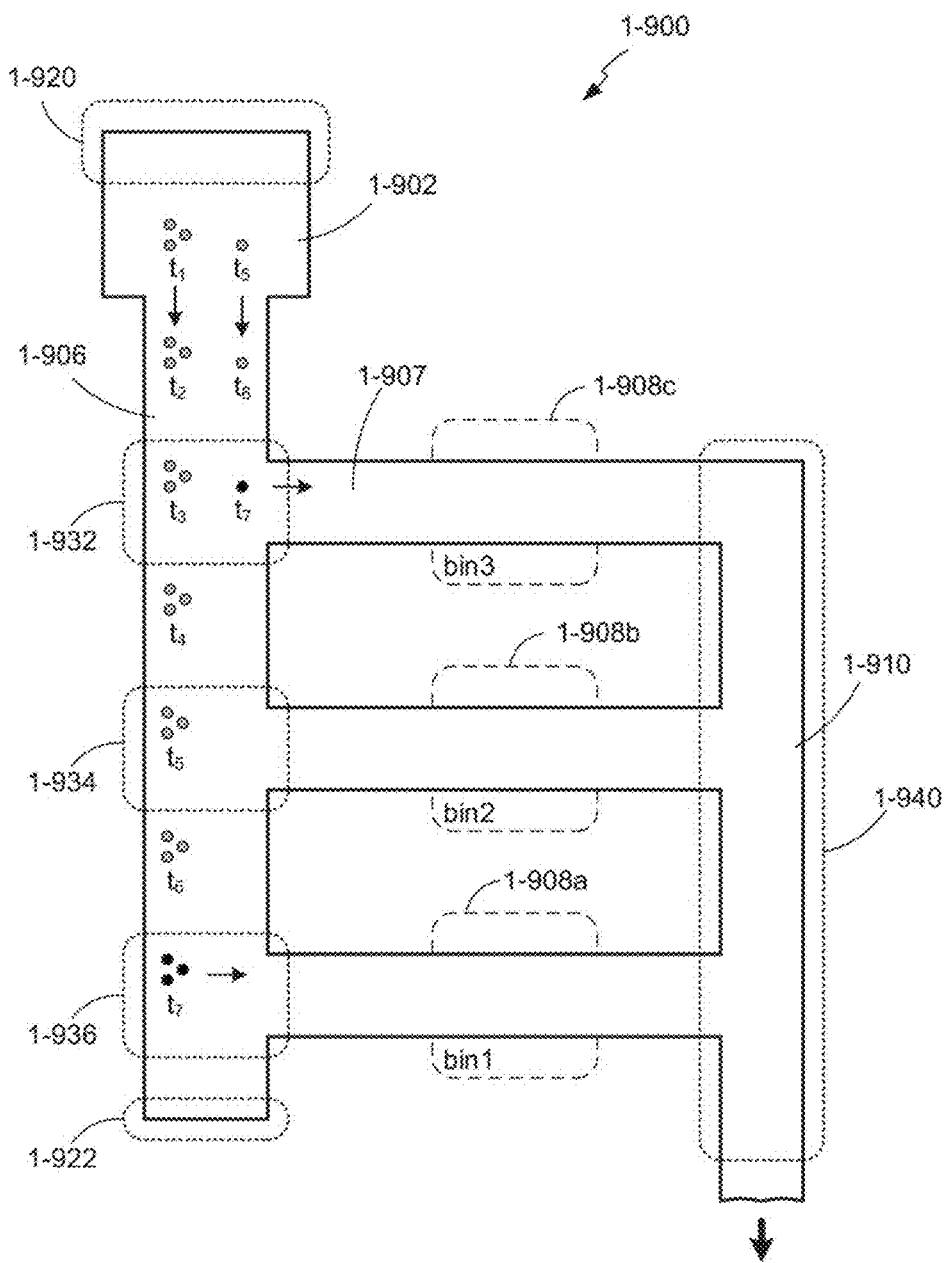
Figures 1, 2:
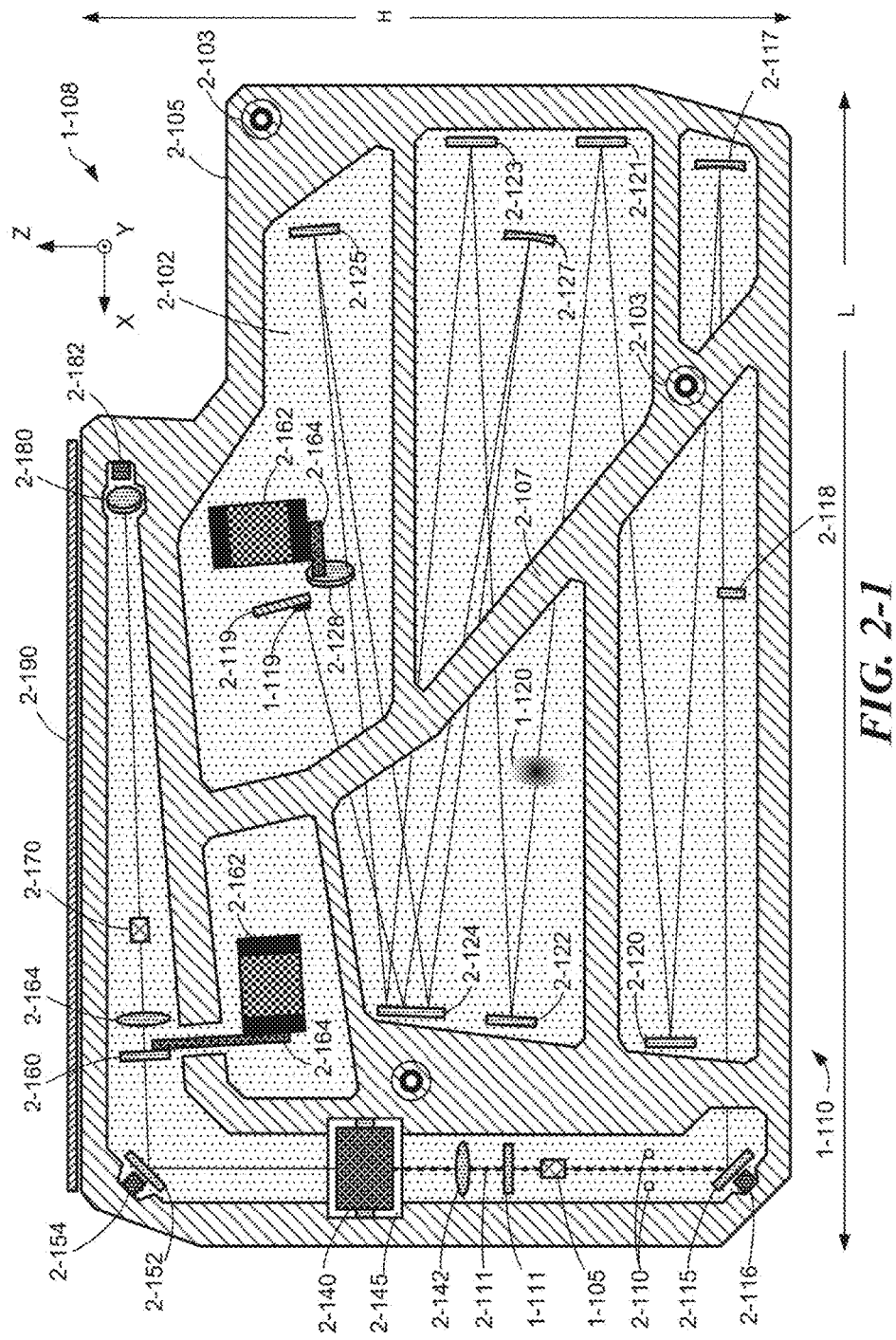

FIG. 5-1 depicts a system in which a timer 5-120 provides a synchronizing signal to the analytic system 1-160. In some embodiments, the timer 5-120 can produce a clock signal that is synchronized to optical pulses produced by the pulsed optical source 1-110, and provide the clock signal to the analytic system 1-160. In FIG. 5-1, the optical pulses 1-120 are depicted spatially as being separated by a distance D. This separation distance corresponds to the time T between pulses according to the relation T=D/c where c is the speed of light. In practice, the time T between pulses can be determined with a photodiode and oscilloscope. According to some embodiments, $T=1/f_{sync}N$ where N is an integer greater than or equal to 1 and $f_{sync}$ represents the frequency of a generated clock signal. In some implementations, $T=N/f_{sync}$ where N is an integer greater than or equal to 1.

According to some embodiments, the timer 5-120 can receive an analog or digitized signal from a photodiode that detects optical pulses from the pulse source 1-110. The photodiode 2-154 can be mounted on the base chassis 2-105 and can be a high-speed InGaAs photodiode. The timer 5-120 can use any suitable method to form or trigger a synchronizing signal from the received analog or digitized signal. For example, the timer can use a Schmitt trigger or comparator to form a train of digital pulses from detected optical pulses. In some implementations, the timer 5-120 can further use a delay-locked loop or phase-locked loop to synchronize a stable clock signal from a stable electronic clock source to a train of digital pulses produced from the detected optical pulses. The train of digital pulses or the locked stable clock signal can be provided to the analytic system 1-160 to synchronize electronics on the instrument with the optical pulses.

The inventors have conceived and developed clock-generation circuitry that can be used to generate a clock signal and drive data-acquisition electronics in a portable instrument 1-100. An example of clock-generation circuitry 5-200 is depicted in FIG. 5-2. The clock generation circuitry can be included on a PCB 2-190 mounted on the base chassis 2-105. According to some embodiments, clock-generation circuitry can include stages of pulse detection, signal amplification with automatic gain control, clock digitization, and clock phase locking.

A pulse-detection stage can comprise a high-speed photodiode 5-210 that is reversed biased and connected between a biasing potential and a reference potential (e.g., a ground potential), according to some embodiments. A reverse bias on the photodiode can be any suitable value, and can be fixed using fixed-value resistors or can be adjustable. In some cases, a capacitor C can be connected between a cathode of the photodiode 5-210 and a reference potential. A signal from the anode of the photodiode can be provided to an amplification stage. In some embodiments, the pulse detection stage can be configured to detect optical pulses having an average power level between about 100 microwatts and about 25 milliwatts. The pulse-detection stage of the clock-generation circuitry 5-200 can be mounted on or near the mode-locked laser 1-110, and arranged to detect optical pulses from the laser.

An amplification stage can comprise one or more analog amplifiers 5-220 that can include variable gain adjustments or adjustable attenuation, so that pulse output levels from the analog gain amplifiers can be set within a predetermined range. An amplification stage of the clock-generation circuitry 5-200 can further include an automatic gain control amplifier 5-240. In some cases, analog filtering circuitry 5-230 can be connected to an output of the analog amplifiers 5-220 (e.g., to remove high-frequency (e.g., greater than about 500 MHz) and/or low-frequency noise (e.g., less than about 100 Hz)). The filtered or unfiltered output from the one or more analog gain amplifiers 5-220 can be provided to an automatic gain control amplifier 5-240, according to some embodiments.

According to some embodiments, a final output signal from the one or more analog amplifiers can be positive-going. The inventors have recognized and appreciated that a subsequent automatic gain-control (AGC) amplifier operates more reliably when it input pulses to positive voltage rather than negative voltage. The automatic gain control amplifier can vary its internal gain to compensate for amplitude fluctuations in the received electronic pulse train. The output pulse train from the automatic gain control amplifier 5-240 can have approximately constant amplitude, as depicted in the drawing, whereas the input to the automatic gain control amplifier 5-240 can have fluctuations in the pulse-to-pulse amplitudes. An example automatic gain control amplifier is model AD8368 available from Analog Devices, Inc. of Norwood, Mass.

In a clock digitization stage, an output from the automatic gain control amplifier can be provided to a comparator 5-250 to produce a digital pulse train, according to some implementations. For example, the pulse train from the AGC can be provided to a first input of the comparator 5-250, and a reference potential (which can be user-settable in some embodiments) can be connected to a second input of the comparator. The reference potential can establish the trigger point for the rising edge of each produced digital pulse.

As may be appreciated, fluctuations in optical pulse amplitude would lead to fluctuations in amplitudes of the electronic pulses before the AGC amplifier 5-240. Without the AGC amplifier, these amplitude fluctuations would lead to timing jitter in the rising edges of pulses in the digitized pulse train from the comparator 5-250. By leveling the pulse amplitudes with the AGC amplifier, pulse jitter after the comparator is reduced significantly. For example, timing jitter can be reduced to less than about 50 picoseconds with the AGC amplifier. In some implementations, an output from the comparator can be provided to logic circuitry 5-270 which is configured to change the duty cycle of the digitized pulse train to approximately 50%.

A phase-locking stage of the clock-generation circuitry 5-200 can comprise a phase-locked loop (PLL) circuit 5-280 that is used to produce one or more stable output clock signals for timing and synchronizing instrument operations. According to some embodiments, an output from the clock digitization stage can be provided to a first input (e.g., a feedback input) of a PLL circuit 5-280, and a signal from an electronic or electro-mechanical oscillator 5-260 can be provided to a second input (e.g., a reference input) to the PLL. An electronic or electro-mechanical oscillator can be highly stable against mechanical perturbations and against temperature variations in some cases. According to some embodiments, a phase of the stable clock signal from the electronic or electro-mechanical oscillator 5-260 is locked, by the PLL, to a phase of the digitized clock signal derived from the mode-locked laser, which can be less stable. In this manner, the electronic or electro-mechanical oscillator 5-260 can ride through short-term instabilities (e.g., pulse jitter, pulse drop outs) of the mode-locked laser 1-110, and yet be approximately synchronized to the optical pulse train. The phase-locked loop circuit 5-280 can be configured to produce one or more stable output clock signals that are derived from the phase-locked signal from the electro or electro-mechanical oscillator 5-260. An example circuit that can be used to implement the PLL is IC chip Si5338, which is available from Silicon Laboratories Inc. of Austin, Tex.

According to some embodiments, one or more clock signals output from the PLL circuit 5-280 can be provided to the bio-optoelectronic chip 1-140 to time data-acquisition electronics on the chip. In some cases, the PLL circuit 5-280 can include phase adjustment circuitry 5-282, 5-284 on its clock outputs, or separate phase adjustment circuits can be connected to clock outputs of the phase-locked loop. In some implementations, the bio-optoelectronic chip 1-140 can provide a pulse-arrival signal 1-142 from one or more photodetectors on the chip that indicate the arrival of optical excitation pulses from the mode-locked laser 1-110. The pulse-arrival signal can be evaluated and used to set the phase or phases of clock signals provided to the bio-optoelectronic chip 1-140. In some embodiments, the pulse-arrival signal can be provided back to the phased-locked loop circuit 5-280 and processed to automatically adjust the phase of the clock signal(s) provided to the chip, so that a trigger edge of a clock signal provided to drive data-acquisition on the bio-optoelectronic chip 1-140 (e.g., timing of signal acquisition by the time-binning photodetectors 1-322) is adjusted to occur at a predetermined time after the arrival of an optical excitation pulse in the reaction chambers.

According to some embodiments, a clock signal from the PLL circuit 5-280 can also be provided to one or more field-programmable gate arrays (FPGAs) 5-290 included in the instrument 1-100. The FPGAs can be used for various functions on the instrument, such as driving data read out from the bio-optoelectronic chip 1-140, data processing, data transmission, data storage, etc.

The inventors have recognized and appreciated that there can be an interplay between the loop bandwidth of the AGC amplifier 5-240 and the loop bandwidth of the phase-locked loop 5-290. For example, if the loop bandwidth of the phase-locked loop is too high, the PLL can respond to jitter introduced by the AGC amplifier and comparator in the digitized pulse train, and not accurately track the optical pulse timing. On the other hand, if either or both of the AGC and PLL loop bandwidths are too low, the resulting clock signals output from the PLL will not accurately track the optical pulse timing. The inventors have found that an integration time constant associated with the loop bandwidth of the PLL 5-290 should be between about 30 pulses and about 80 pulses of the optical pulse train from the mode-locked laser 1-110. Additionally, an integration time constant associated with the loop bandwidth of the AGC amplifier 5-240 should not exceed by more than about 20% the integration time constant for the PLL.

In some implementations, one or more signals from the amplification stage can be used for additional purposes in the instrument 1-100. For example, an analog signal 5-232 can be split off prior to the AGC amplifier 5-240 and used to monitor the quality of mode locking in the mode-locked laser 1-110. For example, the analog signal 5-232 can be analyzed electronically in the frequency and/or time domain to detect characteristics that are indicative of the onset of Q-switching by the mode-locked laser. If the characteristics (and onset of Q-switching) are detected, the system can automatically make adjustments to optics within the mode-locked laser (e.g., cavity-alignment optics) to avoid Q-switching, or the system can indicate an error and/or shut down the mode-locked laser.

In some embodiments, an AGC amplifier can provide an output signal 5-242 (analog or digital) that is representative of real-time gain adjustments that are needed to level the amplitudes of the output pulses. The inventors have recognized and appreciated that this output signal 5-242 can be used to evaluate mode-locking quality of the mode-locked laser. For example, its spectrum can be analyzed to detect the onset of Q-switching.

Although clock generation and synchronization has been described using an automatic gain control amplifier and a phase-locked loop, alternative apparatus can be used in other embodiments for which a larger amount of clock jitter (e.g., up to about 300 ps) can be tolerated. In some implementations, an amplifier in the pulse amplification stage can be driven into saturation to provide a rising edge trigger signal. A trigger point for a clock can be set at some value on the rising edge. Because the amplifier saturates, variations in pulse amplitude have less of an effect on the trigger timing than for a non-saturated amplifier. The rising edge can be used to toggle a flip-flop clocking circuit, such as those implemented in field-programmable gate arrays (FPGAs). The falling edge from the saturated amplifier returning back to zero can have appreciably more timing variability, depending on when the output of the amplifier is released from saturation. However, the falling edge is not detected by the flip-flop clocking circuit and has no effect on the clocking.

Many FPGAs include digital delay-lock loops (DLL) which can be used instead of a PLL to lock a stable oscillator to the laser-generated clocking signal from the flip flop. In some embodiments, the receiving flip-flop divides the clocking rate from the optical pulse train by two, which can provide a 50% duty-cycle clock signal to the DLL at one-half the pulse repetition rate. The DLL can be configured to generate a frequency-doubled clock to be synchronized with the optical pulse train. Additional synchronized, higher-frequency clocks can also be generated by the DLL and FPGA.

An example of system circuitry for system control is depicted in FIG. 5-3, according to some embodiments. A pump-module control circuit 5-300 can be assembled on a PCB and mounted to the compact mode-locked laser module 1-108 (e.g., mounted on a back side of the module 1-108 shown in FIG. 2-1). The pump-module control circuit 5-300 can interface with a system board 5-320 and a clock-generation and laser-sensing circuit 5-350 (e.g., PCB 2-190) that is mounted on the laser module 1-108. In some implementations, the pump-module control circuit 5-300 and clock-generation and laser-sensing circuit 5-350 can be assembled on a same PCB. In other implementations, the pump-module control circuit 5-300, clock-generation and laser-sensing circuit 5-350, and system control circuitry can be assembled on a same PCB, so that a separate system board 5-320 is not used.

The system board 5-320 can include a central processor (e.g., a microcontroller or microprocessor) that coordinates operation of the system in which the laser module 1-108 is mounted. The system board 5-320 can further include power distribution circuitry and data handling circuitry (e.g., memory, transceiver, network interface board, etc.).

In some embodiments, the pump-module control circuit 5-300 can include a current source 5-332 configured to supply current to the laser diode 4-130 that is used to pump the gain medium 1-105. The current source 5-332 can be controlled via the system board 5-320, according to some embodiments. The pump-module control circuit 5-300 can further include temperature sensing circuitry 5-341 that can connect to a temperature sensor or thermistor (not shown) on the laser diode 4-130. Output from the temperature sensing circuitry 5-341 can be provided to temperature controlling circuitry 5-343, which can drive a TEC 4-160 on which the laser diode 4-130 is mounted. The temperature controller can receive control signals from the system board 5-320 for adjusting and/or stabilizing a temperature of the laser diode 4-130, according to some embodiments.

In some implementations, the pump-module control circuit 5-300 can include one or more actuator control circuits (two shown) 5-351, 5-352. The actuator control circuits can receive control signals from the system board 5-320 to operate one or more actuators located on the mode-locked laser module 1-108. For example, a first actuator control circuit 5-351 can be configured to operate a first actuator 2-162 that rotates a laser window 2-128 in the laser cavity of the mode-locked laser 1-110. Operation of the first actuator can adjust cavity alignment and be used to improve mode locking of the laser 1-110. A second actuator control circuit 5-352 can be configured to operate a second actuator 2-162 that rotates a half-wave plate 2-160 on the laser module 1-108, for example. Rotation of the half-wave plate 2-160 can be used to control an amount of laser power converted to a frequency-doubled wavelength, for example.

According to some embodiments, control signals for the actuator circuits 5-351, 5-352 can be computed on the system board 5-320 based upon outputs from the clock-generation and laser-sensing circuit 5-350. Outputs from the clock-generation and laser-sensing circuit 5-350 can be produced by a fundamental sensor circuit 5-311 (which can include or connect to a photodiode 2-154 configured to sense a fundamental wavelength $\lambda_1$ from the laser 1-110), a frequency-doubled sensor circuit 5-312 (which can include or connect to a photodiode 2-182 configured to sense a frequency-doubled wavelength $\lambda_2$ produced from the laser's output pulses), and a diode pump sensor circuit 5-313 (which can include or connect to a photodiode 2-116 configured to sense a pump wavelength $\lambda_p$ used to excite the gain medium 1-105 in the laser 1-110). Accordingly, feedback control of the mode-locked laser 1-110 and frequency-doubled output power can be implemented by sensing laser operational and output parameters and applying signals via the actuator circuits 5-351, 5-352 that correct or improve operation of the mode-locked laser module 1-108. It will be appreciated that some embodiments can include additional sensor circuits and/or additional actuator control circuits for controlling the same and/or additional components on the compact mode-locked laser module 1-108.

Embodiments of the described technology include the following configurations and methods.

(1) A mode-locked laser module comprising a base chassis; a mode-locked laser having a laser cavity assembled on the base chassis; and a gain medium located in the laser cavity that exhibits a positive thermal lensing value between one diopter and 15 diopters when the mode-locked laser is producing optical pulses.

(2) The mode-locked laser module of configuration (1), further comprising a laser diode arranged to excite the gain medium with a pump beam, wherein absorption of the pump beam in the gain medium causes the thermal lensing.

(3) The mode-locked laser module of configuration (1) or (2), wherein the gain medium comprises a solid state crystal that is disposed in a mount and has no active cooling.

(4) The mode-locked laser module of configuration (2) or (3), wherein the mode-locked laser produces optical pulses stably without mechanical adjustments to the laser cavity for thermal lensing values varied over a range from 8 diopters to 12 diopters due to changes in optical power of the pump beam.

(5) The mode-locked laser module of any of configurations (1) through (4), wherein the mode-locked laser produces optical pulses stably for thermal lensing values varied over a range from one diopter to 15 diopters due to changes in optical power of the pump beam.

(6) The mode-locked laser module of configuration (5), wherein the changes in the optical power of the pump beam are between 2 Watts and 10 Watts and an average output optical power from the mode-locked laser module is between 350 milliwatts and 3.5 watts.

(7) The mode-locked laser module of any of configurations (1) through (6), wherein a pulse repetition rate of the optical pulses is between 50 MHz and 200 MHz and a maximum edge length of the base chassis is not more than 350 mm.

(8) The mode-locked laser module of any of configurations (1) through (7), wherein a pulse repetition rate of the optical pulses is between 50 MHz and 200 MHz and wherein the module has a slab form with a maximum edge length measuring not more than 350 mm and a thickness measuring not more than 40 mm and a weight of the module is no more than 2 kilograms.

(9) The mode-locked laser module of any of configurations (1) through (8), wherein a pulse repetition rate of the optical pulses is between 50 MHz and 200 MHz and wherein a maximum volume occupied by the mode-locked laser module is not more than 0.1 cubic feet.

(10) The mode-locked laser module of any of configurations (1) through (9), wherein a full-width-half-maximum pulse width of the optical pulses is between 9 picoseconds and 38 picoseconds.

(11) The mode-locked laser module of any of configurations (1) through (10), wherein the gain crystal comprises neodymium vanadate (Nd3+:YVO4).

(12) The mode-locked laser module of any of configurations (1) through (11), further comprising a diagonal rib extending diagonally across the chassis that increases torsional stiffness of the chassis, wherein an intracavity beam of the laser cavity passes through multiple openings in the diagonal rib.

(13) The mode-locked laser module of any of configurations (1) through (12), further comprising a saturable absorber mirror mounted on a plate at an end of the laser cavity, wherein the plate is configured to be adjusted with only two degrees of freedom which do not include angle adjustments with respect to an optical axis of an intracavity beam of the laser cavity that is incident on the saturable absorber mirror.

(14) The mode-locked laser module of configuration (13), wherein the plate comprises a printed circuit board having a metal coating or the plate comprises a plate of metal.

(15) The mode-locked laser module of configuration (13) or (14), wherein a first beam waist of the intracavity beam within the gain medium is between 100 microns and 150 microns and a second beam waist of the intracavity beam at the saturable absorber is between 75 microns and 125 microns.

(16) The mode-locked laser module of any of configurations (13) through (15), further comprising a first focusing optic located within the laser cavity; and a laser window or optical flat located within the laser cavity, wherein the first focusing optic and laser window or optical flat are arranged to adjust an incident angle of the intracavity beam on the saturable absorber mirror by rotating the laser window or optical flat.

(17) The mode-locked laser module of any of configurations (13) through (16), further comprising a cavity length extending region located within the laser cavity between the gain medium and the saturable absorber mirror, wherein the cavity length extending region folds the intracavity beam at least four times.

(18) The mode-locked laser module of configuration (17), wherein the cavity length extending region comprises a first reflector; and a second focusing reflector located between the saturable absorber mirror and the gain medium, wherein the first reflector and the second focusing reflector fold the intracavity beam three times on successive reflections.

(19) The mode-locked laser module of configuration (17) or (18), wherein the cavity length extending region comprises a first reflector that folds the intracavity beam multiple times.

(20) The mode-locked laser module of any of configurations (1) through (15), further comprising an output coupler located at a first end of the laser cavity; a saturable absorber mirror located at a second end of the laser cavity; a first focusing optic located within the laser cavity between the gain medium and the saturable absorber mirror; and a second focusing optic located within the laser cavity between the first focusing optic and the saturable absorber mirror.

(21) The mode-locked laser module of configuration (20), wherein an intracavity beam between the first focusing optic and the second focusing optic is essentially collimated.

(22) The mode-locked laser module of configuration (20) or (21), wherein a focal length of the first focusing optic is between 240 mm and 260 mm and a focal length of the second focusing optic is between 240 mm and 260 mm.

(23) The mode-locked laser module of any of configurations (20) through (22), wherein the output coupler is located between 280 mm and 300 mm from the first focusing optic and the gain medium is located between 4 mm and 8 mm from the output coupler.

(24) The mode-locked laser module of any of configurations (1) through (23), further comprising only one mirror located within the laser cavity that provides angular adjustment of the one mirror while the mode-locked laser is operating.

(25) The mode-locked laser module of any of configurations (1) through (24), further comprising a frequency-doubling crystal mounted on the chassis and arranged to double a frequency of an output beam from the laser cavity.

(26) A mode-locked laser module comprising a base chassis; a mode-locked laser having a laser cavity assembled on the base chassis; an output coupler mounted on a first mount at a first end of the laser cavity, wherein the first mount provides no angular adjustment of the output coupler with respect to an optical axis of an intracavity beam that is incident on the output coupler; a saturable absorber mirror mounted on a second mount at a second end of the laser cavity, wherein the second mount provides no angular adjustment of the saturable absorber mirror with respect to the optical axis of the intracavity beam that is incident on the saturable absorber mirror; and a gain medium located between the mode-locked laser and the output coupler.

Configuration (26) can include one or more aspects and features from any of configurations (2) through (25).

(27) A mode-locked laser module comprising a base chassis; an output coupler and a first focusing optic mounted on the base chassis; a saturable absorber mirror and second focusing optic mounted on the base chassis, wherein the output coupler and saturable absorber mirror comprise end mirrors of a laser cavity for the mode-locked laser; a gain medium located along an optical axis of an intracavity beam within the laser cavity; and a cavity length extending region comprising two reflectors located between the output coupler and the saturable absorber mirror, wherein the two reflectors fold the intracavity beam more than two times.

Configuration (27) can include one or more aspects and features from any of configurations (2) through (25).

(28) A mode-locked laser module comprising a base chassis; a mode-locked laser having a first laser cavity configured to operate at a pulse repetition rate between 50 MHz and 200 MHz, wherein the mode-locked laser is assembled on the base chassis; a first end mirror of the first laser cavity located at a first end of the first laser cavity; a second end mirror of the first laser cavity located at a second end of the first laser cavity; and a gain medium located within the first laser cavity, wherein the gain medium is configured to exhibit thermal lensing when pumped at an operating power for the first laser cavity, wherein the thermal lensing supports lasing in a second laser cavity formed within the first laser cavity that is less than one-half the length of the first laser cavity and that includes the first end mirror and a third end mirror that is installed on the base chassis in the first laser cavity.

Configuration (28) can include one or more aspects and features from any of configurations (2) through (25).

(29) A method of operating a mode-locked laser, the method comprising acts of pumping a gain medium of a laser cavity with an optical pump beam, such that the gain medium exhibits thermal lensing having a range of diopter values between 8 diopters and 12 diopters; reflecting an intracavity beam from and output coupler at a first end of the laser cavity and a saturable absorber mirror at a second end of the laser cavity; and producing an output of stable optical pulses over the range of diopter values.

(30) The method of (29), further comprising pumping the gain medium of the laser cavity, such that the gain medium exhibits thermal lensing having a range of diopter values between one diopter and 15 diopters.

(31) The method of (29) or (30), further comprising adjusting an amount of the thermal lensing by tuning a wavelength of the optical pump beam.

(32) The method of any of (29) through (31), further comprising reflecting the intracavity beam from a first focusing reflector and a second focusing reflector located between the gain medium and the saturable absorber mirror.

(33) The method of (32), further comprising adjusting an incident angle of the intracavity beam on the saturable absorber mirror without adjusting an orientation angle of the saturable absorber mirror with respect to a chassis supporting the gain medium, the output coupler, and the saturable absorber mirror.

(34) The method of any one of (29) through (33), further comprising reflecting the intracavity beam from a plurality of mirrors located between the gain medium and the saturable absorber mirror to extend a length of the laser cavity.

(35) The method of (34), further comprising reflecting the intracavity beam between two mirrors of the plurality of mirrors more than two times on immediately successive reflections.

(36) The method of (34) or (35), further comprising applying an aperture to the intracavity beam to suppress higher-order modes.

(37) The method of any one of (29) through (36), wherein the optical pulses have a pulse repetition rate between 50 MHz and 200 MHz and a chassis on which the output coupler and saturable absorber mirror are mounted has an maximum edge dimension no larger than 350 mm.

(38) The method of any one of (29) through (37), wherein pumping the gain medium comprises providing between 2 Watts and 10 Watts of optical power to the gain medium and an average output power from the mode-locked laser module is between 350 milliwatts and 3.5 watts.

(39) The method of any one of (29) through (38), wherein a full-width-half-maximum pulse width of the optical pulses is between 9 picoseconds and 38 picoseconds.

IV. Conclusion

Having thus described several aspects of several embodiments of a mode-locked laser, it is to be appreciated that various alterations, modifications, and improvements will readily occur to those skilled in the art. Such alterations, modifications, and improvements are intended to be part of this disclosure, and are intended to be within the spirit and scope of the invention. While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

For example, embodiments may be modified to include more or fewer optical components in a laser cavity than described above. Moreover, laser cavity configurations may differ from those shown with some laser cavities have more or fewer turns or folds in the optical path.

While various inventive embodiments have been described and illustrated, those of ordinary skill in the art will readily envision a variety of other means and/or structures for performing the function and/or obtaining the results and/or one or more of the advantages described, and each of such variations and/or modifications is deemed to be within the scope of the inventive embodiments described. More generally, those skilled in the art will readily appreciate that all parameters, dimensions, materials, and configurations described are meant to be examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure may be directed to each individual feature, system, system upgrade, and/or method described. In addition, any combination of two or more such features, systems, and/or methods, if such features, systems, system upgrade, and/or methods are not mutually inconsistent, is included within the inventive scope of the present disclosure.

Further, though some advantages of the present invention may be indicated, it should be appreciated that not every embodiment of the invention will include every described advantage. Some embodiments may not implement any features described as advantageous. Accordingly, the foregoing description and drawings are by way of example only.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used are for organizational purposes only and are not to be construed as limiting the subject matter described in any way.

Also, the technology described may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used, should be understood to control over dictionary definitions, definitions in documents incorporated by reference, and/or ordinary meanings of the defined terms.

Numerical values and ranges may be described in the specification and claims as approximate or exact values or ranges. For example, in some cases the terms "about," "approximately," and "substantially" may be used in reference to a value. Such references are intended to encompass the referenced value as well as plus and minus reasonable variations of the value. For example, a phrase "between about 10 and about 20" is intended to mean "between exactly 10 and exactly 20" in some embodiments, as well as "between $10\pm\delta1$ and $20\pm\delta2$" in some embodiments. The amount of variation $\delta1$, $\delta2$ for a value may be less than 5% of the value in some embodiments, less than 10% of the value in some embodiments, and yet less than 20% of the value in some embodiments. In embodiments where a large range of values is given, e.g., a range including two or more orders of magnitude, the amount of variation $\delta1$, $\delta2$ for a value could be as high as 50%. For example, if an operable range extends from 2 to 200, "approximately 80" may encompass values between 40 and 120 and the range may be as large as between 1 and 300. When exact values are intended, the term "exactly" is used, e.g., "between exactly 2 and exactly 200."

The term "adjacent" may refer to two elements arranged within close proximity to one another (e.g., within a distance that is less than about one-fifth of a transverse or vertical dimension of a larger of the two elements). In some cases there may be intervening structures or layers between adjacent elements. In some cases adjacent elements may be immediately adjacent to one another with no intervening structures or elements.

The indefinite articles "a" and "an," as used in the specification and in the claims, unless clearly indicated to the contrary, should be understood to mean "at least one."

The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

The invention claimed is:

1. A mode-locked laser module comprising:
    a base chassis;
    an output coupler and a first focusing optic mounted on the base chassis;
    a saturable absorber mirror and second focusing optic mounted on the base chassis, wherein the output coupler and saturable absorber mirror comprise end mirrors of a laser cavity of the mode-locked laser module;
    a gain medium located along an optical axis of an intracavity beam within the laser cavity; and
    a cavity length extending region comprising two reflectors located between the output coupler and the saturable absorber mirror, wherein the two reflectors fold the intracavity beam more than two times.

2. The mode-locked laser module of claim 1, further comprising a laser diode arranged to excite the gain medium with a pump beam, wherein absorption of the pump beam in the gain medium causes thermal lensing in the gain medium to a value between one diopter and 15 diopters when the mode-locked laser is producing optical pulses.

3. The mode-locked laser module of claim 2, wherein the mode-locked laser produces optical pulses stably without mechanical adjustments to the laser cavity for thermal lensing values varied over a range from 8 diopters to 12 diopters due to changes in optical power of the pump beam.

4. The mode-locked laser module of claim 3, wherein the changes in the optical power of the pump beam are between 2 Watts and 10 Watts and an average output optical power from the mode-locked laser module is between 350 milliwatts and 3.5 watts.

5. The mode-locked laser module of claim 1, wherein the gain medium comprises a solid state crystal that is disposed in a mount and has no active cooling.

6. The mode-locked laser module of claim 1, wherein the gain medium comprises neodymium vanadate ($Nd^{3+}$:$YVO_4$).

7. The mode-locked laser module of claim 1, wherein a pulse repetition rate of optical pulses produced by the mode-locked laser module is between 50 MHz and 200 MHz and a maximum edge length of the base chassis is not more than 350 mm.

8. The mode-locked laser module of claim 1, wherein a pulse repetition rate of optical pulses produced by the mode-locked laser module is between 50 MHz and 200 MHz and wherein the mode-locked laser module has a slab form with a maximum edge length measuring not more than 350 mm and a thickness measuring not more than 40 mm and a weight of the mode-locked laser module is no more than 2 kilograms.

9. The mode-locked laser module of claim 1, wherein a pulse repetition rate of optical pulses produced by the mode-locked laser module is between 50 MHz and 200 Mhz and wherein a maximum volume occupied by the mode-locked laser module is not more than 0.1 cubic feet.

10. The mode-locked laser module of claim 1, further comprising a diagonal rib extending diagonally across the base chassis that increases torsional stiffness of the base chassis, wherein the intracavity beam passes through multiple openings in the diagonal rib.

11. The mode-locked laser module of claim 1, wherein the saturable absorber mirror is mounted on a plate that is configured to be adjusted with only two degrees of freedom which do not include angle adjustments with respect to the optical axis of the intracavity beam that is incident on the saturable absorber mirror.

12. The mode-locked laser module of claim 11, wherein the plate comprises a printed circuit board having a metal coating or the plate comprises a plate of metal.

13. The mode-locked laser module of claim 1, wherein a first beam waist of the intracavity beam within the gain medium is between 100 microns and 150 microns and a second beam waist of the intracavity beam at the saturable absorber is between 75 microns and 125 microns.

14. The mode-locked laser module of claim 1, wherein the first focusing optic is located within the laser cavity between the gain medium and the saturable absorber mirror and the second focusing optic is located within the laser cavity between the first focusing optic and the saturable absorber mirror, and wherein the intracavity beam between the first focusing optic and the second focusing optic is essentially collimated.

15. The mode-locked laser module of claim 14, wherein a focal length of the first focusing optic is between 240 mm and 260 mm and a focal length of the second focusing optic is between 240 mm and 260 mm.

16. The mode-locked laser module of claim 14, wherein the output coupler is located between 280 mm and 300 mm from the first focusing optic and the gain medium is located between 4 mm and 8 mm from the output coupler.

17. The mode-locked laser module of claim 14, further comprising a frequency-doubling crystal mounted on the base chassis and arranged to double a frequency of an output beam from the laser cavity.

18. The mode-locked laser module of claim 1, further comprising a laser window or optical flat located within the laser cavity, wherein the second focusing optic and laser window or optical flat are arranged to adjust an incident angle of the intracavity beam on the saturable absorber mirror by rotating the laser window or optical flat.

19. The mode-locked laser module of claim 1, wherein one of the two reflectors folds the intracavity beam three times.

20. A mode-locked laser module comprising:
a base chassis;
a mode-locked laser having a first laser cavity configured to operate at a pulse repetition rate between 50 MHz and 200 MHz, wherein the mode-locked laser is assembled on the base chassis;
a first end mirror of the first laser cavity located at a first end of the first laser cavity;
a second end mirror of the first laser cavity located at a second end of the first laser cavity; and
a gain medium located within the first laser cavity, wherein the gain medium is configured to exhibit thermal lensing when pumped at an operating power for the first laser cavity, wherein the thermal lensing supports lasing in a second laser cavity formed within the first laser cavity that is less than one-half the length of the first laser cavity and that includes the first end mirror and a third end mirror that is installed on the base chassis in the first laser cavity.

21. The mode-locked laser module of claim 20, wherein the first end mirror, third end mirror, and thermally lensing gain medium form a stable lasing cavity with no additional lensing element.

22. The mode-locked laser module of claim 20, wherein the gain medium comprises a solid state crystal that is disposed in a mount and has no active cooling.

23. The mode-locked laser module of claim 20, wherein the gain medium comprises neodymium vanadate ($Nd^{3+}$:$YVO_4$).

24. The mode-locked laser module of claim 20, wherein a maximum edge length of the base chassis is not more than 350 mm.

25. The mode-locked laser module of claim 20, wherein the mode-locked laser module has a slab form with a maximum edge length measuring not more than 350 mm and a thickness measuring not more than 40 mm and a weight of the mode-locked laser module is no more than 2 kilograms.

26. The mode-locked laser module of claim 20, wherein a maximum volume occupied by the mode-locked laser module is not more than 0.1 cubic feet.

27. The mode-locked laser module of claim 20, further comprising a diagonal rib extending diagonally across the base chassis that increases torsional stiffness of the base chassis, wherein an intracavity beam of the first laser cavity passes through multiple openings in the diagonal rib.

28. The mode-locked laser module of claim 20, further comprising a reflector in the first laser cavity that folds an intracavity beam of the first laser cavity multiple times.

29. A method of operating a mode-locked laser, the method comprising:
pumping a gain medium of a laser cavity with an optical pump beam, such that the gain medium exhibits thermal lensing having a range of diopter values between 8 diopters and 12 diopters;

reflecting an intracavity beam from and output coupler at a first end of the laser cavity and a saturable absorber mirror at a second end of the laser cavity; and producing an output of stable optical pulses over the range of diopter values.

30. The method of claim 29, further comprising pumping the gain medium of the laser cavity, such that the gain medium exhibits thermal lensing having a range of diopter values between one diopter and 15 diopters.

31. The method of claim 29, further comprising adjusting an amount of the thermal lensing by tuning a wavelength of the optical pump beam.

32. The method of claim 29, further comprising reflecting the intracavity beam from a first focusing reflector and a second focusing reflector located between the gain medium and the saturable absorber mirror.

33. The method of claim 32, further comprising adjusting an incident angle of the intracavity beam on the saturable absorber mirror without adjusting an orientation angle of the saturable absorber mirror with respect to a chassis supporting the gain medium, the output coupler, and the saturable absorber mirror.

34. The method of claim 29, further comprising reflecting the intracavity beam from a plurality of mirrors located between the gain medium and the saturable absorber mirror to extend a length of the laser cavity.

35. The method of claim 34, further comprising reflecting the intracavity beam between two mirrors of the plurality of mirrors more than two times on immediately successive reflections.

36. The method of claim 34, further comprising applying an aperture to the intracavity beam to suppress higher-order modes.

37. The method of claim 29, wherein the optical pulses have a pulse repetition rate between 50 MHz and 200 MHz and a chassis on which the output coupler and saturable absorber mirror are mounted has an maximum edge dimension no larger than 350 mm.

38. The method of claim 29, wherein pumping the gain medium comprises providing between 2 Watts and 10 Watts of optical power to the gain medium and an average output power from the mode-locked laser module is between 350 milliwatts and 3.5 watts.

39. The method of claim 29, wherein a full-width-half-maximum pulse width of the optical pulses is between 9 picoseconds and 38 picoseconds.

* * * * *